(12) United States Patent
Remiszewski et al.

(10) Patent No.: US 6,552,065 B2
(45) Date of Patent: Apr. 22, 2003

(54) DEACETYLASE INHIBITORS

(75) Inventors: Stacy William Remiszewski, Washington Township, NJ (US); Kenneth Walter Bair, Mountain Lakes, NJ (US); Richard William Versace, Wanaque, NJ (US); Lawrence Blas Perez, Hackettstown, NJ (US); Michael Alan Green, Easton, PA (US); Lidia Cristina Sambucetti, Pacifica, CA (US); Sushil Sharma, West Orange, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/944,275

(22) Filed: Aug. 31, 2001

(65) Prior Publication Data

US 2003/0018062 A1 Jan. 23, 2003

Related U.S. Application Data

(60) Provisional application No. 60/307,490, filed on Jul. 24, 2001, provisional application No. 60/292,232, filed on May 18, 2001, and provisional application No. 60/229,943, filed on Sep. 1, 2000.

(51) Int. Cl.[7] ............... A61K 31/40; A61K 31/4035; C07D 209/44; C07D 401/04
(52) U.S. Cl. ............... 514/416; 514/419; 514/339; 546/277.1; 548/470; 548/506
(58) Field of Search ............... 514/419, 339, 514/416; 548/506, 470; 546/277.1

(56) References Cited

FOREIGN PATENT DOCUMENTS

| | | |
|---|---|---|
| JP | 10182583 | 7/1998 |
| WO | WO 93/12075 | 6/1993 |
| WO | WO 95/31977 | 11/1995 |
| WO | WO 97/35990 | 10/1997 |
| WO | WO 98/55449 | 12/1998 |
| WO | WO 00/23112 | 4/2000 |
| WO | WO 01/18171 A2 | 3/2001 |
| WO | WO 01/38322 A1 | 5/2001 |
| WO | WO 01/42437 A2 | 6/2001 |
| WO | WO 01/70675 A2 | 9/2001 |

OTHER PUBLICATIONS

M. Yoshida et al., "Histone deacetylase as a new target for cancer chemotherapy" Cancer Chemother. Pharmacol., vol. 48, Suppl. 1, Jul. 1, 2001, pp. S20–S–26, XP–002188621.

Buggy et al., "Cloning and characterization of a novel human histone deacetylase, HDAC8," Biochemical Society, vol. 350, pp. 199–205 (2000).

Kim et al., "Oxamflatin is a novel antitumor compound that inhibits mammalian histone deacetylase," Oncogene, vol. 18, pp. 2461–2470 (1999).

Lavoie et al., "Design and Synthesis of a Novel Class of Histone Deacetylase Inhibitors," Bioorg. & Med.Chem.Letters, vol. 11, pp. 2847–2850 (2001).

Taunton et al., "Synthesis of Natural and Modified Trapoxins, Useful Reagents for Exploring Histone Deacetylase Function," American Chemical Society, vol. 118, pp. 10412–10422 (1996).

*Primary Examiner*—Joseph K. McKane
*Assistant Examiner*—Sonya Wright
(74) *Attorney, Agent, or Firm*—George R. Dohmann

(57) ABSTRACT

The present invention provides hydroxamate compounds which are deacetylase inhibitors. The compounds are suitable for pharmaceutical compositions having antiproliferative properties.

27 Claims, No Drawings

DEACETYLASE INHIBITORS

This application claims the benefit of Provisional Application No. 60/307,490 filed Jul. 24, 2001, Provisional Application No. 60/292,232 filed May 18, 2001, and Provisional Application No. 60/229,943 filed Sep. 1, 2000, the disclosure of which is herein incorporated by reference.

The present invention relates to hydroxamate compounds which are inhibitors of histone deacetylase. The inventive compounds are useful as pharmaceuticals for the treatment of proliferative diseases.

BACKGROUND

Reversible acetylation of histones is a major regulator of gene expression that acts by altering accessibility of transcription factors to DNA. In normal cells, histone deacetylase (HDA) and histone acetyltrasferase together control the level of acetylation of histones to maintain a balance. Inhibition of HDA results in the accumulation of hyperacetylated histones, which results in a variety of cellular responses.

Inhibitors of HDA have been studied for their therapeutic effects on cancer cells. For example, butyric acid and its derivatives, including sodium phenylbutyrate, have been reported to induce apoptosis in vitro in human colon carcinoma, leukemia and retinoblastoma cell lines. However, butyric acid and its derivatives are not useful pharmacological agents because they tend to be metabolized rapidly and have a very short half-life in vivo. Other inhibitors of HDA that have been widely studied for their anti-cancer activities are trichostatin A and trapoxin. Trichostatin A is an antifungal and antibiotic and is a reversible inhibitor of mammalian HDA Trapoxin is a cyclic tetrapeptide, which is an irreversible inhibitor of mammalian HDA. Although trichostatin and trapoxin have been studied for their anti-cancer activities, the in vivo instability of the compounds makes them less suitable as anti-cancer drugs. There remains a need for an active compound that is suitable for treating tumors, including cancerous tumors, that is highly efficacious and stable.

SUMMARY

The present invention provides efficacious deacetylase inhibitor compounds that are useful as pharmaceutical agents having the formula (I):

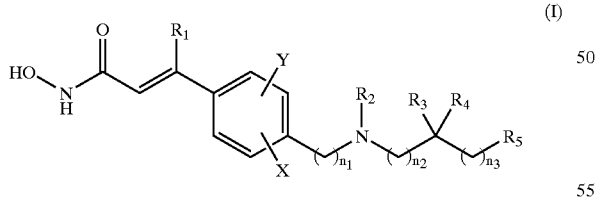

wherein
- $R_1$ is H, halo, or a straight chain $C_1$–$C_6$ alkyl (especially methyl, ethyl or n-propyl, which methyl, ethyl and n-propyl substituents are unsubstituted or substituted by one or more substituents described below for alkyl substituents);
- $R_2$ is selected from H, $C_1$–$C_{10}$ alkyl, (e.g. methyl, ethyl or —$CH_2CH_2$—OH), $C_4$–$C_9$ cycloalkyl, $C_4$–$C_9$ heterocycloalkyl, $C_4$–$C_9$ heterocycloalkylalkyl, cycloalkylalkyl (e.g., cyclopropylmethyl), aryl, heteroaryl, arylalkyl (e.g. benzyl), heteroarylalkyl (e.g. pyridylmethyl), —$(CH_2)_nC(O)R_6$, —$(CH_2)_nOC(O)R_6$, amino acyl, HON—C(O)—CH═C($R_1$)-aryl-alkyl- and —$(CH_2)_nR_7$;
- $R_3$ and $R_4$ are the same or different and independently H, $C_1$–$C_6$ alkyl, acyl or acylamino, or $R_3$ and $R_4$ together with the carbon to which they are bound represent C═O, C═S, or C═$NR_8$, or $R_2$ together with the nitrogen to which it is bound and $R_3$ together with the carbon to which it is bound can form a $C_4$–$C_9$ heterocycloalkyl, a heteroaryl, a polyheteroaryl, a non-aromatic polyheterocycle, or a mixed aryl and non-aryl polyheterocycle ring;
- $R_5$ is selected from H, $C_1$–$C_6$ alkyl, $C_4$–$C_9$ cycloalkyl, $C_4$–$C_9$ heterocycloalkyl, acyl, aryl, heteroaryl, arylalkyl (e.g. benzyl), heteroarylalkyl (e.g. pyridylmethyl), aromatic polycycles, non-aromatic polycycles, mixed aryl and non-aryl polycycles, polyheteroaryl, non-aromatic polyheterocycles, and mixed aryl and non-aryl polyheterocycles;
- n, $n_1$, $n_2$ and $n_3$ are the same or different and independently selected from 0–6, when $n_1$ is 1–6, each carbon atom can be optionally and independently substituted with $R_3$ and/or $R_4$;
- X and Y are the same or different and independently selected from H, halo, $C_1$–$C_4$ alkyl, such as $CH_3$ and $CF_3$, $NO_2$, $C(O)R_1$, $OR_9$, $SR_9$, CN, and $NR_{10}R_{11}$;
- $R_6$ is selected from H, $C_1$–$C_6$ alkyl, $C_4$–$C_9$ cycloalkyl, $C_4$–$C_9$ heterocycloalkyl, cycloalkylalkyl (e.g., cyclopropylmethyl), aryl, heteroaryl, arylalkyl (e.g., benzyl, 2-phenylethenyl), heteroarylalkyl (e.g., pyridylmethyl), $OR_{12}$, and $NR_{13}R_{14}$;
- $R_7$ is selected from $OR_{15}$, $SR_{15}$, $S(O)R_{16}$, $SO_2R_{17}$, $NR_{13}R_{14}$, and $NR_{12}SO_2R_6$;
- $R_8$ is selected from H, $OR_{15}$, $NR_{13}R_{14}$, $C_1$–$C_6$ alkyl, $C_4$–$C_9$ cycloalkyl, $C_4$–$C_9$ heterocycloalkyl, aryl, heteroaryl, arylalkyl (e.g., benzyl), and heteroarylalkyl (e.g., pyridylmethyl);
- $R_9$ is selected from $C_1$–$C_4$ alkyl, for example, $CH_3$ and $CF_3$, C(O)-alkyl, for example C(O)$CH_3$, and C(O)$CF_3$;
- $R_{10}$ and $R_{11}$ are the same or different and independently selected from H, $C_1$–$C_4$ alkyl, and —C(O)-alkyl;
- $R_{12}$ is selected from H, $C_1$–$C_6$ alkyl, $C_4$–$C_9$ cycloalkyl, $C_4$–$C_9$ heterocycloalkyl, $C_4$–$C_9$ heterocycloalkylalkyl, aryl, mixed aryl and non-aryl polycycle, heteroaryl, arylalkyl (e.g., benzyl), and heteroarylalkyl (e.g., pyridylmethyl);
- $R_{13}$ and $R_{14}$ are the same or different and independently selected from H, $C_1$–$C_6$ alkyl, $C_4$–$C_9$ cycloalkyl, $C_4$–$C_9$ heterocycloalkyl, aryl, heteroaryl, arylalkyl (e.g., benzyl), heteroarylalkyl (e.g., pyridylmethyl), amino acyl, or $R_{13}$ and $R_{14}$ together with the nitrogen to which they are bound are $C_4$–$C_9$ heterocycloalkyl, heteroaryl, polyheteroaryl, non-aromatic polyheterocycle or mixed aryl and non-aryl polyheterocycle;
- $R_{15}$ is selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl and $(CH_2)_mZR_{12}$;
- $R_{16}$ is selected from $C_1$–$C_6$ alkyl, $C_4$–$C_9$ cycloalkyl, $C_4$–$C_9$ heterocycloalkyl, aryl, heteroaryl, polyheteroaryl, arylalkyl, heteroarylalkyl and $(CH_2)_mZR_{12}$;
- $R_{17}$ is selected from $C_1$–$C_6$ alkyl, $C_4$–$C_9$ cycloalkyl, $C_4$–$C_9$ heterocycloalkyl, aryl, aromatic polycycles, heteroaryl, arylalkyl, heteroarylalkyl, polyheteroaryl and $NR_{13}R_{14}$;

m is an integer selected from 0 to 6; and

Z is selected from O $NR_{13}$, S and S(O), or a pharmaceutically acceptable salt thereof.

The compounds of the present invention are suitable as active agents in pharmaceutical compositions that are efficacious particularly for treating cellular proliferative ailments. The pharmaceutical composition has ia pharmaceutically effective amount of the present active agent along with other pharmaceutically acceptable exicipients, carriers, fillers, diluents and the like. The term pharmacuetically effective amount as used herein indicates an amount necessary to administer to a host to achieve a therapeutic result, especially an anti-tumor effect, e.g., inhibition of proliferation of malignant cancer cells, benign tumor cells or other proliferative cells.

DETAILED DESCRIPTION

The present invention provides hydroxamate compounds, e.g., hydroxamic acids, that are inhibitors of deacetylases, preferably inhibitors of histone deacetylases. The hydroxamate compounds are highly suitable for treating tumors, including cancerous tumors. The hydroxamate compounds of the present invention have the following structure (I):

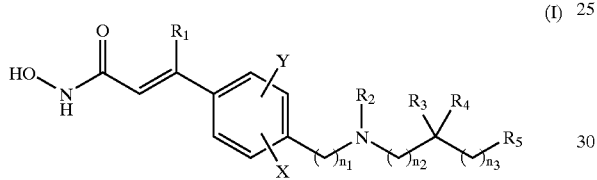

wherein $R_1$ is H, halo, or a straight chain $C_1$–$C_6$ alkyl (especially methyl, ethyl or n-propyl, which methyl, ethyl and n-propyl substituents are unsubstituted or substituted by one or more substituents described below for alkyl substituents);

$R_2$ is selected from H, $C_1$–$C_{10}$ alkyl, (preferably $C_1$–$C_6$ alkyl, e.g. methyl, ethyl or —$CH_2CH_2$—OH), $C_4$–$C_9$ cycloalkyl, $C_4$–$C_9$ heterocycloalkyl, $C_4$–$C_9$ heterocycloalkylalkyl, cycloalkylalkyl (e.g., cyclopropylmethyl), aryl, heteroaryl, arylalkyl (e.g. benzyl), heteroarylalkyl (e.g. pyridylmethyl), —$(CH_2)_n$ C(O)$R_6$, —$(CH_2)_n$OC(O)$R_6$, amino acyl, HON—C (O)—CH=C($R_1$)-aryl-alkyl- and —$(CH_2)_nR_7$;

$R_3$ and $R_4$ are the same or different and independently H, $C_1$–$C_6$ alkyl, acyl or acylamino, or $R_3$ and $R_4$ together with the carbon to which they are bound represent C=O, C=S, or C=$NR_8$, or $R_2$ together with the nitrogen to which it is bound and $R_3$ together with the carbon to which it is bound can form a $C_4$–$C_9$ heterocycloalkyl, a heteroaryl, a polyheteroaryl, a non-aromatic polyheterocycle, or a mixed aryl and non-aryl polyheterocycle ring;

$R_5$ is selected from H, $C_1$–$C_6$ alkyl, $C_4$–$C_9$ cycloalkyl, $C_4$–$C_9$ heterocycloalkyl, acyl, aryl, heteroaryl, arylalkyl (e.g. benzyl), heteroarylalkyl (e.g. pyridylmethyl), aromatic polycycles, non-aromatic polycycles, mixed aryl and non-aryl polycycles, polyheteroaryl, non-aromatic polyheterocycles, and mixed aryl and non-aryl polyheterocycles;

n, $n_1$, $n_2$ and $n_3$ are the same or different and independently selected from 0–6, when $n_1$ is 1–6, each carbon atom can be optionally and independently substituted with $R_3$ and/or $R_4$;

X and Y are the same or different and independently selected from H, halo, $C_1$–$C_4$alkyl, such as $CH_3$ and $CF_3$, $NO_2$, C(O)$R_1$, $OR_9$, $SR_9$, CN, and $NR_{10}R_{11}$;

$R_6$ is selected from H, $C_1$–$C_6$ alkyl, $C_4$–$C_9$ cycloalkyl, $C_4$–$C_9$ heterocycloalkyl, cycloalkylalkyl (e.g., cyclopropylmethyl), aryl, heteroaryl, arylalkyl (e.g., benzyl, 2-phenylethenyl), heteroarylalkyl (e.g., pyridylmethyl), $OR_{12}$, and $NR_{13}R_{14}$;

$R_7$ is selected from $OR_{15}$, $SR_{15}$, S(O)$R_{16}$, $SO_2R_{17}$, $NR_{13}R_{14}$, and $NR_{12}SO_2R_6$;

$R_8$ is selected from H, $OR_{15}$, $NR_{13}R_{14}$, $C_1$–$C_6$ alkyl, $C_4$–$C_9$ cycloalkyl, $C_4$–$C_9$ heterocycloalkyl, aryl, heteroaryl, arylalkyl (e.g., benzyl), and heteroarylalkyl (e.g., pyridylmethyl);

$R_9$ is selected from $C_1$–$C_4$alkyl, for example, $CH_3$ and $CF_3$, C(O)-alkyl, for example C(O)$CH_3$, and C(O)$CF_3$;

$R_{10}$ and $R_{11}$ are the same or different and independently selected from H, $C_1$–$C_4$ alkyl, and —C(O)-alkyl;

$R_{12}$ is selected from H, $C_1$–$C_6$ alkyl, $C_4$–$C_9$ cycloalkyl, $C_4$–$C_9$ heterocycloalkyl, $C_4$–$C_9$ heterocycloalkylalkyl, aryl, mixed aryl and non-aryl polycycle, heteroaryl, arylalkyl (e.g., benzyl), and heteroarylalkyl (e.g., pyridylmethyl);

$R_{13}$ and $R_{14}$ are the same or different and independently selected from H, $C_1$–$C_6$ alkyl, $C_4$–$C_9$ cycloalkyl, $C_4$–$C_9$ heterocycloalkyl, aryl, heteroaryl, arylalkyl (e.g., benzyl), heteroarylalkyl (e.g., pyridylmethyl), amino acyl, or $R_{13}$ and $R_{14}$ together with the nitrogen to which they are bound are $C_4$–$C_9$ heterocycloalkyl, heteroaryl, polyheteroaryl, non-aromatic polyheterocycle or mixed aryl and non-aryl polyheterocycle;

$R_{15}$ is selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl and $(CH_2)_mZR_{12}$;

$R_{16}$ is selected from $C_1$–$C_6$ alkyl, $C_4$–$C_9$ cycloalkyl, $C_4$–$C_9$ heterocycloalkyl, aryl, heteroaryl, polyheteroaryl, arylalkyl, heteroarylalkyl and $(CH_2)_mZR_{12}$;

$R_{17}$ is selected from $C_1$–$C_6$ alkyl, $C_4$–$C_9$ cycloalkyl, $C_4$–$C_9$ heterocycloalkyl, aryl, aromatic polycycles, heteroaryl, arylalkyl, heteroarylalkyl, polyheteroaryl and $NR_{13}R_{14}$;

m is an integer selected from 0 to 6; and

Z is selected from O $NR_{13}$, S and S(O), or a pharmaceutically acceptable salt thereof.

As appropriate, unsubstituted means that there is no substituent or that the only substituents are hydrogen.

Halo substituents are selected from fluoro, chloro, bromo and iodo, preferably fluoro or chloro.

Alkyl substituents include straight and branched $C_1$–$C_6$alkyl, unless otherwise noted. Examples of suitable straight and branched $C_1$–$C_6$alkyl substituents include methyl, ethyl, n-propyl, 2-propyl, n-butyl, sec-butyl, t-butyl, and the like. Unless otherwise noted, the alkyl substituents include both unsubstituted alkyl groups and alkyl groups that are substituted by one or more suitable substituents, including unsaturation (i.e. there are one or more double or triple C—C bonds), acyl, cycloalkyl, halo, oxyalkyl, alkylamino, aminoalkyl, acylamino and $OR_{15}$, for example, alkoxy. Preferred substituents for alkyl groups include halo, hydroxy, alkoxy, oxyalkyl, alkylamino, and aminoalkyl.

Cycloalkyl substituents include $C_3$–$C_9$ cycloalkyl groups, such as cyclopropyl, cyclobutyl, cyclopentyl, cyclohexyl and the like, unless otherwise specified. Unless otherwise noted, cycloalkyl substituents include both unsubstituted cycloalkyl groups and cycloalkyl groups that are substituted by one or more suitable substituents, including $C_1$–$C_6$ alkyl, halo, hydroxy, aminoalkyl, oxyalkyl, alkylamino, and $OR_{15}$, such as alkoxy. Preferred substituents for cycloalkyl groups include halo, hydroxy, alkoxy, oxyalkyl, alkylamino and aminoalkyl.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

Heterocycloalkyl substituents include 3 to 9 membered aliphatic rings, such as 4 to 7 membered aliphatic rings, containing from one to three heteroatoms selected from nitrogen, sulfur, oxygen. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. Unless otherwise noted, the rings are unsubstituted or substuted on the carbon atoms by one or more suitable substituents, including $C_1$–$C_6$ alkyl, $C_4$–$C_9$ cycloalkyl, aryl, heteroaryl, arylalkyl (e.g., benzyl), and heteroarylalkyl (e.g., pyridylmethyl), halo, amino, alkyl amino and $OR_{15}$, for example alkoxy. Unless otherwise noted, nitrogen heteroatoms are unsubstituted or substituted by H, $C_1$–$C_4$ alkyl, arylalkyl (e.g., benzyl), and heteroarylalkyl (e.g., pyridylmethyl), acyl, aminoacyl, alkylsulfonyl, and arylsulfonyl.

Cycloalkylalkyl substituents include compounds of the formula —$CH_2)_{n5}$-cycloalkyl wherein n5 is a number from 1–6. Suitable alkylcycloalkyl substituents include cyclopentylmethyl-, cyclopentylethyl, cyclohexylmethyl and the like. Such substituents are unsubstituted or substituted in the alkyl portion or in the cycloalkyl portion by a suitable substituent, including those listed above for alkyl and cycloalkyl.

Aryl substituents include unsubstituted phenyl and phenyl substituted by one or more suitable substituents, including $C_1$–$C_6$ alkyl, cycloalkylalkyl (e.g., cyclopropylmethyl), O(CO)alkyl, oxyalkyl, halo, nitro, amino, alkylamino, aminoalkyl, alkyl ketones, nitrile, carboxyalkyl, alkylsulfonyl, aminosulfonyl, arylsulfonyl, and $OR_{15}$, such as alkoxy. Preferred substituents include including $C_1$–$C_6$ alkyl, cycloalkyl (e.g., cyclopropylmethyl), alkoxy, oxyalkyl, halo, nitro, amino, alkylamino, aminoalkyl, alkyl ketones, nitrile, carboxyalkyl, alkylsulfonyl, arylsulfonyl, and aminosulfonyl. Examples of suitable aryl groups include $C_1$–$C_4$ alkylphenyl, $C_1$–$C_4$ alkoxyphenyl, trifluoromethylphenyl, methoxyphenyl, hydroxyethylphenyl, dimethylaminophenyl, aminopropylphenyl, carbethoxyphenyl, methanesulfonylphenyl and tolylsulfonylphenyl.

Aromatic polycycles include naphthyl, and naphthyl substituted by one or more suitable substituents, including $C_1$–$C_6$ alkyl, alkylcycloalkyl (e.g., cyclopropylmethyl), oxyalkyl, halo, nitro, amino, alkylamino, aminoalkyl, alkyl ketones, nitrile, carboxyalkyl, alkylsulfonyl, arylsulfonyl, aminosulfonyl and $OR_{15}$, such as alkoxy.

Heteroaryl substituents include compounds with a 5 to 7 member aromatic ring containing one or more heteroatoms, for example from 1 to 4 heteroatoms, selected from N, O and S. Typical heteroaryl substituents include furyl, thienyl, pyrrole, pyrazole, triazole, thiazole, oxazole, pyridine, pyrimidine, isoxazolyl, pyrazine and the like. Unless otherwise noted, heteroaryl substituents are unsubstituted or substituted on a carbon atom by one or more suitable substituents, including alkyl, the alkyl substituents identified above, and another heteroaryl substituent. Nitrogen atoms are unsubstituted or substituted, for example by $R_{13}$; especially useful N substituents include H, $C_1$–$C_4$ alkyl, acyl, aminoacyl, and sulfonyl.

Arylalkyl substituents include groups of the formula —$(CH_2)_{n5}$-aryl, —$(CH_2)_{n5-1}$—$(CHaryl)$—$(CH_2)_{n5}$-aryl or —$(CH_2)_{n5-1}CH(aryl)(aryl)$ wherein aryl and n5 are defined above. Such arylalkyl substituents include benzyl, 2-phenylethyl, 1-phenylethyl, tolyl-3-propyl, 2-phenylpropyl, diphenylmethyl, 2-diphenylethyl, 5,5-dimethyl-3-phenylpentyl and the like. Arylalkyl substituents are unsubstituted or substituted in the alkyl moiety or the aryl moiety or both as described above for alkyl and aryl substituents.

Heteroarylalkyl substituents include groups of the formula —$(CH_2)_{n5}$-heteroaryl wherein heteroaryl and n5 are defined above and the bridging group is linked to a carbon or a nitrogen of the heteroaryl portion, such as 2-, 3- or 4-pyridylmethyl, imidazolylmethyl, quinolylethyl, and pyrrolylbutyl. Heteroaryl substituents are unsubstituted or substituted as discussed above for heteroaryl and alkyl substituents.

Amino acyl substituents include groups of the formula —$C(O)$—$(CH_2)_n$—$C(H)(NR_{13}R_{14})$—$(CH_2)_n$—$R_5$ wherein n, $R_{13}$, $R_{14}$ and $R_5$ are described above. Suitable aminoacyl substituents include natural and non-natural amino acids such as glycinyl, D-tryptophanyl, L-lysinyl, D- or L-homoserinyl, 4-aminobutryic acyl, ±-3-amin-4-hexenoyl.

Non-aromatic polycycle substituents include bicyclic and tricyclic fused ring systems where each ring can be 4–9 membered and each ring can contain zero, 1 or more double and/or triple bonds. Suitable examples of non-aromatic polycycles include decalin, octahydroindene, perhydrobenzocycloheptene, perhydrobenzo-[f]-azulene. Such substituents are unsubstituted or substituted as described above for cycloalkyl groups.

Mixed aryl and non-aryl polycycle substituents include bicyclic and tricyclic fused ring systems where each ring can be 4–9 membered and at least one ring is aromatic. Suitable examples of mixed aryl and non-aryl polycycles include methylenedioxyphenyl, bis-methylenedioxyphenyl, 1,2,3,4-tetrahydronaphthalene, dibenzosuberane, dihdydroanthracene, 9H-fluorene. fluorene. Such substituents are unsubstituted or substituted by nitro or as described above for cycloalkyl groups.

Polyheteroaryl substituents include bicyclic and tricyclic fused ring systems where each ring can independently be 5 or 6 membered and contain one or more heteroatom, for example, 1, 2, 3, or 4 heteroatoms, chosen from O, N or S such that the fused ring system is aromatic. Suitable examples of polyheteroaryl ring systems include quinoline, isoquinoline, pyridopyrazine, pyrrolopyridine, furopyridine, indole, benzofuran, benzothiofuran, benzindole, benzoxazole, pyrroloquinoline, and the like. Unless otherwise noted, polyheteroaryl substituents are unsubstituted or substituted on a carbon atom by one or more suitable substituents, including alkyl, the alkyl substituents identified above and a substituent of the formula —O—$(CH_2CH=CH(CH_3)(CH_2))_{1-3}H$. Nitrogen atoms are unsubstituted or substituted, for example by $R_{13}$; especially useful N substituents include H, $C_1$–$C_4$ alkyl, acyl, aminoacyl, and sulfonyl.

Non-aromatic polyheterocyclic substituents include bicyclic and tricyclic fused ring systems where each ring can be 4–9 membered, contain one or more heteroatom, for example, 1, 2, 3, or 4 heteroatoms, chosen from O, N or S and contain zero or one or more C—C double or triple bonds. Suitable examples of non-aromatic polyheterocycles include hexitol, cis-perhydro-cyclohepta[b]pyridinyl, decahydro-benzo[f][1,4]oxazepinyl, 2,8-dioxabicyclo[3.30]octane, hexahydro-thieno[3,2-b]thiophene, perhydropyrrolo[3,2-b]pyrrole, perhydronaphthyridine, perhydro-1H-dicyclopenta[b,e]pyran. Unless otherwise noted, non-aromatic polyheterocyclic substituents are unsubstituted or substituted on a carbon atom by one or more substituents, including alkyl and the alkyl substituents identified above. Nitrogen atoms are unsubstituted or substituted, for example, by $R_{13}$; especially useful N substituents include H, $C_1$–$C_4$ alkyl, acyl, aminoacyl, and sulfonyl.

Mixed aryl and non-aryl polyheterocycles substituents include bicyclic and tricyclic fused ring systems where each ring can be 4–9 membered, contain one or more heteroatom chosen from O, N or S, and at least one of the rings must be aromatic. Suitable examples of mixed aryl and non-aryl polyheterocycles include 2,3-dihydroindole, 1,2,3,4-tetrahydroquinoline, 5,11-dihydro-10H-dibenz[b,e][1,4]diazepine, 5H-dibenzo[b,e][1,4]diazepine, 1,2-dihydropyrrolo[3,4-b][1,5]benzodiazepine, 1,5-dihydro-pyrido[2,3-b][1,4]diazepin-4-one, 1,2,3,4,6,11-hexahydro-benzo[b]pyrido[2,3-e][1,4]diazepin-5-one. Unless otherwise noted, mixed aryl and non-aryl polyheterocyclic substituents are unsubstituted or substituted on a carbon atom by one or more suitable substituents, including, —N—OH, =N—OH, alkyl and the alkyl substituents identified above. Nitrogen atoms are unsubstituted or substituted, for example, by $R_{13}$; especially useful N substituents include H, $C_1$–$C_4$ alkyl, acyl, aminoacyl, and sulfonyl.

Amino substituents include primary, secondary and tertiary amines and in salt form, quaternary amines. Examples of amino substituents include mono- and di-alkylamino, mono- and di-aryl amino, mono- and di-arylalkyl amino, aryl-arylalkylamino, alkyl-arylamino, alkyl-arylalkylamino and the like.

Sulfonyl substituents include alkylsulfonyl and arylsulfonyl, for example methane sulfonyl, benzene sulfonyl, tosyl and the like.

Acyl substituents include groups of formula —C(O)—W, —OC(O)—W, —C(O)—O—W or —C(O)NR$_{13}$R$_{14}$, where W is R$_{16}$, H or cycloalkylalkyl.

Acylamino substituents include substituents of the formula —N(R$_{12}$)C(O)—W, —N(R$_{12}$)C(O)—O—W, and —N(R$_{12}$)C(O)—NHOH and R$_{12}$ and W are defined above.

The R$_2$ substituent HON—C(O)CH=C(R$_1$)-aryl-alkyl- is a group of the formula

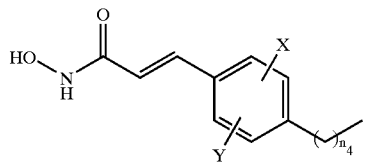

Preferences for each of the substituents include the following:

$R_1$ is H, halo, or a straight chain $C_1$–$C_4$ alkyl;
$R_2$ is selected from H, $C_1$–$C_6$ alkyl, $C_4$–$C_9$ cycloalkyl, $C_4$–$C_9$ heterocycloalkyl, alkylcycloalkyl, aryl, heteroaryl, arylalkyl, heteroarylalkyl, —(CH$_2$)$_n$C(O)R$_6$, amino acyl, and —(CH$_2$)$_n$R$_7$;
$R_3$ and $R_4$ are the same or different and independently selected from H, and $C_1$–$C_6$ alkyl, or $R_3$ and $R_4$ together with the carbon to which they are bound represent C=O, C=S, or C=NR$_8$;

$R_5$ is selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl, a aromatic polycycle, a non-aromatic polycycle, a mixed aryl and non-aryl polycycle, polyheteroaryl, a non-aromatic polyheterocycle, and a mixed aryl and non-aryl polyheterocycle;
n, $n_1$, $n_2$ and $n_3$ are the same or different and independently selected from 0–6, when $n_1$ is 1–6, each carbon atom is unsubstituted or independently substituted with $R_3$ and/or $R_4$;
X and Y are the same or different and independently selected from H, halo, $C_1$–$C_4$ alkyl, CF$_3$, NO$_2$, C(O)R$_1$, OR$_9$, SR$_9$, CN, and NR$_{10}$R$_{11}$;
$R_6$ is selected from H, $C_1$–$C_6$ alkyl, $C_4$–$C_9$ cycloalkyl, $C_4$–$C_9$ heterocycloalkyl, alkylcycloalkyl, aryl, heteroaryl, arylalkyl, heteroarylalkyl, OR$_{12}$, and NR$_{13}$R$_{14}$;
$R_7$ is selected from OR$_{15}$, SR$_{15}$, S(O)R$_{16}$, SO$_2$R$_{17}$, NR$_{13}$R$_{14}$, and NR$_{12}$SO$_2$R$_6$;
$R_8$ is selected from H, OR$_{15}$, NR$_{13}$R$_{14}$, $C_1$–$C_6$ alkyl, $C_4$–$C_9$ cycloalkyl, $C_4$–$C_9$ heterocycloalkyl, aryl, heteroaryl, arylalkyl, and heteroarylalkyl;
$R_9$ is selected from $C_1$–$C_4$ alkyl and C(O)-alkyl;
$R_{10}$ and $R_{11}$ are the same or different and independently selected from H, $C_1$–$C_4$ alkyl, and —C(O)-alkyl;
$R_{12}$ is selected from H, $C_1$–$C_6$ alkyl, $C_4$–$C_9$ cycloalkyl, $C_4$–$C_9$ heterocycloalkyl, aryl, heteroaryl, arylalkyl, and heteroarylalkyl;
$R_{13}$ and $R_{14}$ are the same or different and independently selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl and amino acyl;
$R_{15}$ is selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl and (CH$_2$)$_m$ZR$_{12}$;
$R_{16}$ is selected from $C_1$–$C_6$ alkyl, $C_4$–$C_9$ cycloalkyl, $C_4$–$C_9$ heterocycloalkyl, aryl, heteroaryl, arylalkyl, heteroarylalkyl and (CH$_2$)$_m$ZR$_{12}$;
$R_{17}$ is selected from $C_1$–$C_6$ alkyl, $C_4$–$C_9$ cycloalkyl, $C_4$–$C_9$ heterocydoalkyl, aryl, heteroaryl, arylalkyl, heteroarylalkyl and NR$_{13}$R$_{14}$;
m is an integer selected from 0 to 6; and
Z is selected from O, NR$_{13}$, S, S(O),
or a pharmaceutically acceptable salt thereof.

Useful compounds of the formula (I) include those wherein each of $R_1$, X, Y, $R_3$, and $R_4$ is H, including those wherein one of $n_2$ and $n_3$ is zero and the other is 1, especially those wherein $R_2$ is H or —CH$_2$—CH$_2$—OH.

One suitable genus of hydroxamate compounds are those of formula Ia:

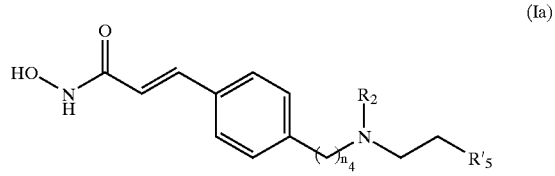

(Ia)

wherein
$n_4$ is 0–3,
$R_2$ is selected from H, $C_1$–$C_6$ alkyl, $C_4$–$C_9$ cycloalkyl, $C_4$–$C_9$ heterocycloalkyl, alkylcycloalkyl, aryl, heteroaryl, arylalkyl, heteroarylalkyl, —(CH$_2$)$_n$C(O)R$_6$, amino acyl and —(CH$_2$)$_n$R$_7$;

$R_5'$ is heteroaryl, heteroarylalkyl (e.g., pyridylmethyl), aromatic polycycles, non-aromatic polycycles, mixed aryl and non-aryl polycycles, polyheteroaryl, or mixed aryl and non-aryl polyheterocycles, or a pharmaceutically acceptable salt thereof.

Another suitable genus of hydroxamate compounds are those of formula Ia:

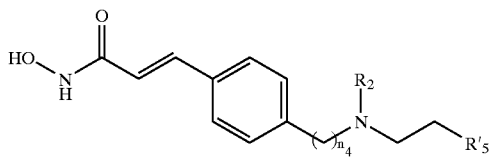

(Ia)

wherein $n_4$ is 0–3, $R_2$ is selected from H, $C_1$–$C_6$ alkyl, $C_4$–$C_9$ cycloalkyl, $C_4$–$C_9$ heterocycloalkyl, alkylcycloalkyl, aryl, heteroaryl, arylalkyl, heteroarylalkyl, —$(CH_2)_nC(O)$ $R_6$, amino acyl and —$(CH_2)_nR_7$;

$R_5'$ is aryl, arylalkyl, aromatic polycycles, non-aromatic polycycles, and mixed aryl and non-aryl polycycles; especially aryl, such as p-fluorophenyl, p-chlorophenyl, p-O-$C_1$–$C_4$-alkylphenyl, such as p-methoxyphenyl, and p-$C_1$–$C_4$-alkylphenyl; and arylalkyl, such as benzyl, ortho, meta or para-fluorobenzyl, ortho, meta or para-chlorobenzyl, ortho, meta or para-mono, di or tri-O-$C_1$–$C_4$-alkylbenzyl, such as ortho, meta or para-methoxybenzyl, m,p-diethoxybenzyl, o,m,p-triimethoxybenzyl, and ortho, meta or para- mono, di or tri $C_1$–$C_4$-alkylphenyl, such as p-methyl, m,m-diethylphenyl, or a pharmaceutically acceptable salt thereof.

Another interesting genus are the compounds of formula Ib:

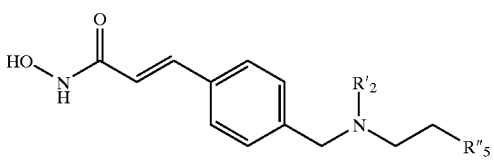

(Ib)

wherein $R_2'$ is selected from H, $C_1$–$C_6$ alkyl, $C_4$–$C_6$ cycloalkyl, cycloalkylalkyl (e.g., cyclopropylmethyl), $(CH_2)_{2-4}OR_{21}$ where $R_{21}$ is H, methyl, ethyl, propyl, and i-propyl, and $R_5''$ is unsubstituted 1H-indol-3-yl, benzofuran-3-yl or quinolin-3-yl, or substituted 1H-indol-3-yl, such as 5-fluoro-1H-indol-3-yl or 5-methoxy-1H-indol-3-yl, benzofuran-3-yl or quinolin-3-yl, or a pharmaceutically acceptable salt thereof.

Another interesting genus of hydroxamate compounds are the compounds of formula (Ic)

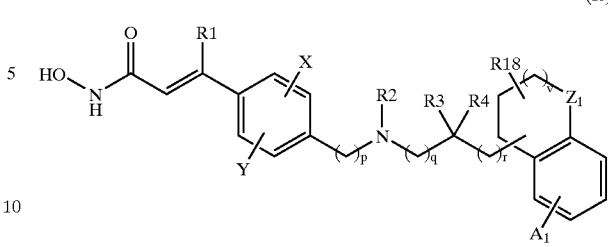

(Ic)

wherein the ring containing $Z_1$ is aromatic or non-aromatic, which non-aromatic rings are saturated or unsaturated, $Z_1$ is O, S or N—$R_{20}$, R18 is H, halo, $C_1$–$C_6$alkyl (methyl, ethyl, t-butyl), $C_3$–$C_7$cycloalkyl, aryl, for example unsubstituted phenyl or phenyl substituted by 4-$OCH_3$ or 4-$CF_3$, or heteroaryl, such as 2-furanyl, 2-thiophenyl or 2-, 3- or 4-pyridyl;

$R_{20}$ is H, $C_1$–$C_6$alkyl, $C_1$–$C_6$alkyl-$C_3$–$C_9$cycloalkyl (e.g., cyclopropylmethyl), aryl, heteroaryl, arylalkyl (e.g., benzyl), heteroarylalkyl (e.g., pyridylmethyl), acyl (acetyl, propionyl, benzoyl) or sulfonyl (methanesulfonyl, ethanesulfonyl, benzenesulfonyl, toluenesulfonyl) $A_1$ is 1, 2 or 3 substituents which are independently H, $C_1$–$C_{-6}$alkyl, —$OR_9$, halo, alkylamino, aminoalkyl, halo, or heteroarylalkyl (e.g., pyridylmethyl), $R_{19}$ is selected from H, $C_1$–$C_6$alkyl, $C_4$–$C_9$cycloalkyl, $C_4$–$C_9$heterocycloalkyl, aryl, heteroaryl, arylalkyl (e.g., benzyl), heteroarylalkyl (e.g., pyridylmethyl) and —$(CH_2CH=CH(CH_3)(CH_2))_{1-3}H$;

$R_2$ is selected from H, $C_1$–$C_6$ alkyl, $C_4$–$C_9$ cycloalkyl, $C_4$–$C_9$ heterocycloalkyl, alkylcycloalkyl, aryl, heteroaryl, arylalkyl, heteroarylalkyl, —$(CH_2)_nC(O)$ $R_6$, amino acyl and —$(CH_2)_nR_7$;

v is 0, 1 or 2, p is 0–3, and q is 1–5 and r is 0 or q is 0 and r is 1–5, or a pharmaceutically acceptable salt thereof. The other variable substituents are as defined above.

Especially useful compounds of formula (Ic) are those wherein $R_2$ is H, or —$(CH_2)_pCH_2OH$, wherein p is 1–3, especially those wherein $R_1$ is H; such as those wherein $R_1$ is H and X and Y are each H, and wherein q is 1–3 and r is 0 or wherein q is 0 and r is 1–3, especially those wherein $Z_1$ is N—$R_{20}$. Among these compounds $R_2$ is preferably H or —$CH_2$—$CH_2$—OH and the sum of q and r is preferably 1.

Another interesting genus of hydroxamate compounds are the compounds of formula (Id)

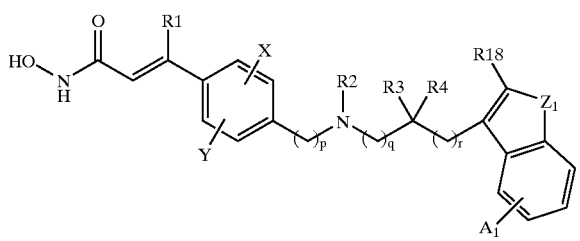

wherein $Z_1$ is O, S or N—$R_{20}$,

R18 is H, halo, $C_1$–$C_6$alkyl (methyl, ethyl, t-butyl), $C_3$–$C_7$cycloalkyl, aryl, for example, unsubstituted phenyl or phenyl substituted by 4-OCH$_3$ or 4-CF$_3$, or heteroaryl, $R_{20}$ is H, $C_1$–$C_6$alkyl, $C_1$–$C_6$alkyl-$C_3$–$C_9$cycloalkyl (e.g., cyclopropylmethyl), aryl, heteroaryl, arylalkyl (e.g., benzyl), heteroarylalkyl (e.g., pyridylmethyl), acyl (acetyl, propionyl, benzoyl) or sulfonyl (methanesulfonyl, ethanesulfonyl, benzenesulfonyl, toluenesulfonyl), $A_1$ is 1, 2 or 3 substituents which are independently H, $C_1$–$C_6$alkyl, —$OR_{19}$, or halo, $R_{19}$ is selected from H, $C_1$–$C_6$alkyl, $C_4$–$C_9$cycloalkyl, $C_4$–$C_9$heterocycloalkyl, aryl, heteroaryl, arylalkyl (e.g., benzyl), and heteroarylalkyl (e.g., pyridylmethyl);

p is 0–3, and q is 1–5 and r is 0 or q is 0 and r is 1–5, or a pharmaceutically acceptable salt thereof. The other variable substituents are as defined above.

Especially useful compounds of formula (Id) are those wherein $R_2$ is H, or —(CH$_2$)$_p$CH$_2$OH, wherein p is 1–3, especially those wherein $R_1$ is H; such as those wherein $R_1$ is H and X and Y are each H, and wherein q is 1–3 and r is 0 or wherein q is 0 and r is 1–3. Among these compounds $R_2$ is preferably H or —CH$_2$—CH$_2$—OH and the sum of q and r is preferably 1.

The present invention further relates to compounds of the formula (Ie)

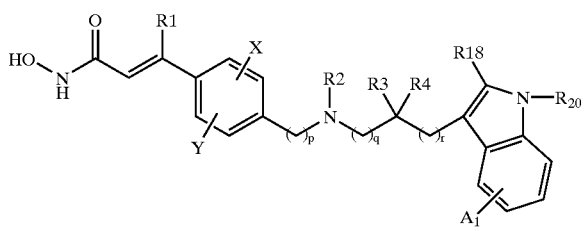

or a pharmaceutically acceptable salt thereof. The variable substituents are as defined above.

Especially useful compounds of formula (Ie) are those wherein R8 is H, fluoro, chloro, bromo, a $C_1$–$C_4$alkyl group, a substituted $C_1$–$C_4$alkyl group, a $C_3$–$C_7$cycloalkyl group, unsubstituted phenyl, phenyl substituted in the para position, or a heteroaryl (e.g., pyridyl) ring.

Another group of useful compounds of formula (Ie) are those wherein $R_2$ is H, or —(CH$_2$)$_p$CH$_2$OH, wherein p is 1–3, especially those wherein $R_1$ is H; such as those wherein $R_1$ is H and X and Y are each H, and wherein q is 1–3 and r is 0 or wherein q is 0 and r is 1–3. Among these compounds $R_2$ is preferably H or —CH$_2$—CH$_2$OH and the sum of q and r is preferably 1.

Another group of useful compounds of formula (Ie) are those wherein R18 is H, methyl, ethyl, t-butyl, trifluoromethyl, cyclohexyl, phenyl, 4-methoxyphenyl, 4-trifluoromethylphenyl, 2-furanyl, 2-thiophenyl, or 2-, 3- or 4-pyridyl wherein the 2-furanyl, 2-thiophenyl and 2-, 3or 4-pyridyl substituents are unsubstituted or substituted as described above for heteroaryl rings; $R_2$ is H, or —(CH$_2$)$_p$CH$_2$OH, wherein p is 1–3; especially those wherein $R_1$ is H and X and Y are each H, and wherein q is 1–3 and r is 0 or wherein q is 0 and r is 1–3. Among these compounds $R_2$ is preferably H or —CH$_2$—CH$_2$—OH and the sum of q and r is preferably 1.

Those compounds of formula Ie wherein $R_{20}$ is H or $C_1$–$C_6$alkyl, especially H, are important members of each of the subgenuses of compounds of formula Ie described above.

N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(1H-indol-3-yl)ethyl]-amino]methyl]phenyl]-2E-2-propenamide and N-hydroxy-3-[4-[[[2-(2-methyl-1H-indol-3-yl)-ethyl]-amino]methyl]phenyl]-2E-2-propenamide, or a pharmaceutically acceptable salt thereof, are important compounds of formula (Ie).

The present invention further relates to the compounds of the formula (If):

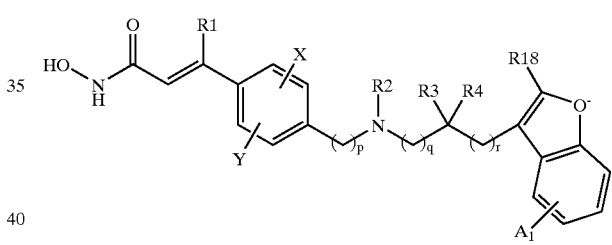

or a pharmaceutically acceptable salt thereof. The variable substituents are as defined above.

Useful compounds of formula (If) are include those wherein $R_2$ is H, or —(CH$_2$)$_p$CH$_2$OH, wherein p is 1–3, especially those wherein $R_1$ is H; such as those wherein $R_1$ is H and X and Y are X each H, and wherein q is 1–3 and r is 0 or wherein q is 0 and r is 1–3. Among these compounds $R_2$ is preferably H or —CH$_2$—CH$_2$—OH and the sum of q and r is preferably 1.

N-hydroxy-3-[4-[[[2-(benzofur-3-yl)-ethyl]-amino]methyl]phenyl]-2E-2-propenamide, or a pharmaceutically acceptable salt thereof, is an important compound of formula (If).

The compounds described above are often used in the form of a pharmaceutically acceptable salt. Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts. Acid addition salts include inorganic acid addition salts such as hydrochloride, sulfate and phosphate, and organic acid addition salts such as alkyl sulfonate, arylsulfonate, acetate, maleate, fumarate, tartrate, citrate and lactate. Examples of metal salts are alkali metal salts, such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

As is evident to those skilled in the art, the many of the deacetylase inhibitor compounds of the present invention contain asymmetric carbon atoms. It should be understood, therefore, that the individual stereoisomers are contemplated as being included within the scope of this invention.

The hydroxamate compounds of the present invention can be produced by known organic synthesis methods. For example, the hydroxamate compounds can be produced by reacting methyl 4-formyl cinnamate with tryptamine and then converting the reactant to the hydroxamate compounds. As an example, methyl 4-formyl cinnamate 2, is prepared by acid catalyzed esterification of 4-formylcinnamic acid 3 (Bull. Chem. Soc. Jpn. 1995; 68:2355–2362). An alternate preparation of methyl 4-formyl cinnamate 2 is by a Pd-catalyzed coupling of methyl acrylate 4 with 4-bromobenzaldehyde 5.

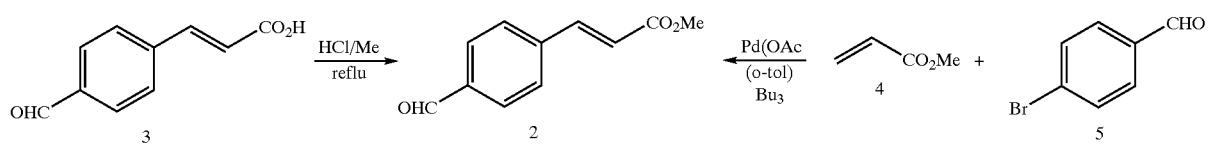

Additional starting materials can be prepared from 4-carboxybenzaldehyde 6, and an exemplary method is illustrated for the preparation of aldehyde 9, shown below. The carboxylic acid in 4-carboxybenzaldehyde 6 can be protected as a silyl ester (e.g., the t-butyldimethylsilyl ester) by treatment with a silyl chloride (e.g., t-butyldimethylsilyl chloride) and a base (e.g. triethylamine) in an appropriate solvent (e.g., dichloromethane). The resulting silyl ester 7 can undergo an olefination reaction (e.g., a Horner-Emmons olefination) with a phosphonate ester (e.g., triethyl 2-phosphonopropionate) in the presence of a base (e.g., sodium hydride) in an appropriate solvent (e.g., tetrahydrofuran (THF)). Treatment of the resulting diester with acid (e.g., aqueous hydrochloric acid) results in the hydrolysis of the silyl ester providing acid 8. Selective reduction of the carboxylic acid of 8 using, for example, borane-dimethylsuflide complex in a solvent (e.g., THF) provides an intermediate alcohol. This intermediate alcohol could be oxidized to aldehyde 9 by a number of known methods, including, but not limited to, Swern oxidation, Dess-Martin periodinane oxidation, Moffatt oxidation and the like.

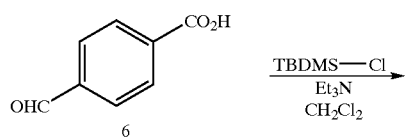

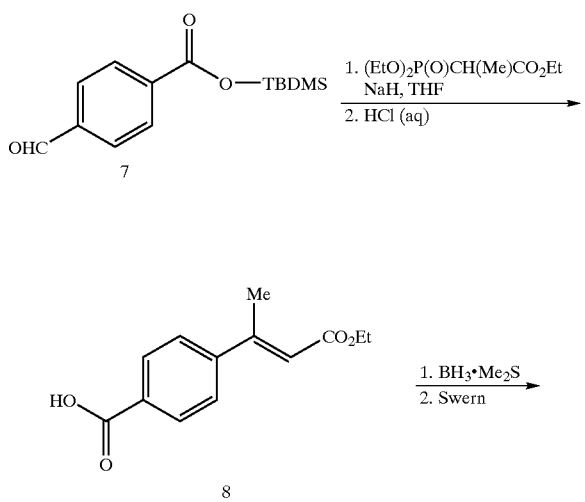

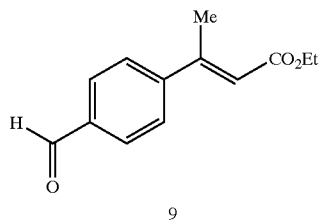

The aldehyde starting materials 2 or 9 can be reductively aminated to provide secondary or tertiary amines. This is illustrated by the reaction of methyl 4-formyl cinnamate 2 with tryptamine 10 using sodium triacetoxyborohydride (NaBH(OAc)$_3$) as the reducing agent in dichloroethane (DCE) as solvent to provide amine 11. Other reducing agents can be used, e.g., sodium borohydride (NaBH$_4$) and sodium cyanoborohydride (NaBH$_3$CN), in other solvents or solvent mixtures in the presence or absence of acid catatylysts (e.g., acetic acid and trifluoroacetic acid). Amine 11 can be converted directly to hydroxamic acid 12 by treatment with 50% aqueous hydroxylamine in a suitable solvent (e.g., THF in the presence of a base, e.g., NaOH). Other methods of hydroxamate formation are known and include reaction of an ester with hydroxylamine hydrochloride and a base (e.g., sodium hydroxide or sodium methoxide) in a suitable solvent or solvent mixture (e.g., methanol, ethanol or methanol/THF).

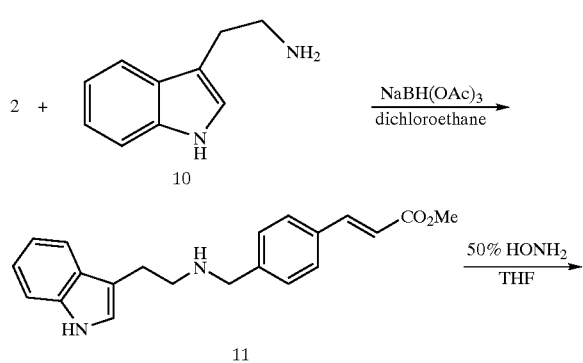
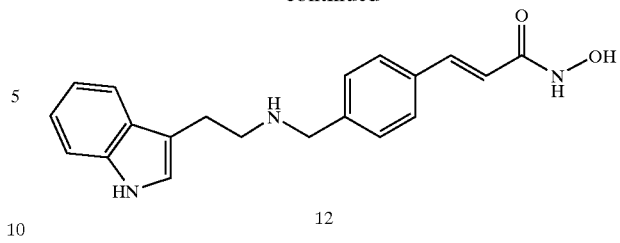

Aldehyde 2 can be reductively aminated with a variety of amines, exemplified by, but not limited to, those illustrated in Table 1. The resulting esters can be converted to target hydroxamates by the methods listed.

TABLE 1

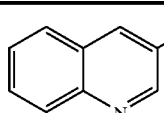

| Amine | Reducing Conditions | Hydroxamate Conditions | R |
|---|---|---|---|
| 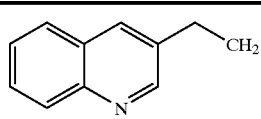 | NaBH(OAc)₃ HOAc, DCE | 2M HONH₂ in MeOH | 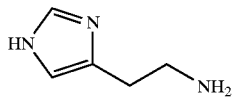 |
| 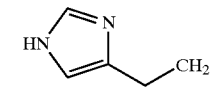 | NaBH(OAc)₃ HOAc, DCE | 2M HONH₂ in MeOH | 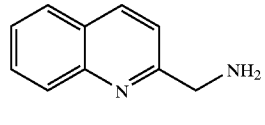 |
| 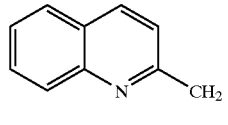 | NaBH(OAc)₃ HOAc, DCE | 2M HONH₂ in MeOH | 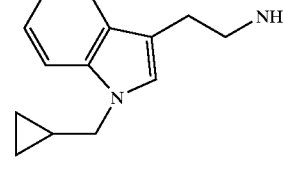 |
| 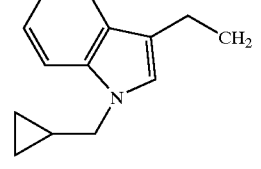 | NaBH(OAc)₃ HOAc, DCE | 2M HONH₂ in MeOH | 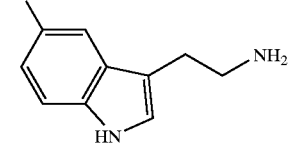 |
| 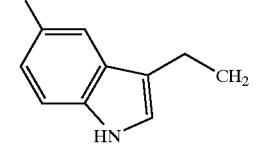 | NaBH(OAc)₃ HOAc, DCE | 2M HONH₂ in MeOH | 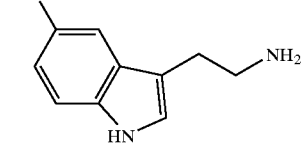 |
| 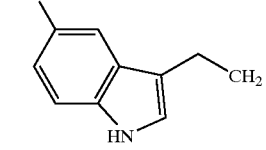 | NaBH(OAc)₃ HOAc, DCE | 2M HONH₂ in MeOH | |

TABLE 1-continued

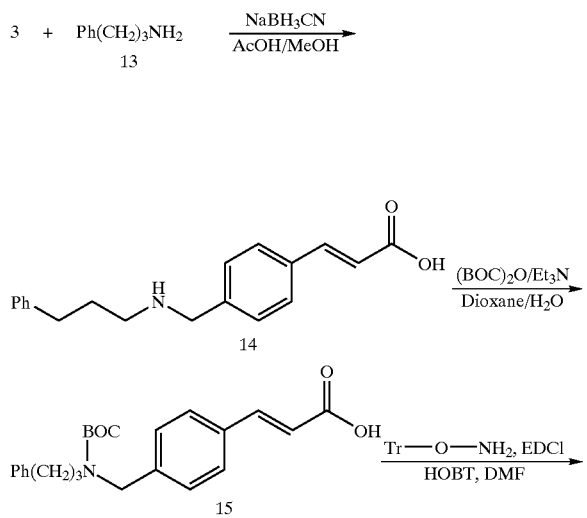

| Amine | Reducing Conditions | Hydroxamate Conditions | R |
|---|---|---|---|
| (8-sulfonamidoquinoline ethylamine) | NaBH(OAc)₃ HOAc, DCE | 2M HONH₂ in MeOH | (8-sulfonamidoquinoline ethyl) |
| (N-methyl tryptamine) | NaBH(OAc)₃ HOAc, DCE | 2M HONH₂ in MeOH | (N-methyl indol-3-yl ethyl) |
| (N-carbazolyl ethylamine) | NaBH(OAc)₃ HOAc, DCE | 2M HONH₂ in MeOH | (N-carbazolyl ethyl) |
| Ph(CH₂)₃NH₂ | NaBH₃CN/MeOH/ HOAc | | Ph(CH₂)₃ |

An alternate synthesis of the compounds of this invention starts by reductive amination of 4-formyl cinnamic acid 3, illustrated below with 3-phenylpropylamine 13, using, for example, NaBH₃CN as the reducing agent in MeOH and HOAc as a catalyst. The basic nitrogen of the resulting amino acid 14 can be protected, for example, as t-butoxycarbamate (BOC) by reaction with di-t-butyldicarbonate to give 15.

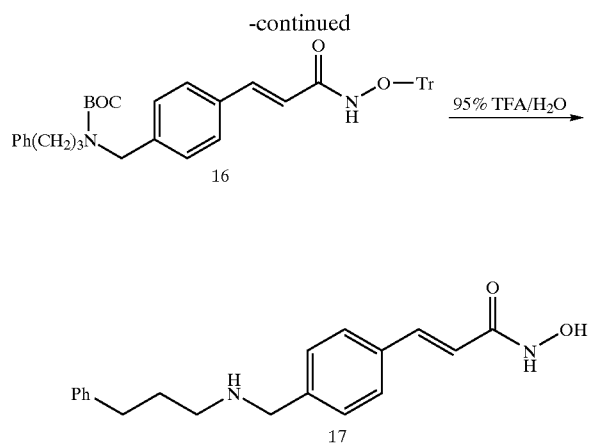

The carboxylic acid can be coupled with a protected hydroxylamine (e.g., O-trityl hydroxylamine) using a dehydrating agent (e.g., 1-(3-dimethylaminopropyl)-3ethylcarbodiimide hydrochloride (EDCI)) and a catalyst (e.g., 1-hydroxybenzotriazole hydrate (HOBT)) in a suitable solvent (e.g., DMF) to produce 16. Treatment of 16 with a strong acid (e.g., trifluoroacetic acid (TFA)) provides a hydroxamic acid 17 of the present invention. Additional examples of compounds that can be prepared by this method are:

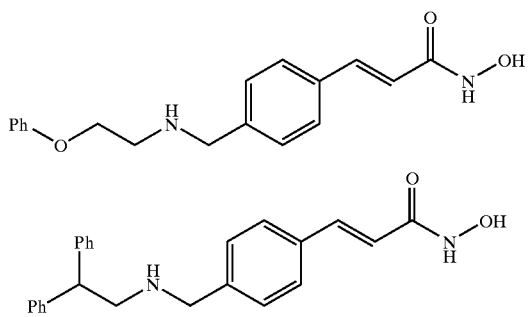

Tertiary amine compounds can be prepared by a number of methods. Reductive amination of 30 with nicotinaldehyde 32 using NaBH₃CN as the reducing agent in dichloroethane and HOAc as a catalyst provides ester 34. Other reducing agents can be used (e.g., NaBH$_4$ and NaBH(OAc)$_3$) in other solvents or solvent mixtures in the presence or absence of acid catalysts (e.g., acetic acid, trifluoroacetic acid and the like). Reaction of ester 34 with HONH$_2$.HCl, NaOH in MeOH provides hydroxamate 36.

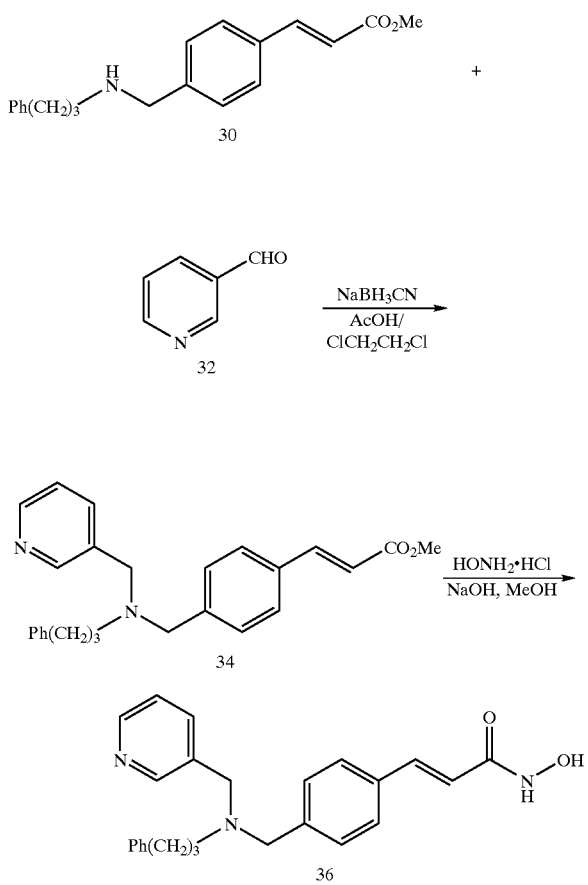

Tertiary amine compounds prepared by this methodology are exemplified, but not limited to, those listed in Table 2.

TABLE 2

| | Reducing Conditions | Hydroxamate Conditions |
|---|---|---|
| 4-pyridyl-CH₂ | NaBH(OAc)₃ HOAc, DCE | HONH₂.HCl/ NaOMe/MeOH |
| 2-pyridyl-CH₂ | NaBH(OAc)₃ HOAc, DCE | HONH₂.HCl/ NaOMe/MeOH |
| 4-quinolinyl-CH₂ | NaBH(OAc)₃ HOAc, DCE | 2M HONH₂ in MeOH |
| 3-quinolinyl-CH₂ | NaBH₃CN/MeOH/ HOAc | 2M HONH₂ in MeOH |
| 4-imidazolyl-CH₂ | NaBH(OAc)₃ HOAc, DCE | 2M HONH₂ in MeOH |

An alternate method for preparing tertiary amines is by reacting a secondary amine with an alkylating agent in a suitable solvent in the presence of a base. For example, heating a dimethylsulfoxide (DMSO) solution of amine 11 and bromide 40 in the presence of (i-Pr)$_2$NEt yielded tertiary amine 42. Reaction of the tertiary amine 42 with HONH$_2$.HCl, NaOH in MeOH provides hydroxamate 43. The silyl group can be removed by any method known to those skilled in the art. For example, the hydroxamate 43 can be treated with an acid, e.g., trifluoroacetic acid, or fluoride to produce hydroxyethyl compound 44.

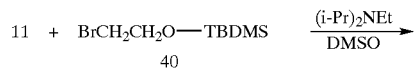

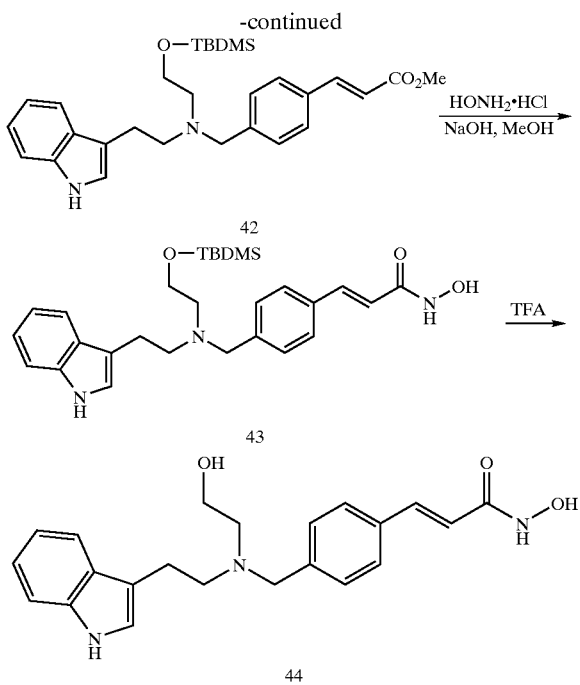

The hydroxamate compound, or salt thereof, is suitable for preparing pharmaceutical compositions, especially pharmaceutical compositions having deacetylase, especially histone deacetylase, inhibiting properties. Studies with athymic mice demonstrate that the hydroxamate compound causes HDA inhibition and increased histone acetylation in vivo, which triggers changes in gene expression that correlate with tumor growth inhibition.

The present invention further includes pharmaceutical compositions comprising a pharmaceutically effective amount of one or more of the above-described compounds as active ingredient. Pharmaceutical compositions according to the invention are suitable for enteral, such as oral or rectal, and parenteral administration to mammals, including man, for the treatment of tumors, alone or in combination with one or more pharmaceutically acceptable carriers.

The hydroxamate compound is useful in the manufacture of pharmaceutical compositions having an effective amount the compound in conjunction or admixture with excipients or carriers suitable for either enteral or parenteral application. Preferred are tablets and gelatin capsules comprising the active ingredient together with (a) diluents; (b) lubricants, (c) binders (tablets); if desired, (d) disintegrants; and/or (e) absorbents, colorants, flavors and sweeteners. Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. The compositions are prepared according to conventional mixing, granulating or coating methods, respectively, and contain preferably about 1 to 50% of the active ingredient.

Suitable formulations also include formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

As discussed above, the compounds of the present invention are useful for treating proliferative diseases. A proliferative disease is mainly a tumor disease (or cancer) (and/or any metastases). The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multidrug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original ,organ or tissue and/or in any other location are implied alternatively or in addition, whatever the location of the tumor and/or metastasis.

The compound is selectively toxic or more toxic to rapidly propiferating cells than to normal cells, particularly in human cancer cells, e.g., cancerous tumors, the compound has significant antiproliferative effects and promotes differentiation, e.g., cell cycle arrest and apoptosis. In addition, the hydroxamate compound induces p21, cyclin-CDK interacting protein, which induces either apoptosis or G1 arrest in a variety of cell lines.

The following examples are intended to illustrate the invention and are not to be construed as being limitations thereto.

EXAMPLE P1

Preparation of N-Hydroxy-3-[4-[[[2-(1H-indol-3-yl)-ethyl]-amino]methyl]phenyl]-2E-2-propenamide 4-formylcinnamic acid methylester is produced by adding 4-formylcinnamic acid (25 g, 0.143 mol) in MeOH and HCl (6.7 g, 0.18 mol). The resulting suspension is heated to reflux for 3 hours, cooled and evaporated to dryness. The resulting yellow solid is dissolved in EtOAc, the solution washed with saturated $NaHCO_3$, dried ($MgSO_4$) and evaporated to give a pale yellow solid which is used without further purification (25.0 g, 92%). To a solution of tryptamine (16.3 g, 100 mmol) and 4-formylcinnamic acid methylester (19 g, 100 mmol) in dichloroethane, NaBH (OAc)$_3$ (21 g, 100 mmol) is added. After 4 hours the mixture is diluted with 10% K$_2$CO$_3$ solution, the organic phase separated and the aqueous solution extracted with CH$_2$Cl$_2$. The combined organic extracts are dried (Na$_2$SO$_4$), evaporated and the residue purified by flash chromatography to produce 3-(4-{[2-(1H-indol-3-yl)-ethylamino]-methyl}-phenyl)-(2E)-2-propenoic acid methyl ester (29 g). A solution of KOH (12.9 g 87%, 0.2 mol) in MeOH (100 mL) is added to a solution of HONH$_2$.HCl (13.9 g, 0.2 mol) in MeOH (200 mL) and a precipitate results. After 15 minutes the mixture is filtered, the filter cake washed with MeOH and the filtrate evaporated under vacuum to approximately 75 mL. The mixture is filtered and the volume adjusted to 100 mL with MeOH. The resulting solution 2M HONH$_2$ is stored under N$_2$ at −20° C. for up to 2 weeks. Then 3-(4-{[2-(1H-indol-3-yl-ethylamino]-methyl}-phenyl)-(2E)-2-propenoic acid methyl ester (2.20 g, 6.50 mmol) is added to 2 M HONH$_2$ in MeOH (30 mL, 60 mmol) followed by a solution of KOH (420 mg, 6.5 mmol) in MeOH (5 mL). After 2 hours dry ice is added to the reaction and the mixture is evaporated to dryness. The residue is dissolved in hot MeOH (20 mL), cooled and stored at −20° C. overnight. The resulting suspension is filtered, the solids washed with ice cold MeOH and dried under vacuum, producing N-Hydroxy-3-[4-[[[2-(1H-indol-3-yl)-ethyl]-amino]methyl]phenyl]-2E-2-propenamide (m/z 336 [MH$^+$]).

EXAMPLE P2

Preparation of N-Hydroxy-3-[4-[[(2-hydroxyethyl)[2-(1H-indol-3-yl)-ethyl]-amino]methyl]phenyl]-2E-2-propenamide A solution of 3-(4-{[2-(1H-indol-3-yl)-ethylamino]-methyl}-phenyl)-(2E)-2-propenoic acid methyl ester (12.6 g, 37.7 mmol), (2-bromoethoxy)-tert-butyldimethylsilane (12.8 g, 53.6 mmol), (i-Pr)$_2$NEt, (7.42 g, 57.4 mmol) in DMSO (100 mL) is heated to 50° C. After 8 hours the mixture is partitioned with CH$_2$Cl$_2$/H$_2$O. The organic layer is dried (Na$_2$SO$_4$) and evaporated. The residue is chromatographed on silica gel to produce 3-[4-({[2-(tert-butyldimethylsilanyloxy)-ethyl]-[2-(1H-indol-3-yl)-ethyl]-amino}-methyl)-phenyl]-(2E)-2-propenoic acid methyl ester (13.1 g). Following the procedure described for the preparation of the hydroxamate compound in Example P1, 3-[4-({[2-(tert-butyldimethylsilanyloxy)-ethyl]-[2-(1H-indol-3-yl)-ethyl]-amino}-methyl)-phenyl]-(2E)-2-propenoic acid methyl ester (5.4 g, 11 mmol) is converted to N-hydroxy-3-[4-({[2-(tert-butyldimethylsilanyloxy)-ethyl]-[2-(1H-indol-3-yl)-ethyl]-amino}-methyl)-phenyl]-(2E)-2-propenamide (5.1 g,) and used without further purification. The hydroxamic acid (5.0 g, 13.3 mmol) is then dissolved in 95% TFA/H$_2$O (59 mL) and heated to 40–50° C. for 4 hours. The mixture is evaporated and the residue purified by reverse phase HPLC to produce N-Hydroxy-3-[4-[[(2-hydroxyethyl)[2-(1H-indol-3-yl)-ethyl]-amino]methyl]phenyl]-2E-2-propenamide as the trifluoroacetate salt (m/z 380 [MH$^+$]).

EXAMPLE P3

Preparation of N-hydroxy-3-[4-[[[2-(2-methyl-1H-indol-3-yl)-ethyl]-amino]methyl]phenyl]-2E-2-propenamide A suspension of LiAlH$_4$ (17 g, 445 mmol) in dry THF (1000 mL) is cooled to 0° C. and 2-methylindole-3-glyoxylamide (30 g, 148 mmol) is added in portions over 30 min. The mixture is stirred at room temperature for 30 min. and then maintained at reflux for 3 h. The reaction is cooled to 0° C. and treated with H$_2$O (17 ml), 15% NaOH (aq., 17 ml) and H$_2$O (51 ml). The mixture is treated with MgSO$_4$, filtered and the filtrate evaporated to give 2-methyltryptamine which is dissolved in MeOH. Methyl 4-formylcinnamate (16.9 g, 88.8 mmol) is added to the solution, followed by NaBH$_3$CN (8.4 g) and AcOH (1 equiv.). After 1 h the reaction is diluted with NaHCO$_3$ (aq.) and extracted with EtOAc. The organic extracts are dried (MgSO$_4$), filtered and evaporated. The residue is purified by chromatography to give 3-(4-{[2-(2-methyl-1H-indol-3-yl)-ethylamino]-methyl}-phenyl)-(2E)-2-propenoic acid methyl ester. The ester is dissolved in MeOH, 1.0 M HCl/dioxane (1–1.5 eqiv.) is added followed by Et$_2$O. The resulting precipitate is filtered and the solid washed with Et$_2$O and dried thoroughly to give 3-(4-{[2-(2-methyl-1H-indol-3-yl)-ethylamino]-methyl}-phenyl)-(2 E)-2-propenoic acid methyl ester hydrochloride. 1.0 M NaOH (aq., 85 mL) is added to an ice cold solution of the methyl ester hydrochloride (14.9 g, 38.6 mmol) and HONH$_2$ (50% aq. solution, 24.0 mL, ca. 391.2 mmol). After 6 h, the ice cold solution is diluted with H$_2$O and NH$_4$Cl (aq., 0.86 M, 100 mL). The resulting precipitate is filtered, washed with H$_2$O and dried to afford N-hydroxy-3-[4-[[[2-(2-methyl-1H-indol-3-yl)-ethyl]-amino]methyl]phenyl]-2E-2-propenamide (m/z 350 [MH$^+$]).

EXAMPLES 1–265

The following compounds are prepared by methods analogous to those disclosed in Examples P1, P2 and P3:

| Example | STRUCTURE | m/z (MH$^+$) |
|---|---|---|
| 1 | 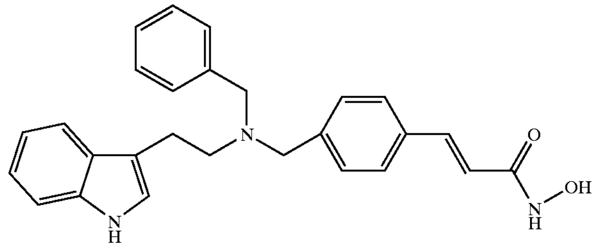 | 426 |

-continued
| Example | STRUCTURE | m/z (MH+) |
|---|---|---|
| 2 | 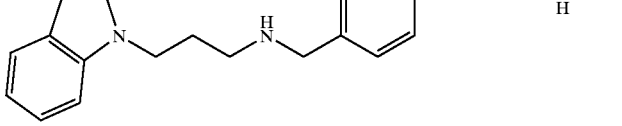 | |
| 3 | 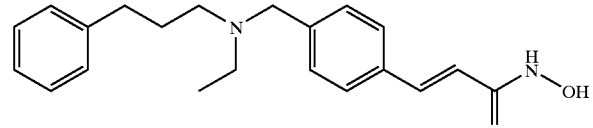 | |
| 4 | 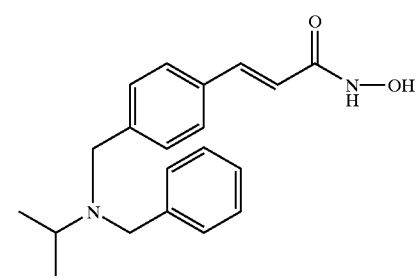 | 325 |
| 5 | 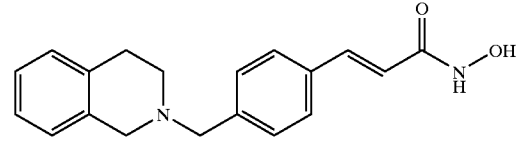 | |
| 6 | 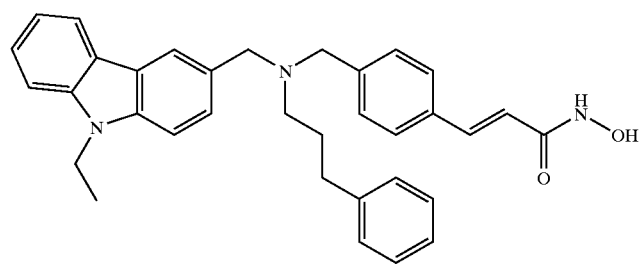 | |
| 7 | 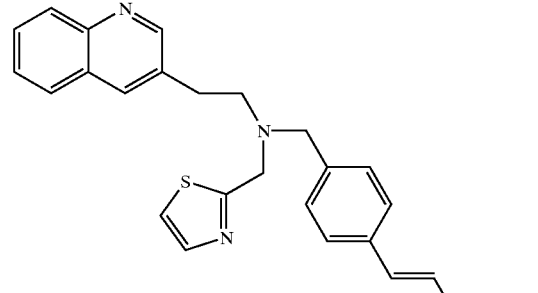 | |

-continued
| Example | STRUCTURE | m/z (MH+) |
|---|---|---|
| 8 | 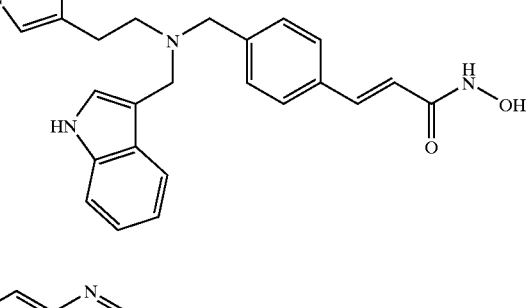 | 465 |
| 9 | 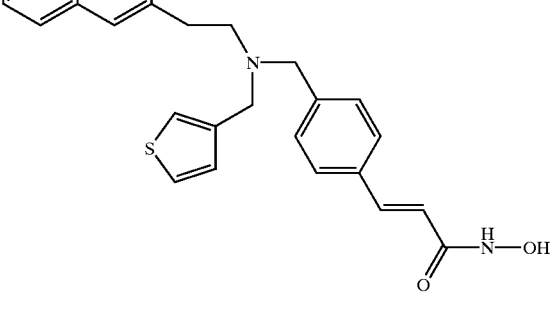 | |
| 10 | 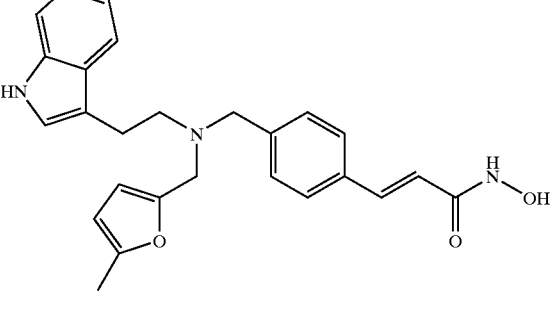 | |
| 11 | 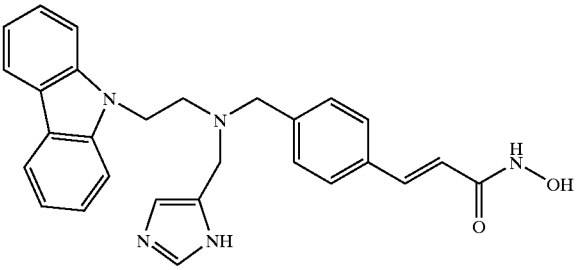 | |

-continued

| Example | STRUCTURE | m/z (MH+) |
|---|---|---|
| 12 | 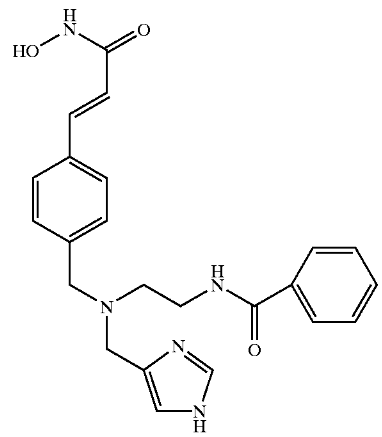 | 420 |
| 13 | 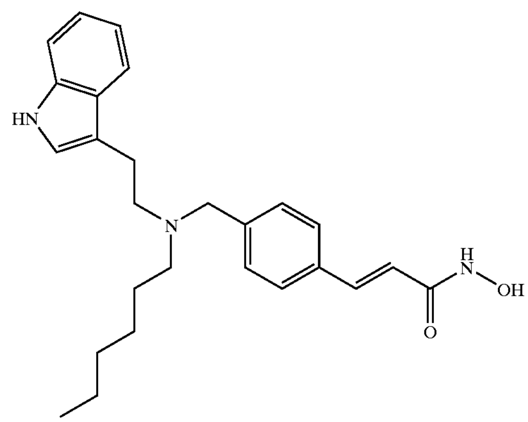 | 420 |
| 14 | 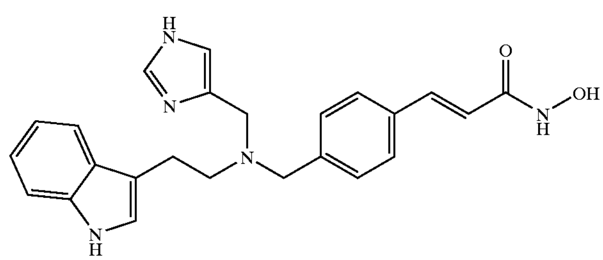 | 420 |
| 15 | 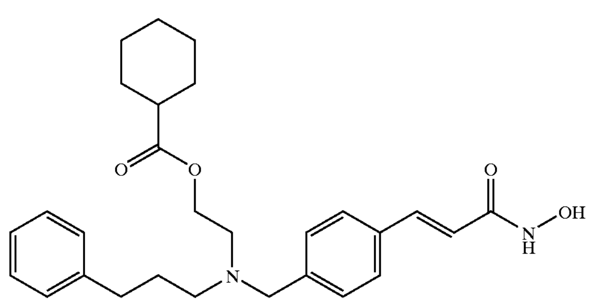 | 465 |

-continued

| Example | STRUCTURE | m/z (MH+) |
|---|---|---|
| 16 | (structure) | 385 |
| 17 | (structure) | 550 |
| 18 | (structure) | 432 |
| 19 | (structure) | 366 |
| 20 | (structure) | 350 |

-continued
| Example | STRUCTURE | m/z (MH+) |
|---|---|---|
| 21 | 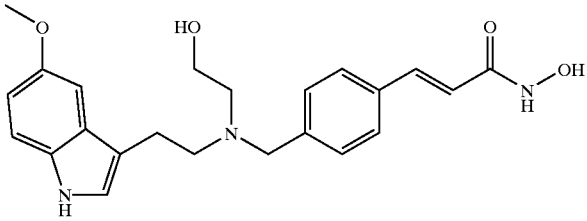 | |
| 22 | 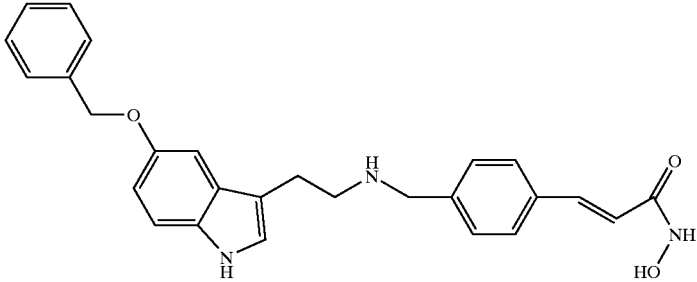 | 442 |
| 23 | 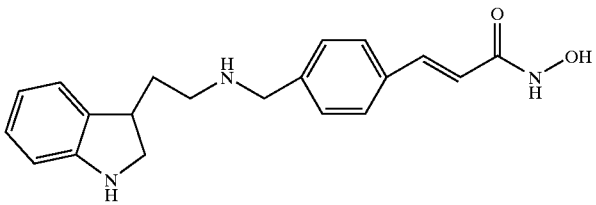 | 338 |
| 24 | 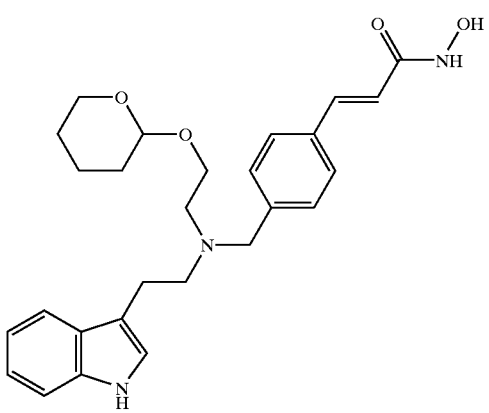 | 464 |
| 25 | 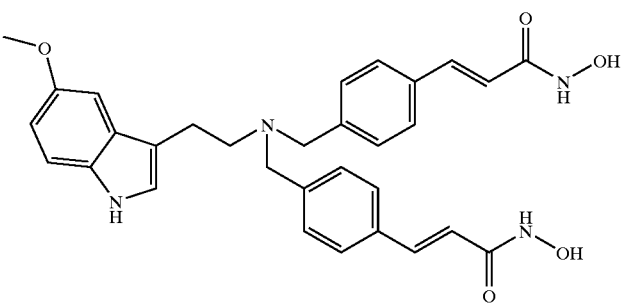 | 541 |

-continued

| Example | STRUCTURE | m/z (MH+) |
|---|---|---|
| 26 | 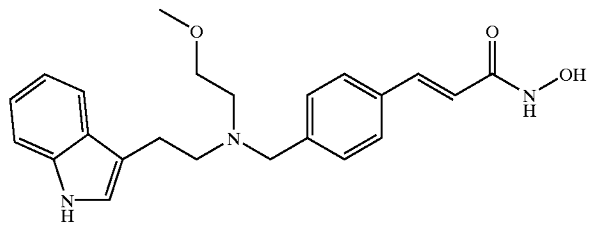 | |
| 27 | 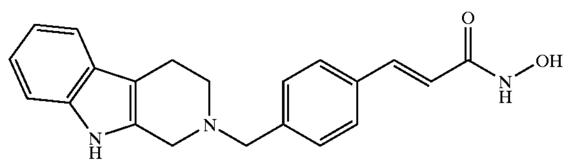 | |
| 28 | 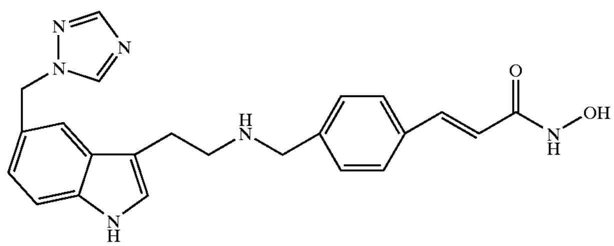 | 417 |
| 29 | 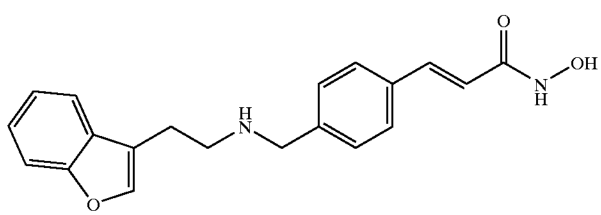 | |
| 30 | 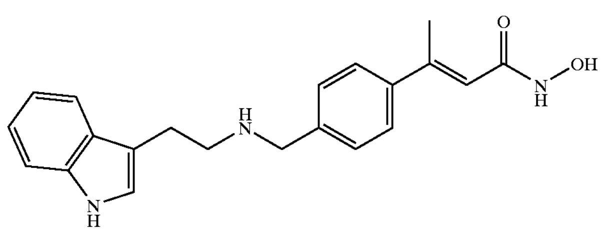 | |
| 31 | 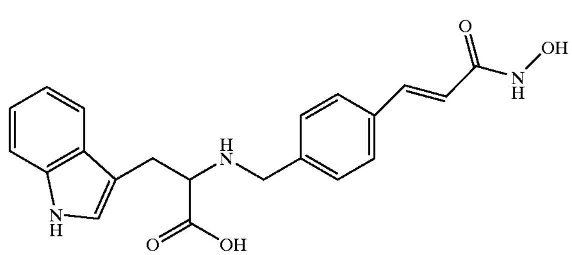 | 380 |

-continued
| Example | STRUCTURE | m/z (MH+) |
|---|---|---|
| 32 | 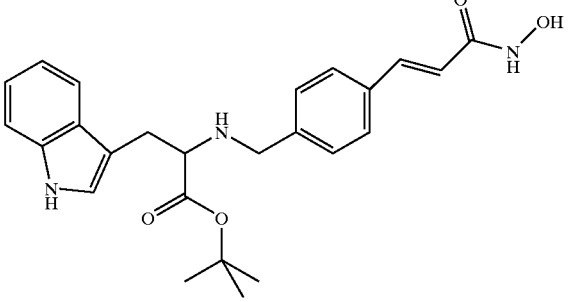 | 436 |
| 33 | 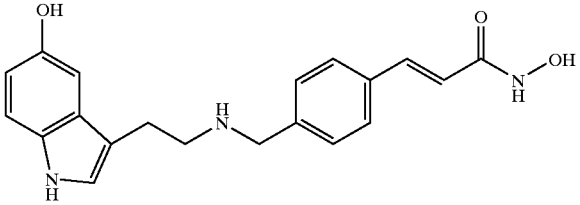 | |
| 34 | 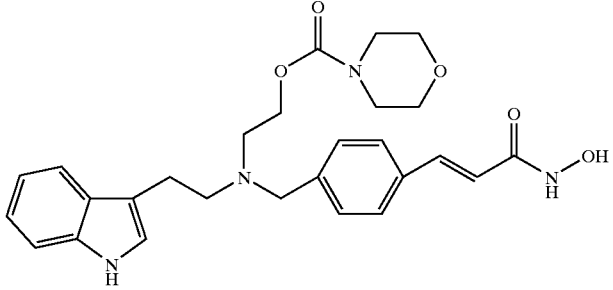 | 493 |
| 35 | 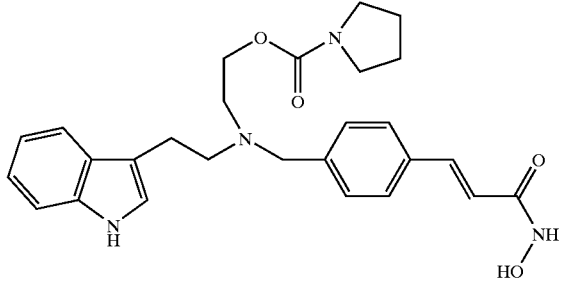 | 477 |
| 36 | 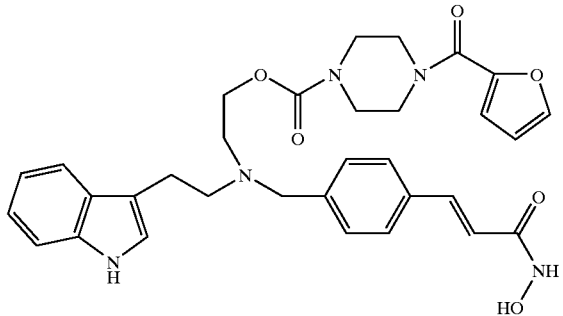 | 586 |

-continued

| Example | STRUCTURE | m/z (MH+) |
|---|---|---|
| 37 | 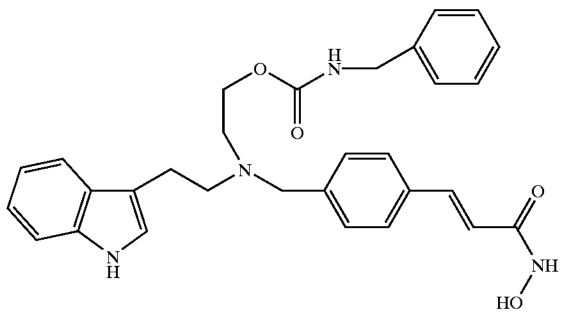 | 513 |
| 38 | 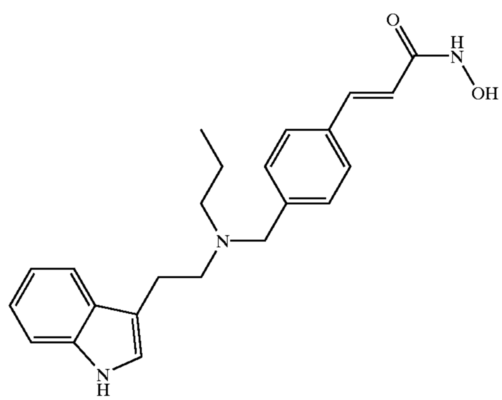 | 378 |
| 39 | 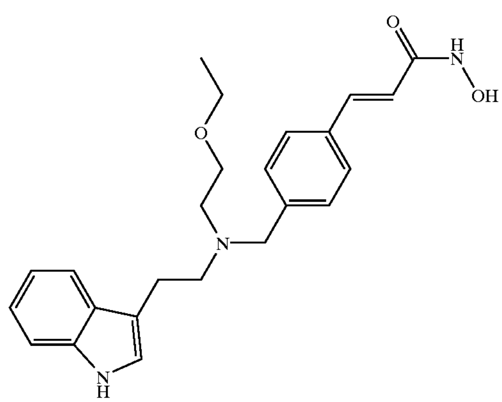 | 408 |
| 40 | 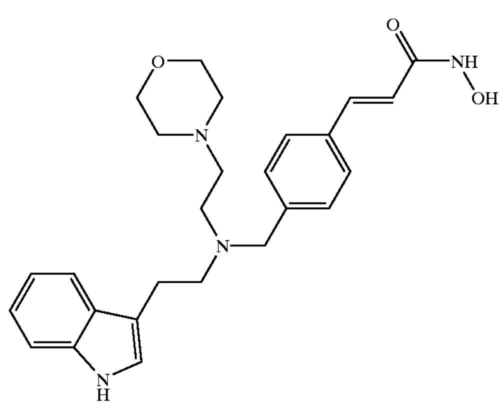 | 449 |

-continued
| Example | STRUCTURE | m/z (MH+) |
|---|---|---|
| 41 | 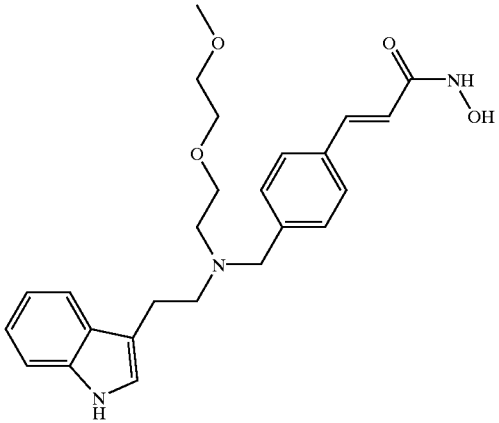 | 438 |
| 42 | 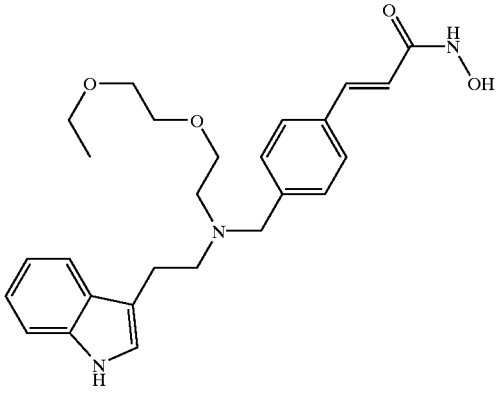 | 452 |
| 43 | 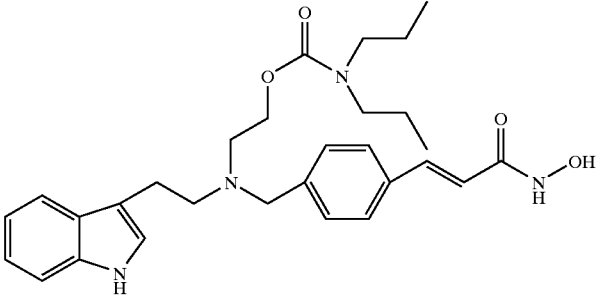 | 507 |
| 44 | 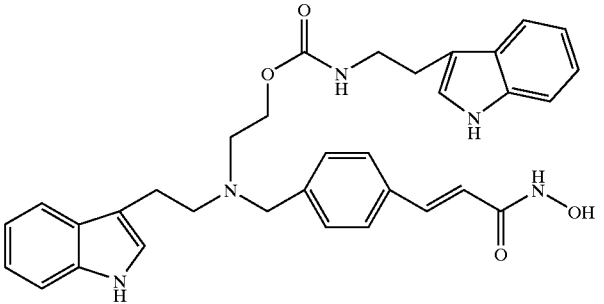 | 565 |

| Example | STRUCTURE | m/z (MH+) |
|---|---|---|
| 45 | 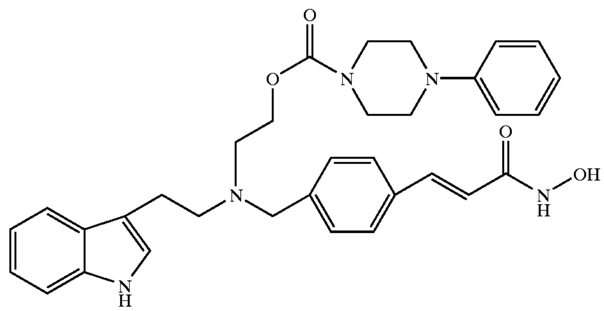 | |
| 46 | 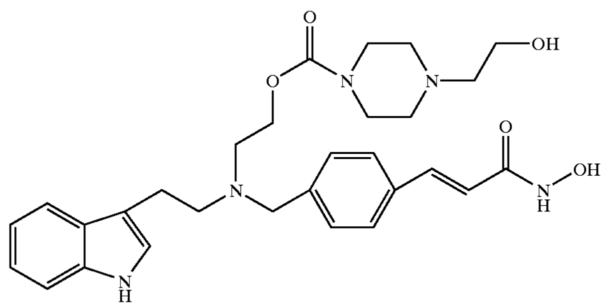 | |
| 47 | 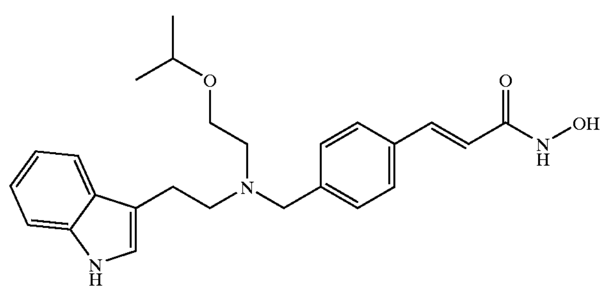 | |
| 48 | 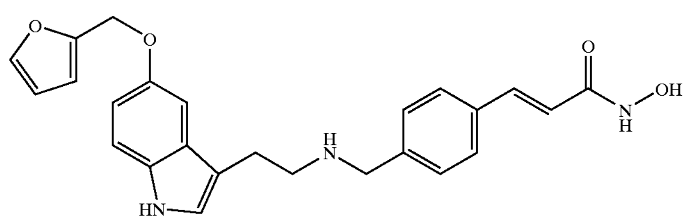 | |
| 49 | 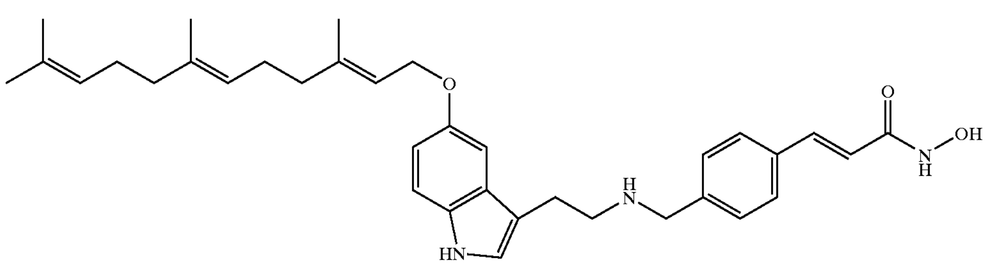 | |

-continued
| Example | STRUCTURE | m/z (MH+) |
|---|---|---|
| 50 | 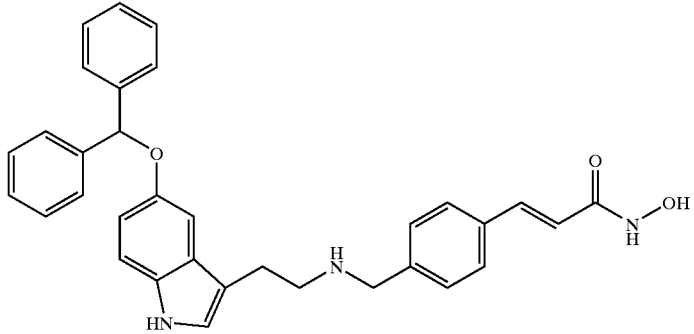 | |
| 51 | 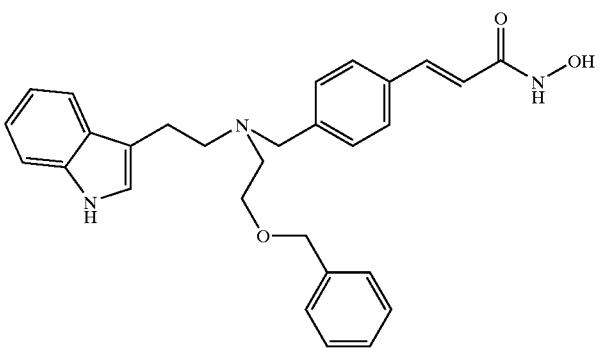 | 470 |
| 52 | 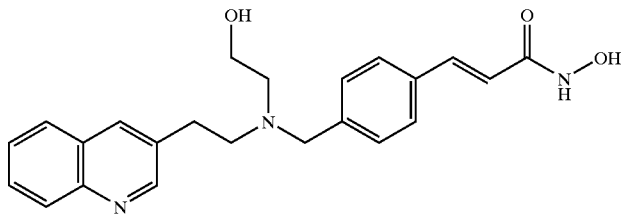 | |
| 53 | 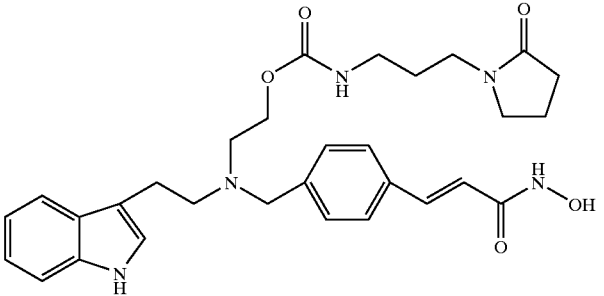 | 548 |

-continued

| Example | STRUCTURE | m/z (MH+) |
|---|---|---|
| 54 | 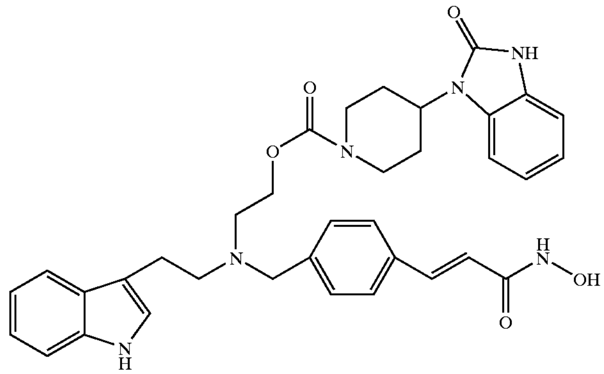 | 623 |
| 55 | 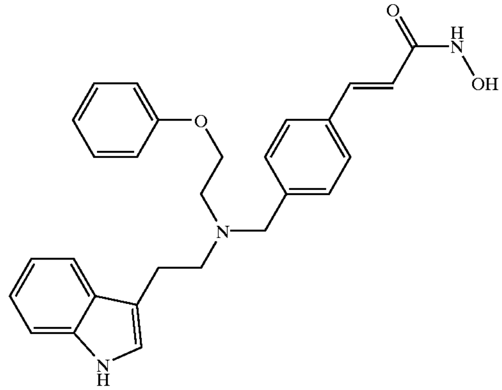 | 456 |
| 56 | 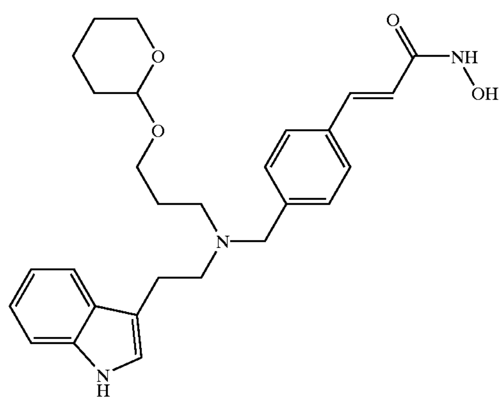 | 478 |
| 57 | 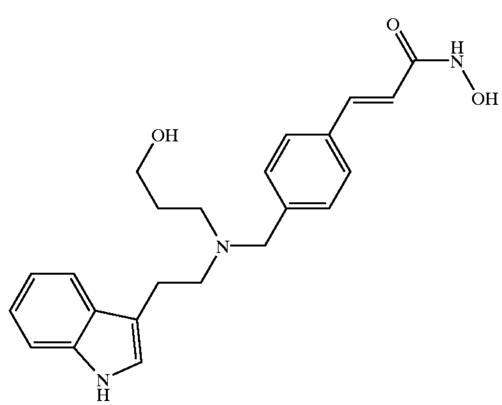 | 394 |

-continued
| Example | STRUCTURE | m/z (MH+) |
|---|---|---|
| 58 | 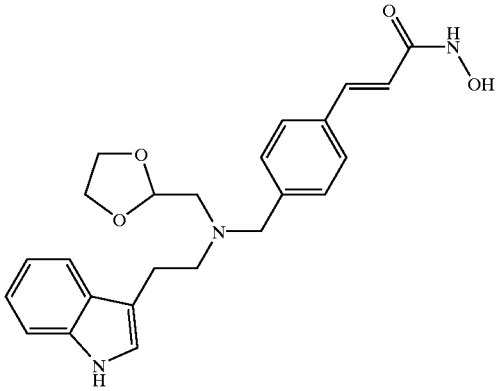 | 422 |
| 59 | 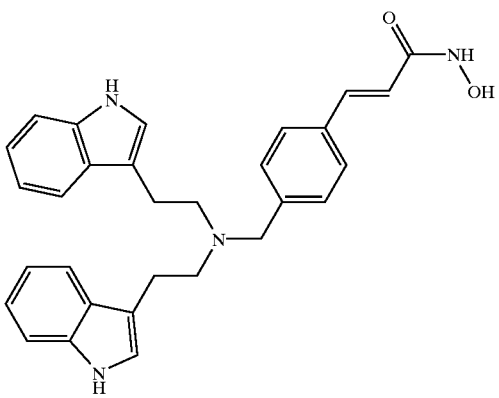 | 479 |
| 60 | 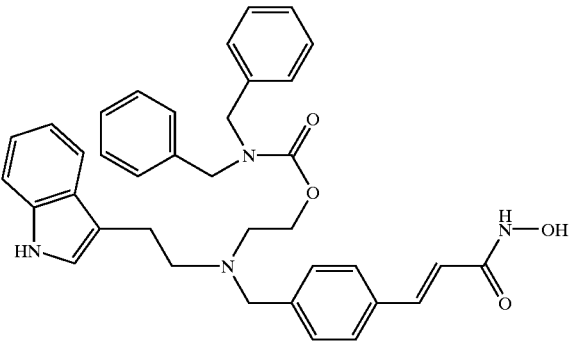 | 603 |

-continued
| Example | STRUCTURE | m/z (MH+) |
|---|---|---|
| 61 | 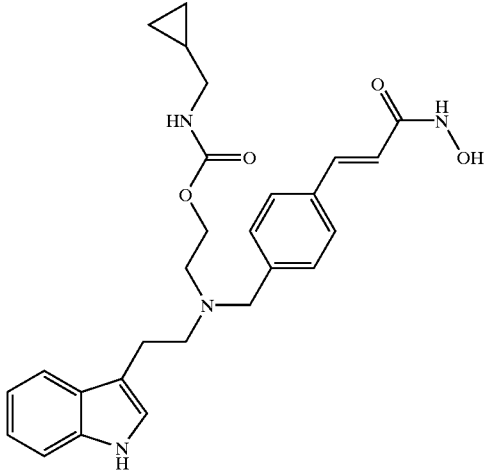 | 477 |
| 62 | 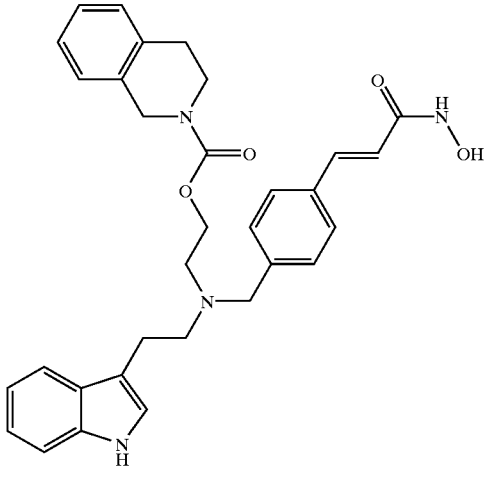 | 539 |
| 63 | 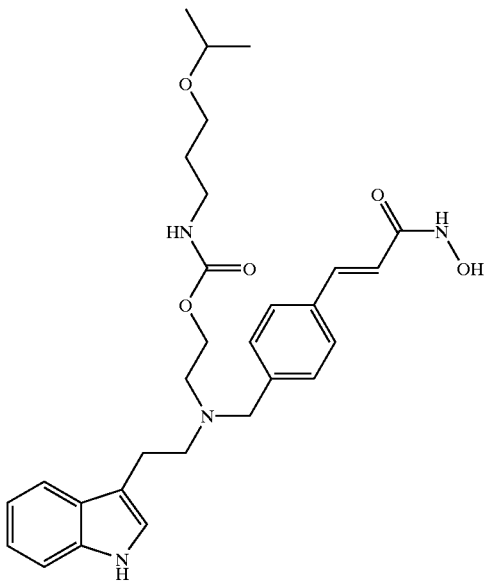 | 523 |

-continued

| Example | STRUCTURE | m/z (MH+) |
|---|---|---|
| 64 | indol-1-yl-CH2CH2-NH-CH2-C6H4-CH=CH-C(O)NHOH | |
| 65 | 4-methoxybenzyloxy-5-indol-3-yl-CH2CH2-NH-CH2-C6H4-CH=CH-C(O)NHOH | |
| 66 | indol-3-yl-CH2CH2-N(COCH3)-CH2-C6H4-CH=CH-C(O)NHOH | |
| 67 | indol-3-yl-piperidin-1-yl-CH2-C6H4-CH=CH-C(O)NHOH | |
| 68 | indol-3-yl-CH2CH2-N(CH2CH2-O-C(O)-N(CH2CH2OCH3)2)-CH2-C6H4-CH=CH-C(O)NHOH | 539 |
| 69 | indol-3-yl-CH2CH2-N(CH2CH2-O-C(O)-NH-CH2CH2CH2OCH3)-CH2-C6H4-CH=CH-C(O)NHOH | 495 |

-continued

| Example | STRUCTURE | m/z (MH+) |
|---|---|---|
| 70 | 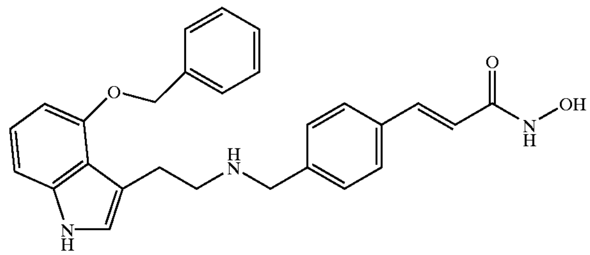 | |
| 71 | 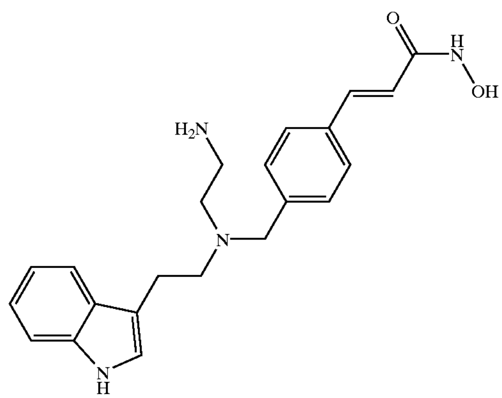 | 379 |
| 72 | 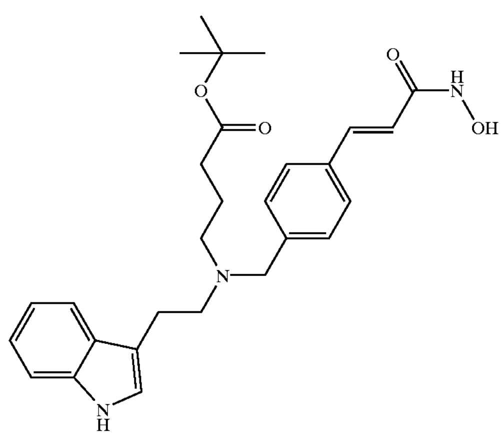 | 478 |
| 73 | 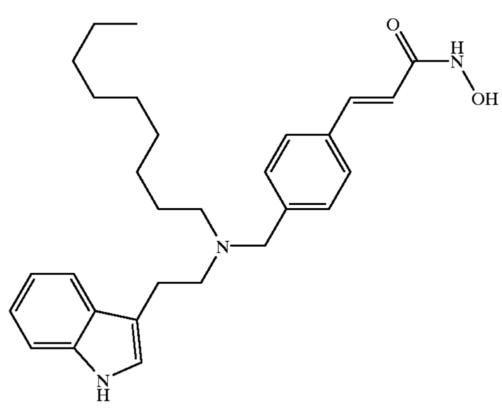 | 462 |

-continued

| Example | STRUCTURE | m/z (MH+) |
|---|---|---|
| 74 | 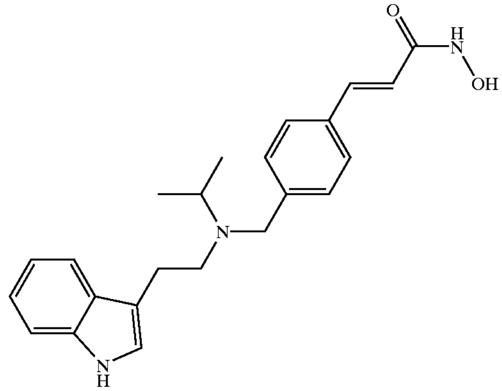 | 378 |
| 75 | 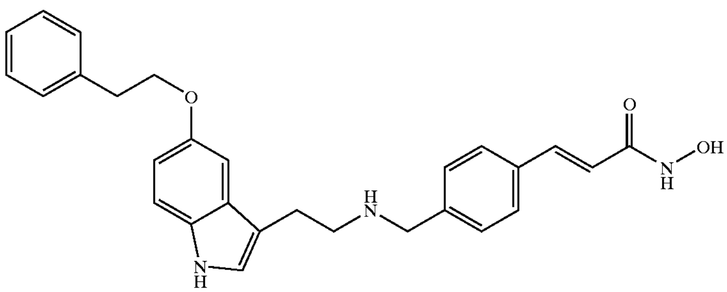 | |
| 76 | 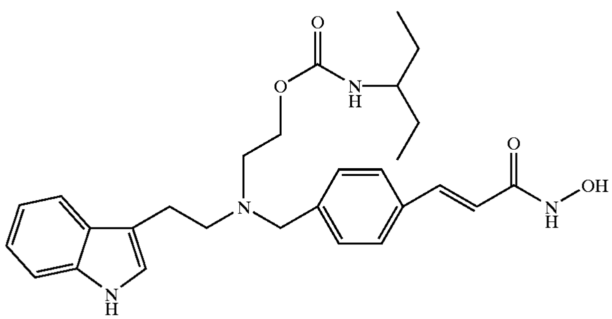 | 493 |
| 77 | 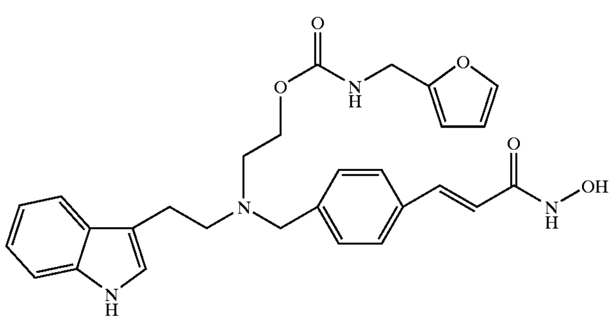 | 503 |
| 78 | 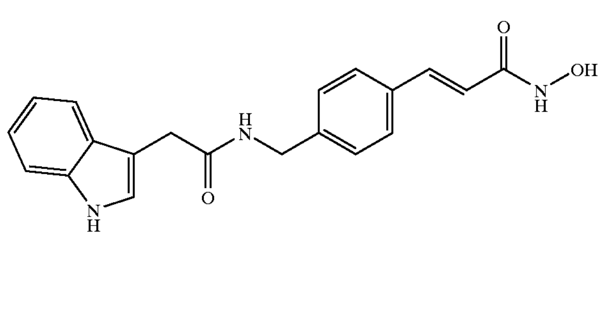 | 350 |

-continued

| Example | STRUCTURE | m/z (MH+) |
|---|---|---|
| 79 | 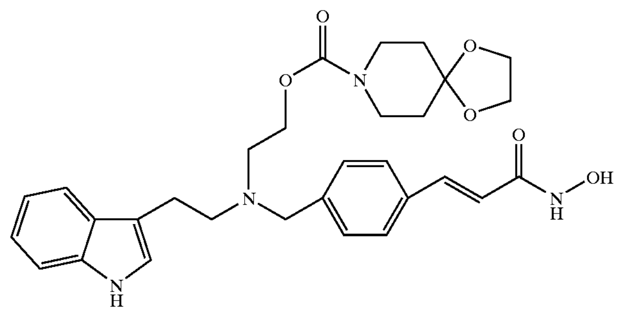 | 549 |
| 80 | 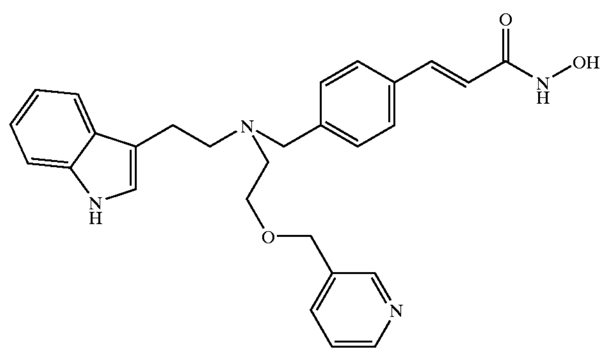 | 471 |
| 81 | 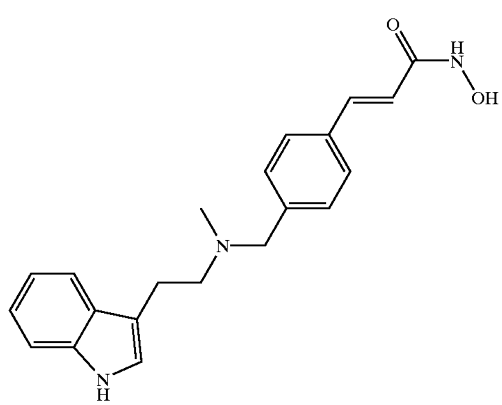 | 350 |
| 82 | 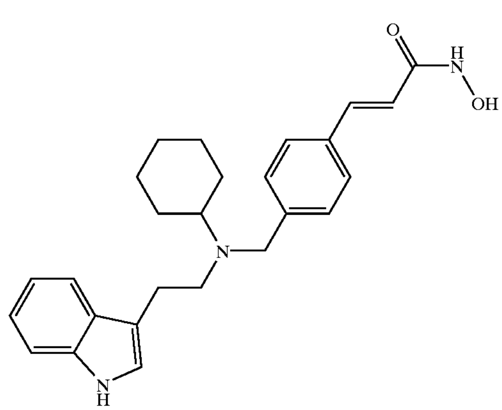 | 418 |

-continued

| Example | STRUCTURE | m/z (MH+) |
|---|---|---|
| 83 | 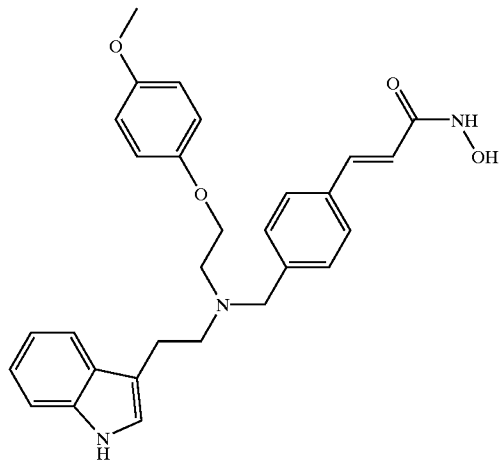 | 486 |
| 84 | 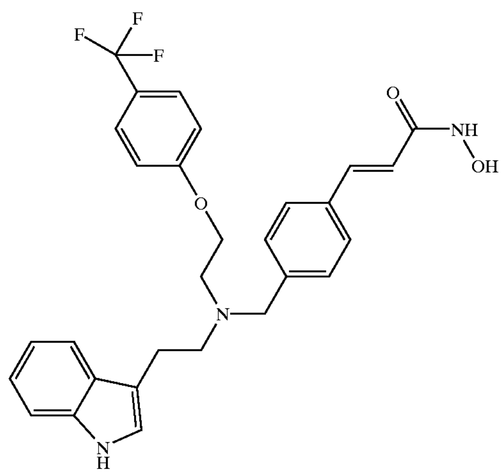 | 524 |
| 85 | 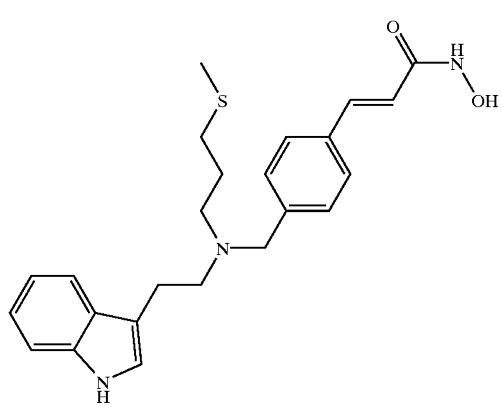 | 424 |

-continued

| Example | STRUCTURE | m/z (MH+) |
|---------|-----------|-----------|
| 86 | 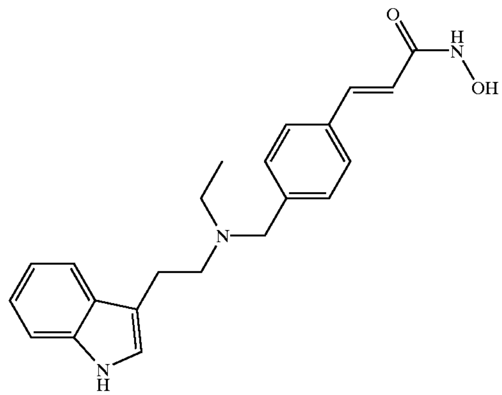 | 364 |
| 87 | 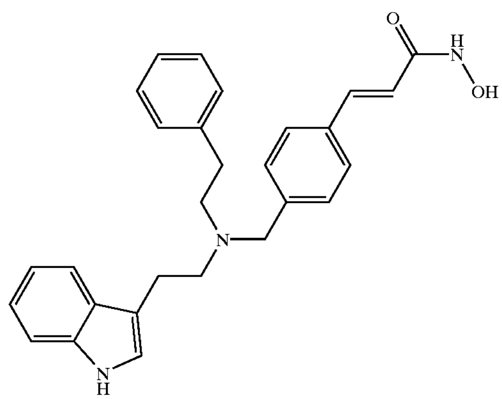 | 440 |
| 88 | 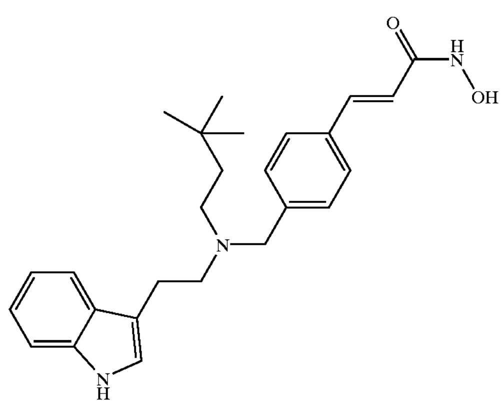 | 420 |

-continued

| Example | STRUCTURE | m/z (MH+) |
|---|---|---|
| 89 | 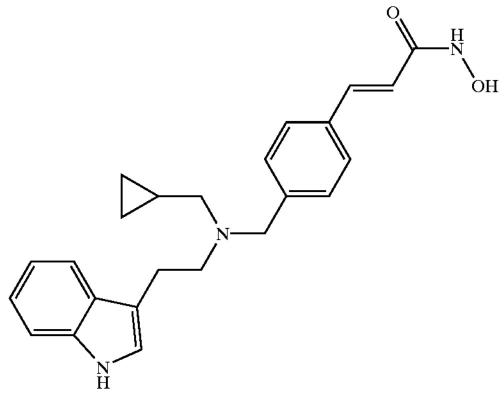 | 390 |
| 90 | 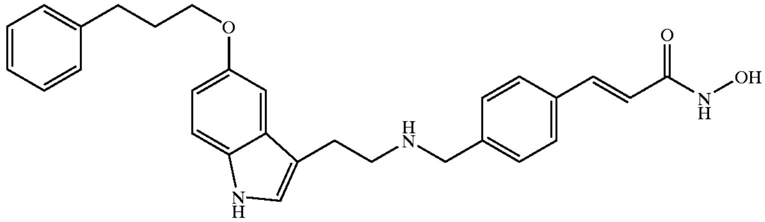 | |
| 91 | 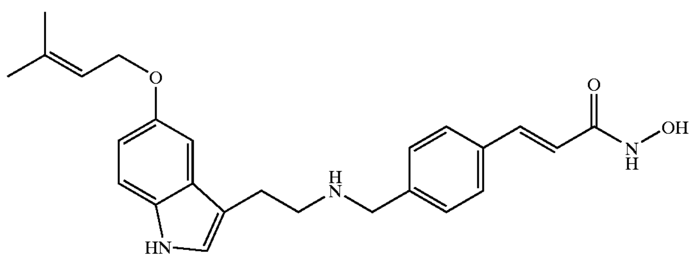 | |
| 92 | 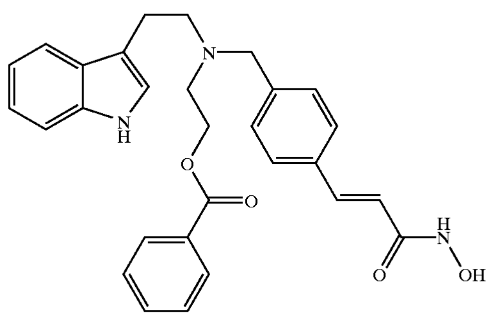 | 484 |
| 93 | 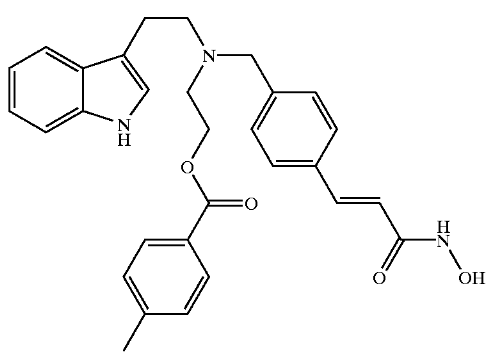 | 498 |

-continued
| Example | STRUCTURE | m/z (MH+) |
|---|---|---|
| 94 | 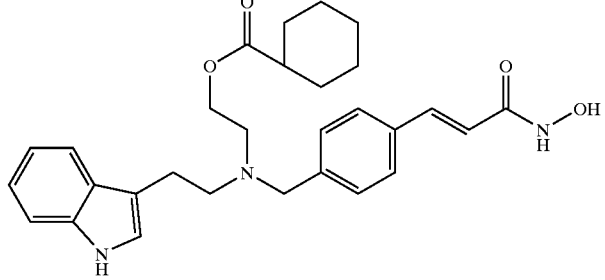 | 490 |
| 95 | 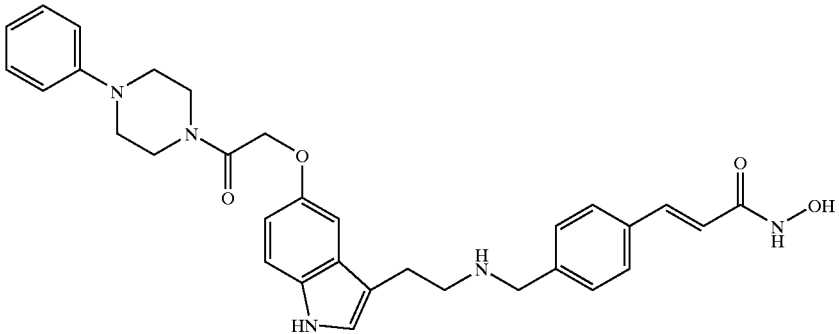 | |
| 96 | 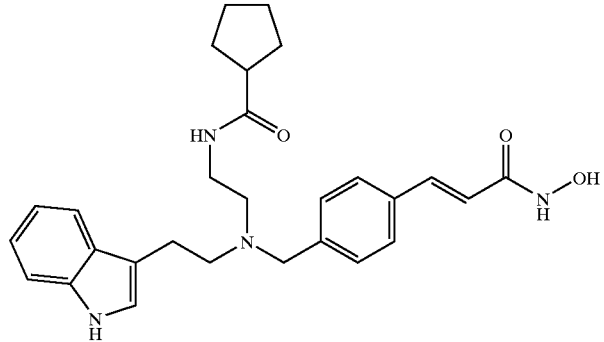 | 475 |

-continued
| Example | STRUCTURE | m/z (MH+) |
|---|---|---|
| 97 | 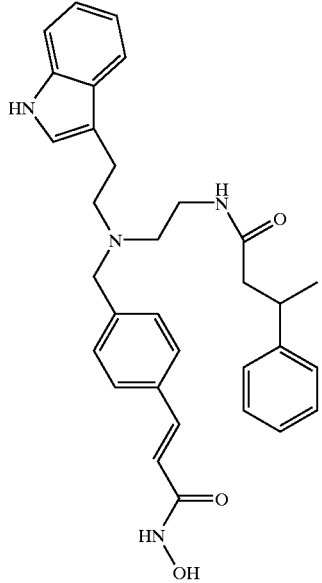 | 525 |
| 98 | 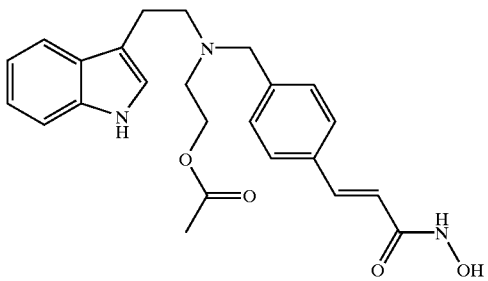 | 422 |
| 99 | 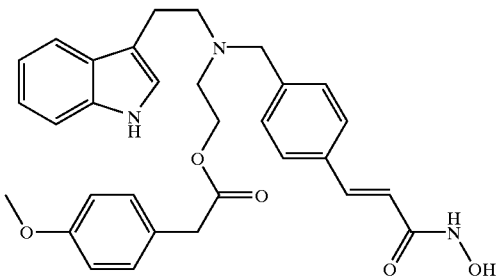 | 528 |
| 100 | 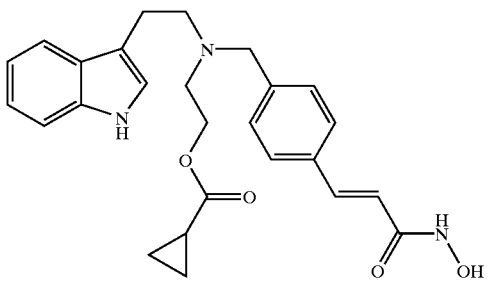 | 448 |

-continued
| Example | STRUCTURE | m/z (MH+) |
|---|---|---|
| 101 | 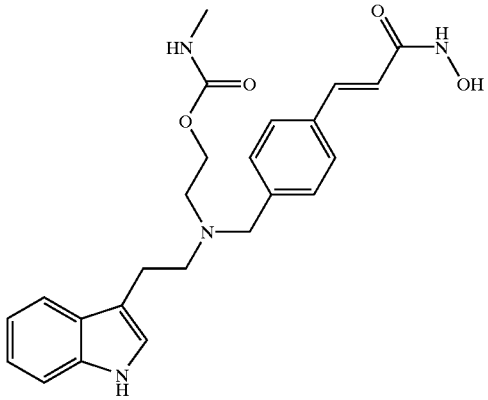 | 437 |
| 102 | 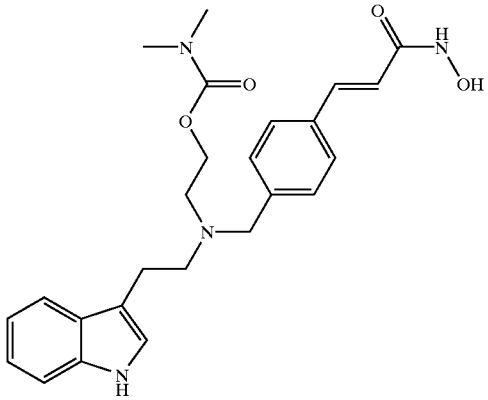 | 451 |
| 103 | 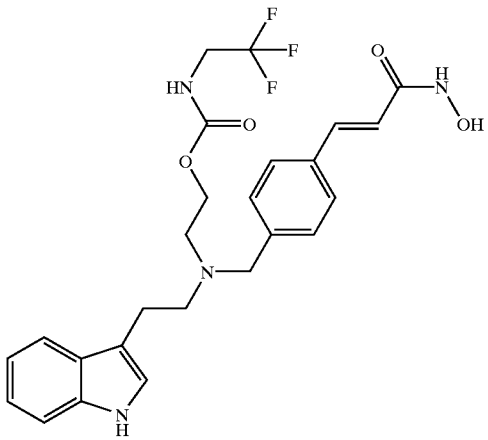 | 505 |

| Example | STRUCTURE | m/z (MH+) |
|---|---|---|
| 104 | 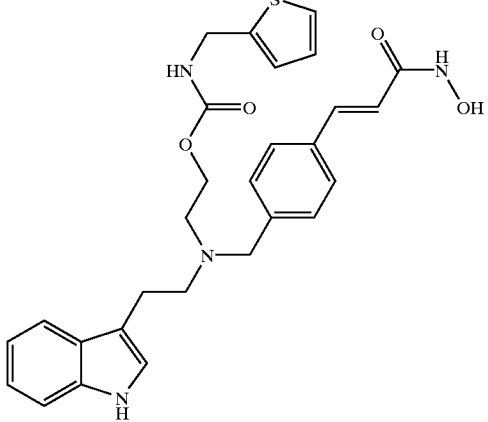 | 519 |
| 105 | 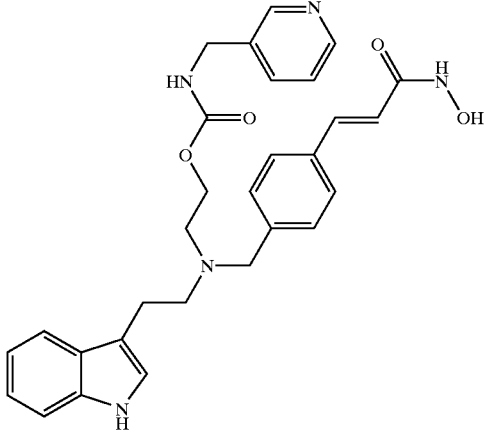 | 514 |
| 106 | 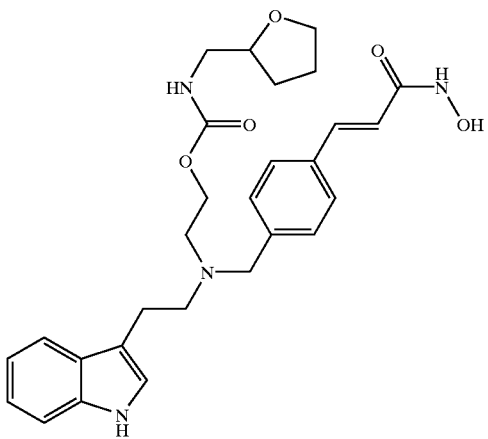 | 507 |

-continued
| Example | STRUCTURE | m/z (MH+) |
|---|---|---|
| 107 | 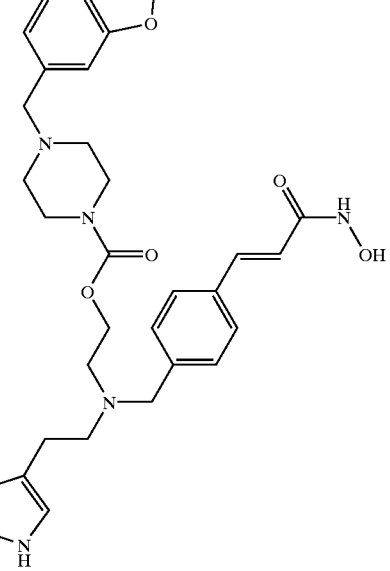 | 626 |
| 108 | 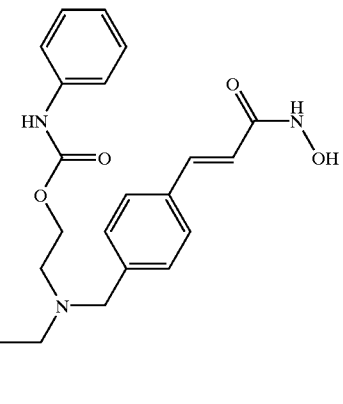 | 499 |
| 109 | 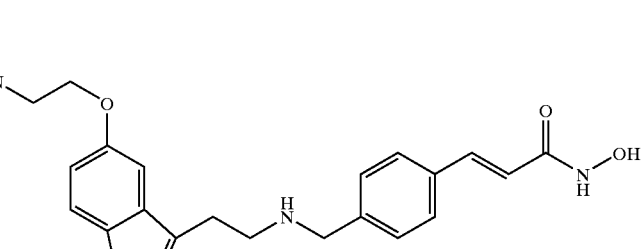 | |

-continued
| Example | STRUCTURE | m/z (MH+) |
|---|---|---|
| 110 | 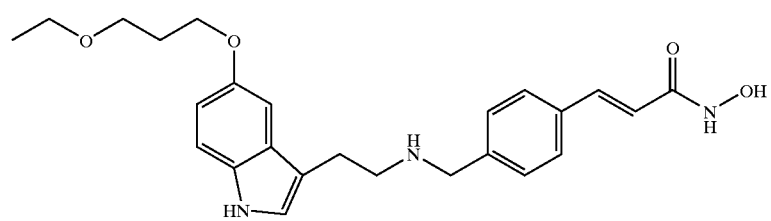 | |
| 111 | 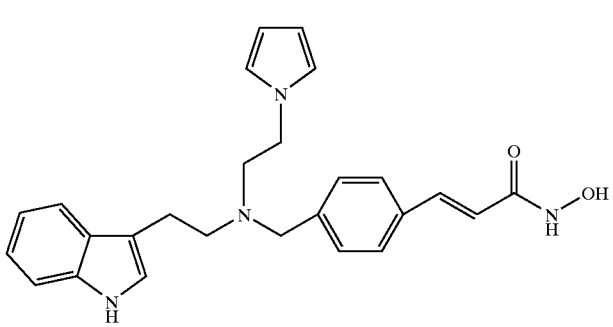 | 429 |
| 112 | 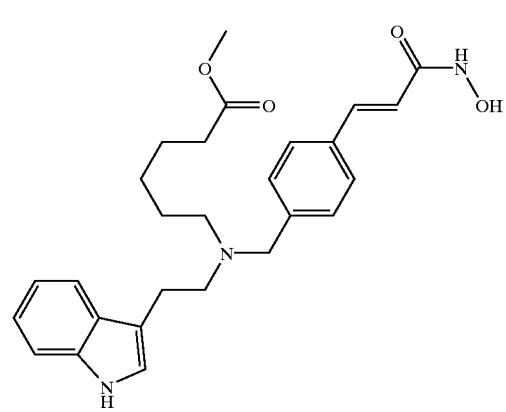 | 464 |
| 113 | 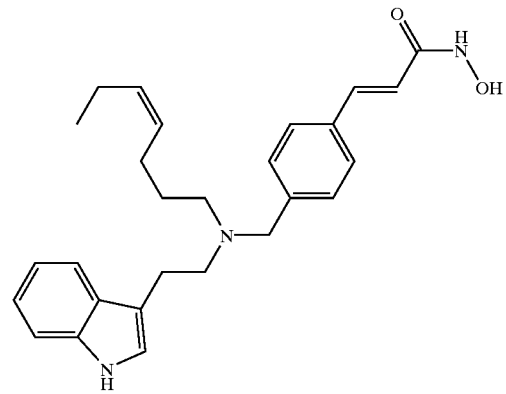 | 432 |

-continued

| Example | STRUCTURE | m/z (MH+) |
|---|---|---|
| 114 | 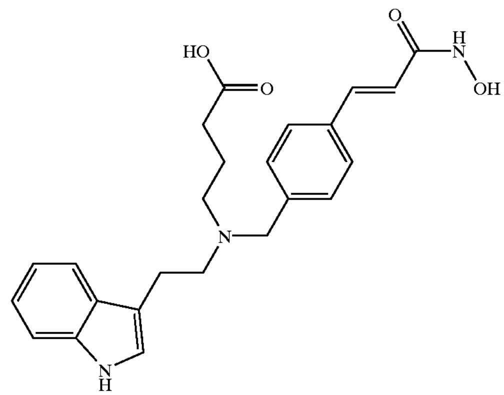 | 422 |
| 115 | 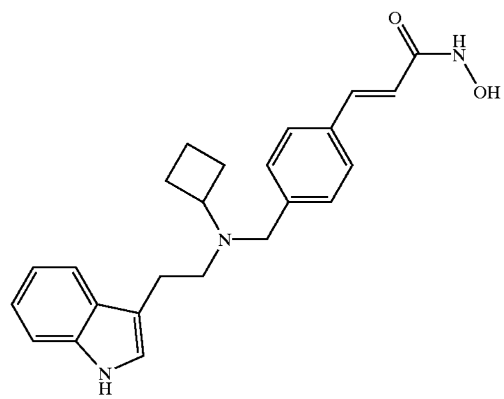 | 390 |
| 116 | 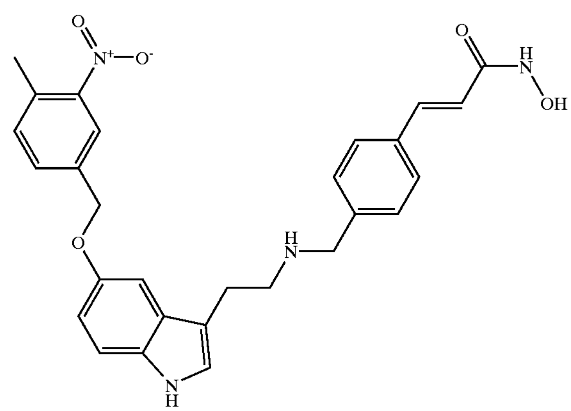 | 501 |
| 117 | 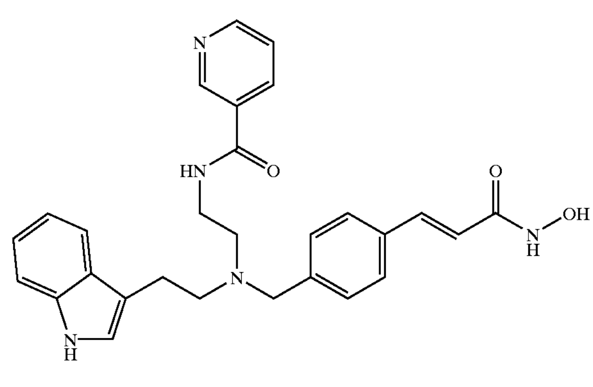 | 484 |

| Example | STRUCTURE | m/z (MH+) |
|---|---|---|
| 118 | 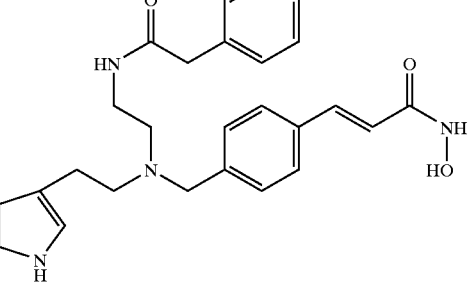 | |
| 119 | 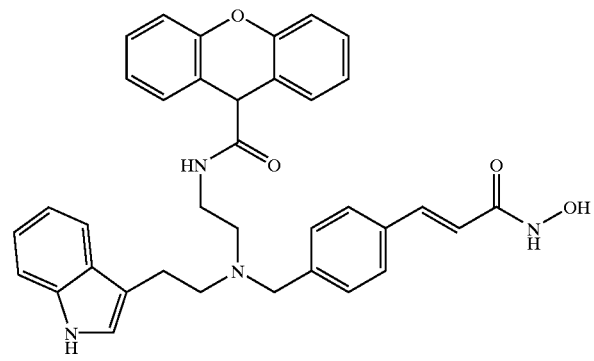 | 587 |
| 120 | 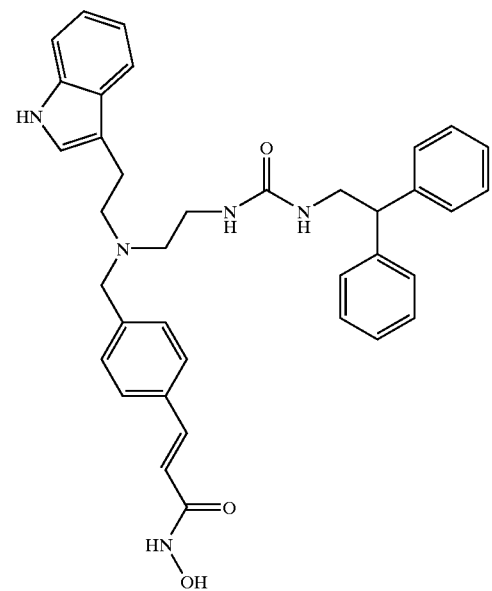 | 602 |

-continued
| Example | STRUCTURE | m/z (MH+) |
|---|---|---|
| 121 | 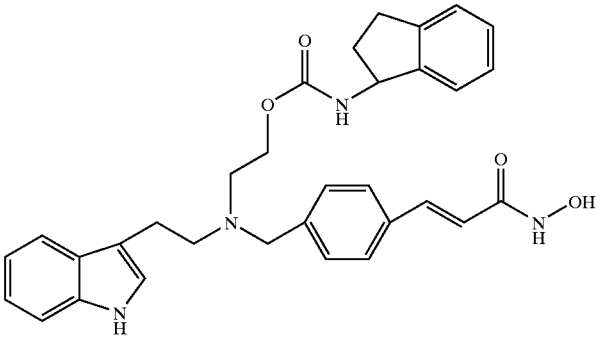 | 539 |
| 122 | 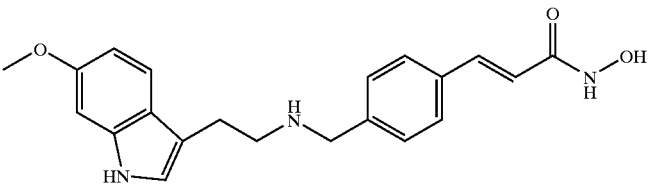 | |
| 123 | 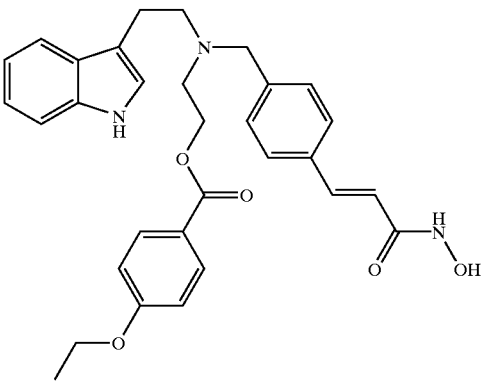 | 528 |
| 124 | 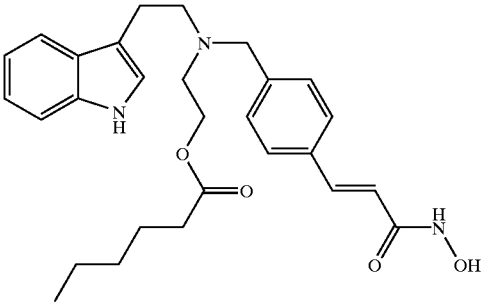 | 487 |
| 125 | 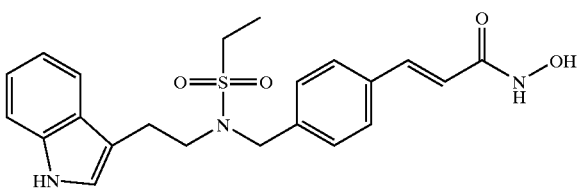 | |

-continued
| Example | STRUCTURE | m/z (MH+) |
|---|---|---|
| 126 | 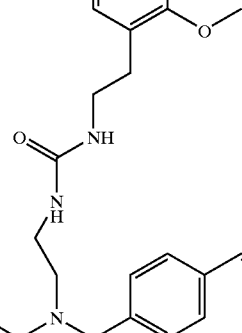 | 556 |
| 127 | 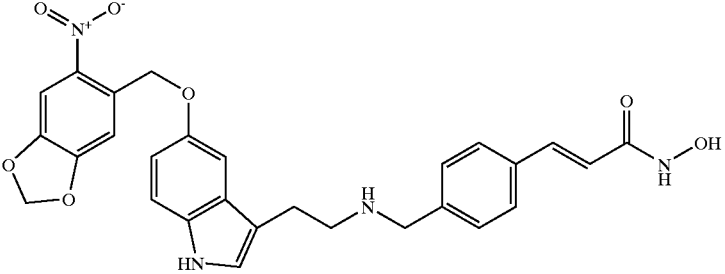 | |
| 128 | 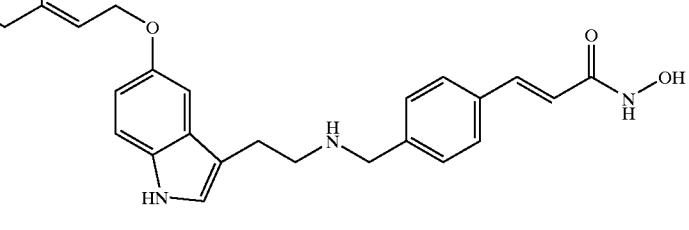 | |
| 129 | 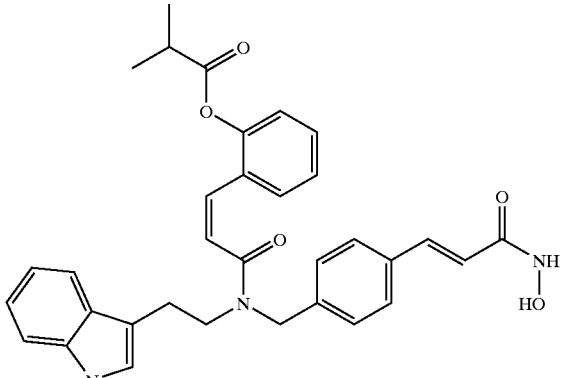 | 552 |

-continued
| Example | STRUCTURE | m/z (MH+) |
|---|---|---|
| 130 | 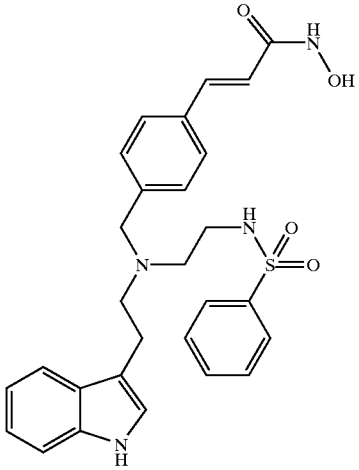 | 519 |
| 131 | 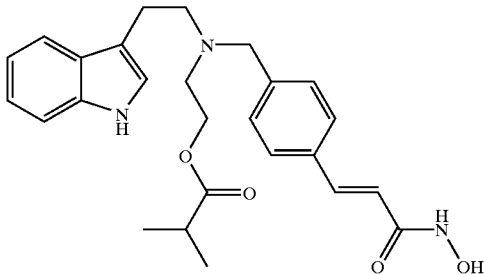 | 450 |
| 132 | 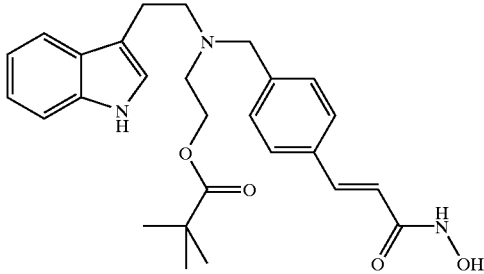 | 464 |
| 133 | 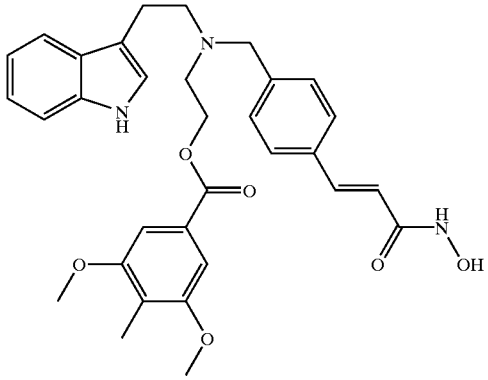 | 558 |

-continued

| Example | STRUCTURE | m/z (MH⁺) |
|---|---|---|
| 134 | 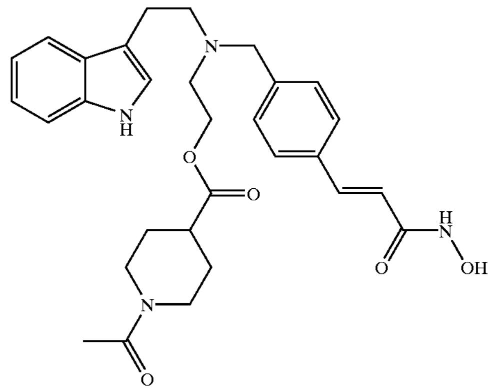 | 533 |
| 135 | 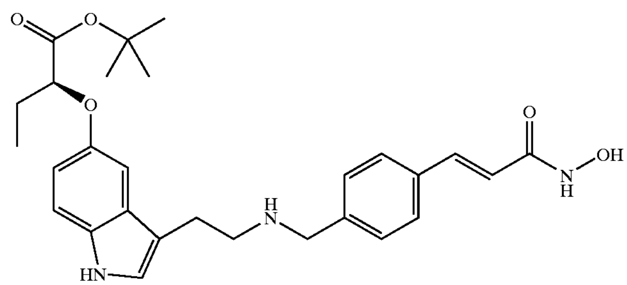 | |
| 136 | 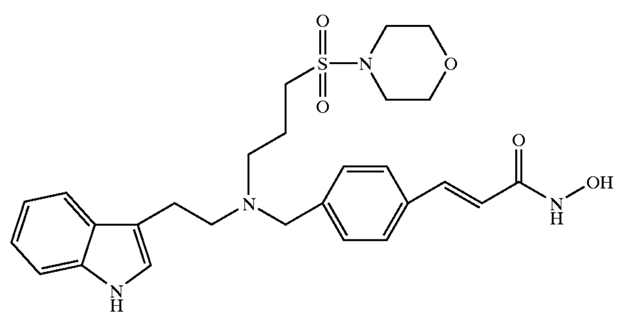 | 527 |
| 137 | 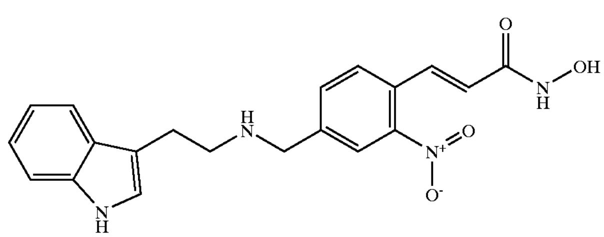 | 381 |
| 138 | 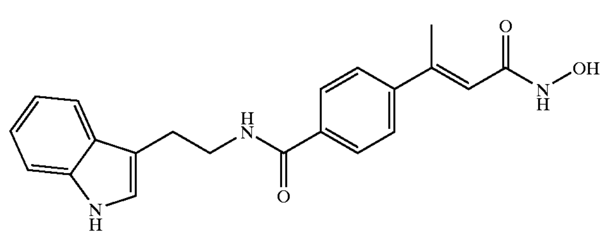 | 364 |

-continued

| Example | STRUCTURE | m/z (MH+) |
|---|---|---|
| 139 | 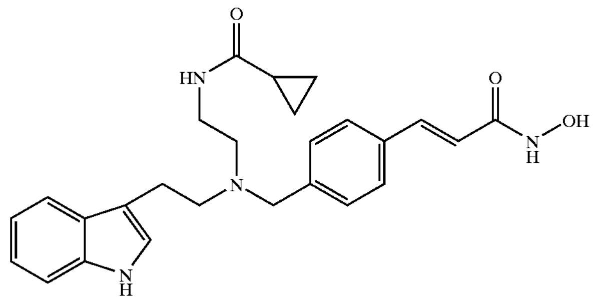 | |
| 140 | 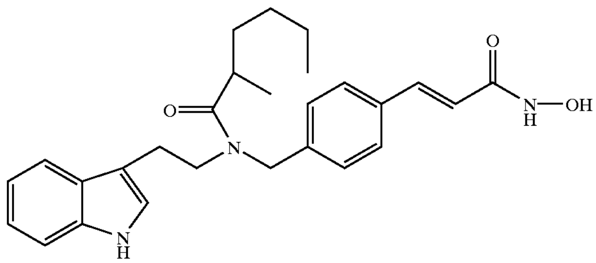 | 448 |
| 141 | 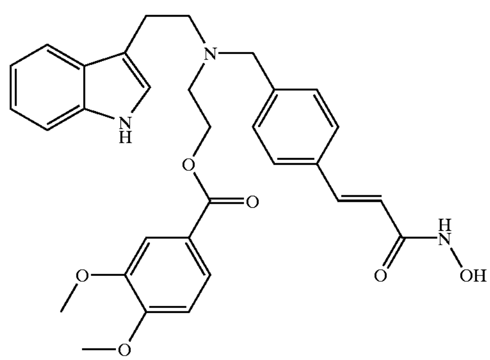 | 558 |
| 142 | 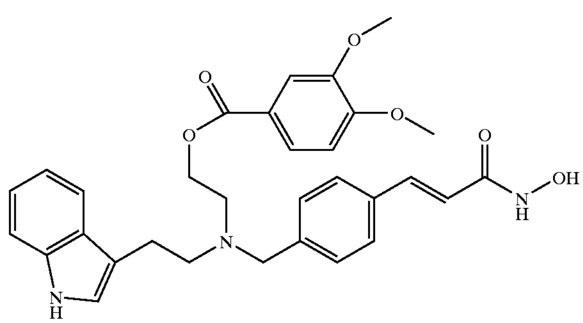 | |
| 143 | 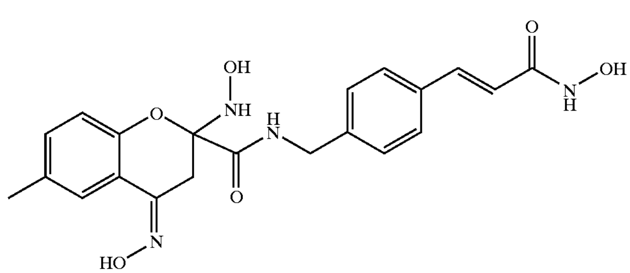 | 427 |

-continued

| Example | STRUCTURE | m/z (MH+) |
|---|---|---|
| 144 | 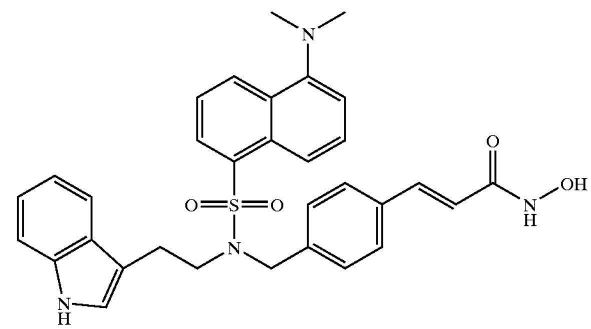 | |
| 145 | 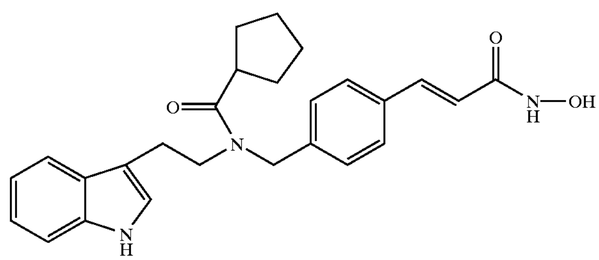 | 432 |
| 146 | 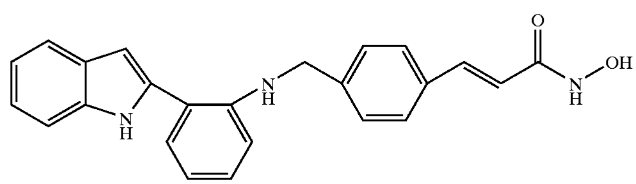 | 384 |
| 147 | 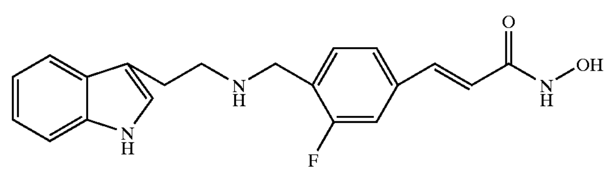 | 354 |
| 148 | 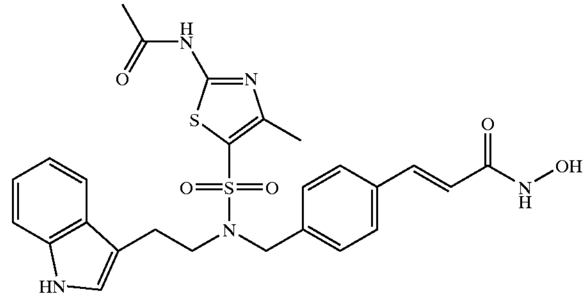 | |
| 149 | 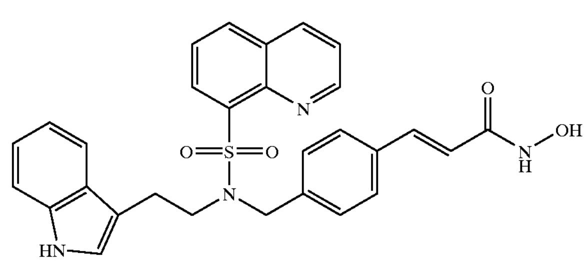 | |

-continued

| Example | STRUCTURE | m/z (MH+) |
|---|---|---|
| 150 | 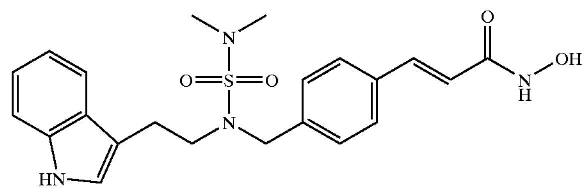 | |
| 151 | 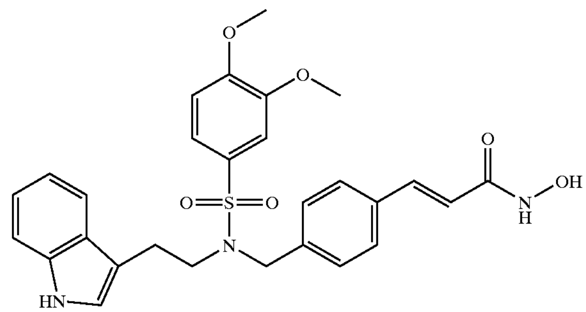 | |
| 152 | 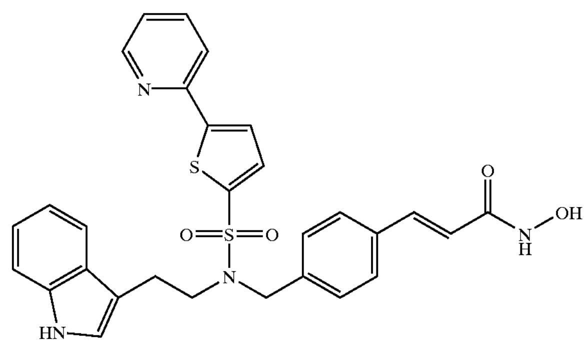 | |
| 153 | 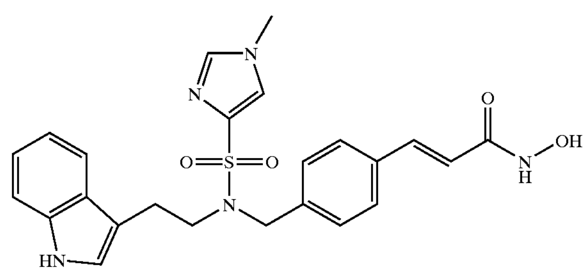 | |
| 154 | 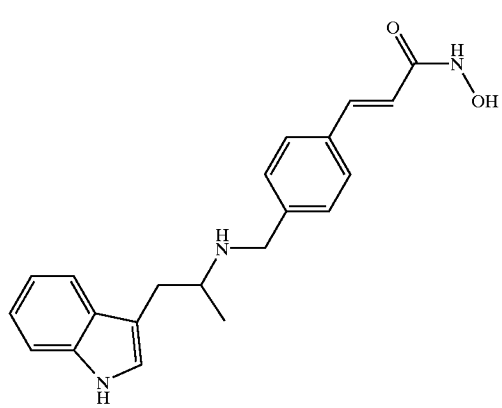 | 350 |

-continued

| Example | STRUCTURE | m/z (MH+) |
|---|---|---|
| 155 | 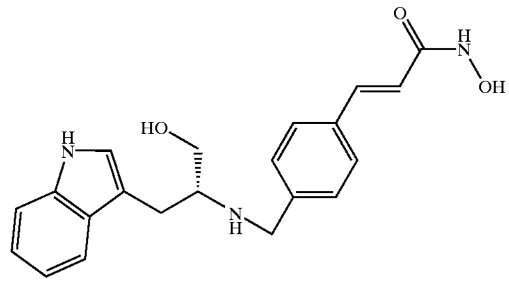 | 366 |
| 156 | 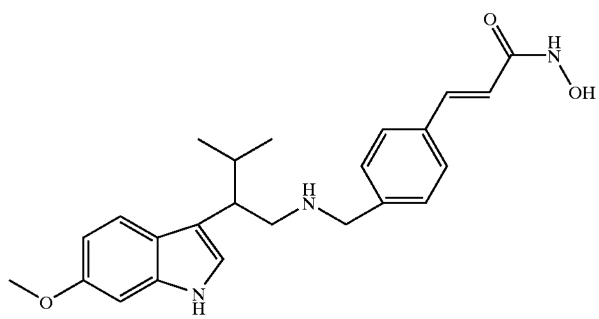 | 408 |
| 157 | 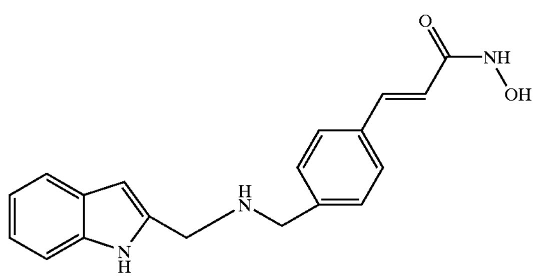 | 322 |
| 158 | 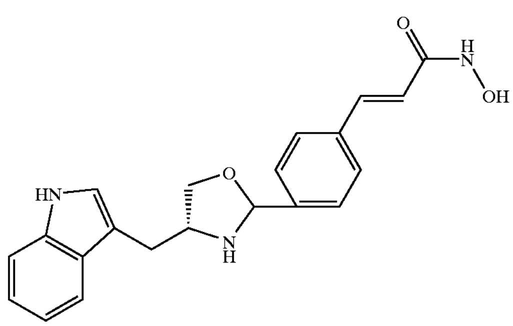 | 364 |
| 159 | 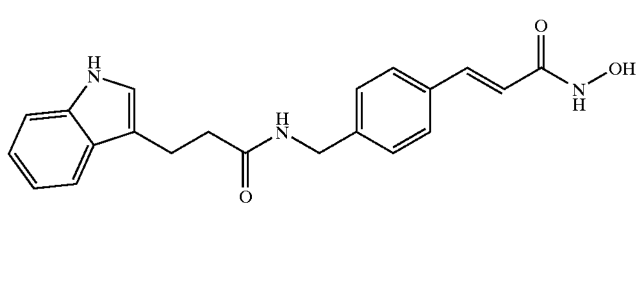 | 364 |

-continued

| Example | STRUCTURE | m/z (MH+) |
|---|---|---|
| 160 | 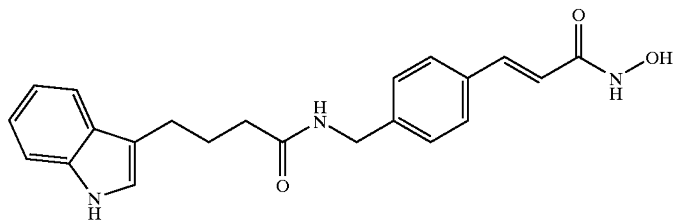 | 378 |
| 161 | 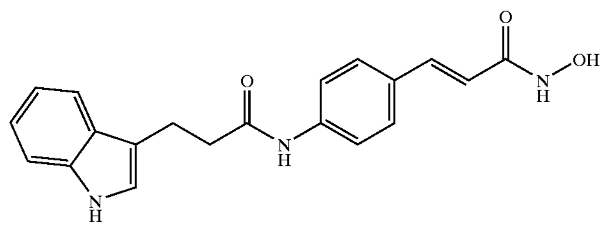 | 350 |
| 162 | 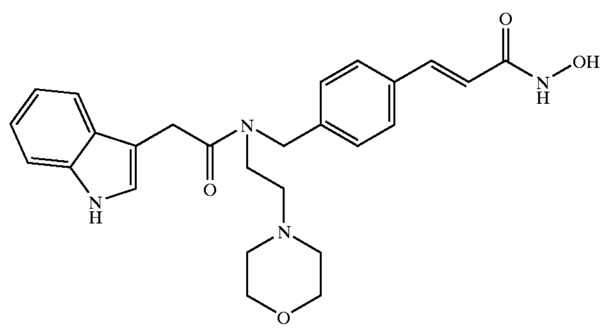 | 463 |
| 163 | 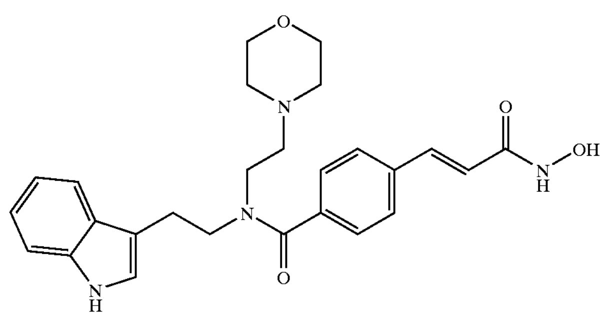 | |
| 164 | 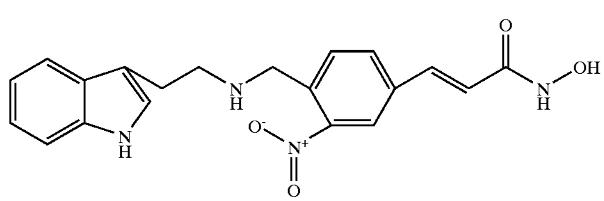 | 381 |
| 165 | 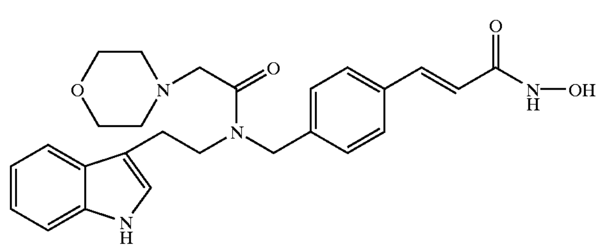 | 463 |

-continued
| Example | STRUCTURE | m/z (MH+) |
|---|---|---|
| 166 | 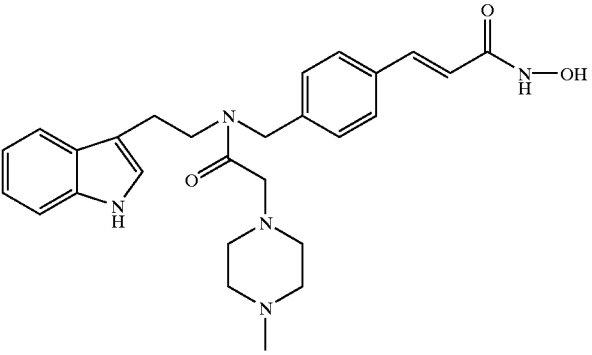 | 476 |
| 167 | 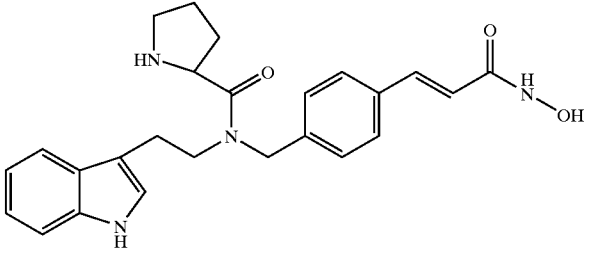 | |
| 168 | 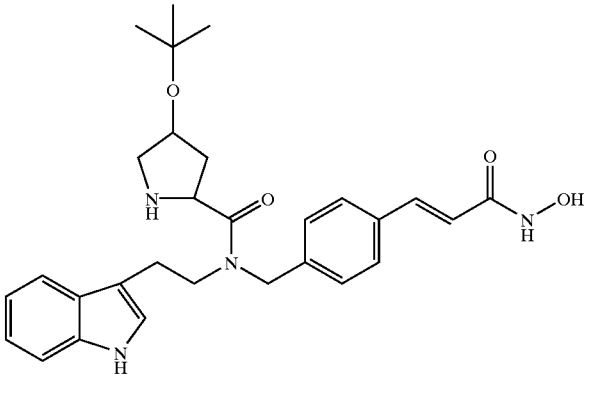 | |
| 169 | 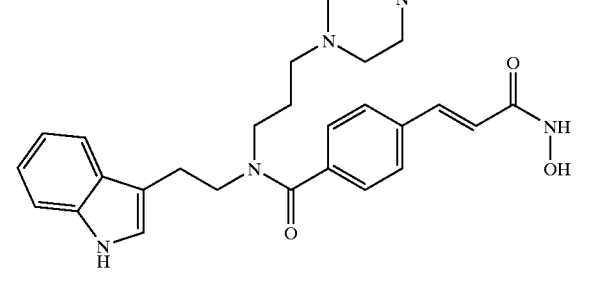 | |
| 170 | 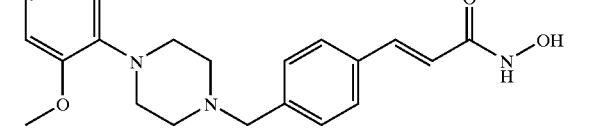 | 368 |

-continued

| Example | STRUCTURE | m/z (MH+) |
|---|---|---|
| 171 | 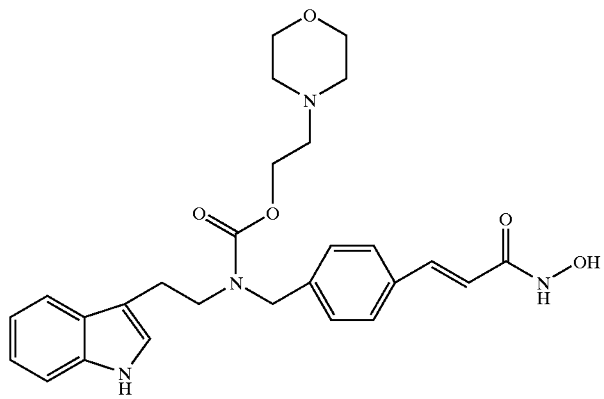 | 493 |
| 172 | 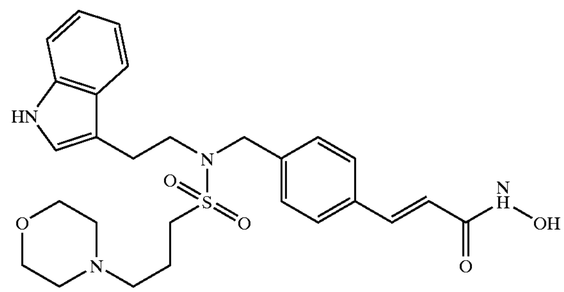 | 527 |
| 173 | 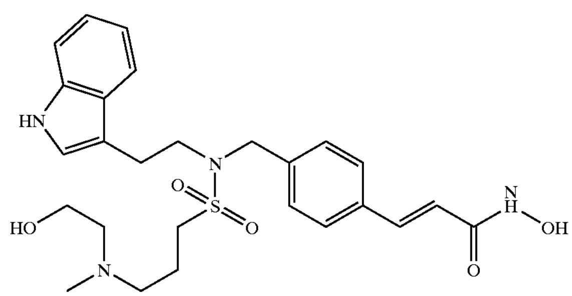 | 515 |
| 174 | 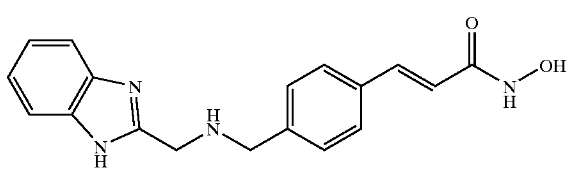 | 323 |
| 175 | 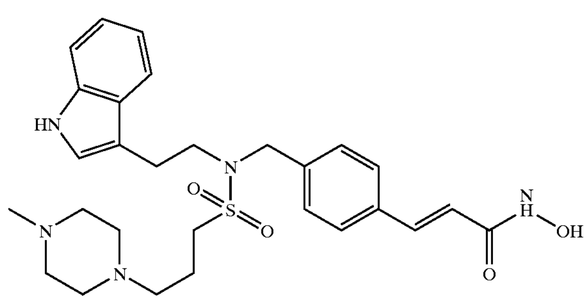 | 540 |

-continued
| Example | STRUCTURE | m/z (MH+) |
|---|---|---|
| 176 | 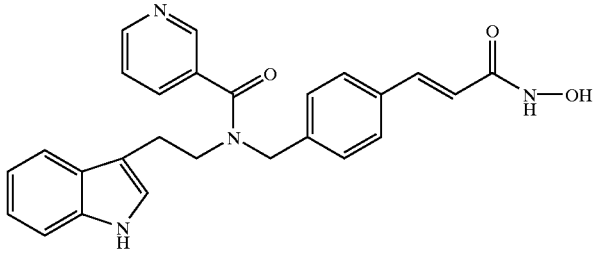 | 441 |
| 177 | 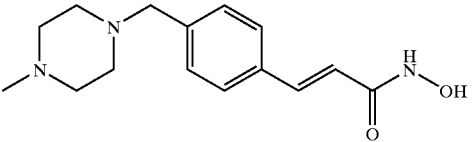 | 276 |
| 178 | 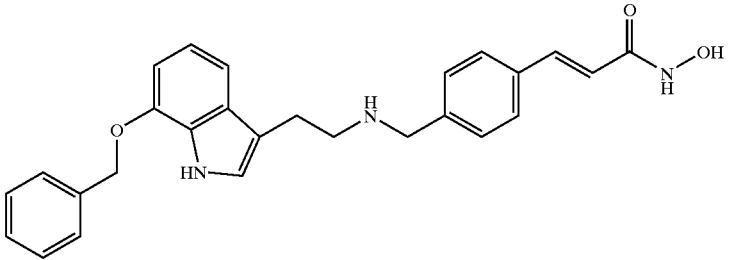 | |
| 179 | 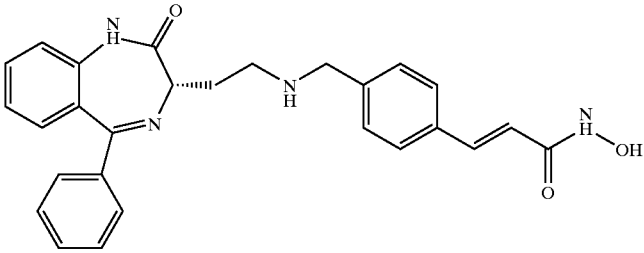 | 455 |
| 180 | 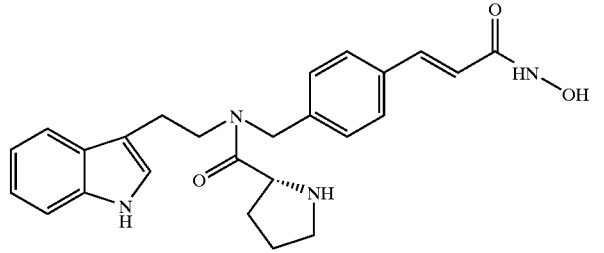 | |
| 181 | 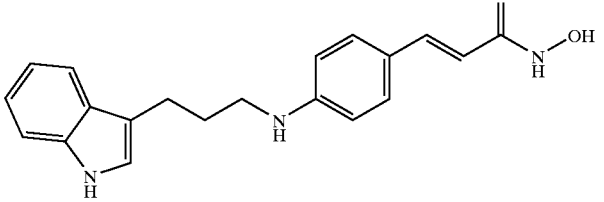 | 336 |

-continued

| Example | STRUCTURE | m/z (MH+) |
|---|---|---|
| 182 | 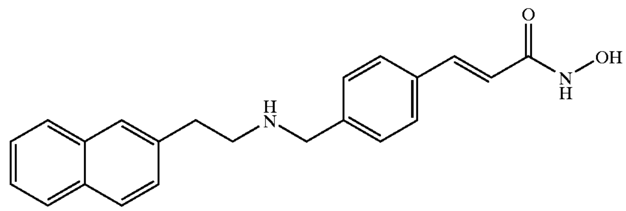 | 347 |
| 183 | 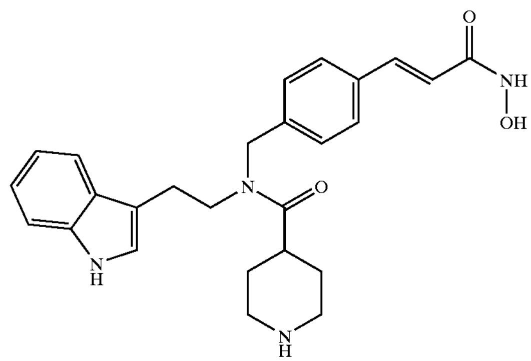 | 447 |
| 184 | 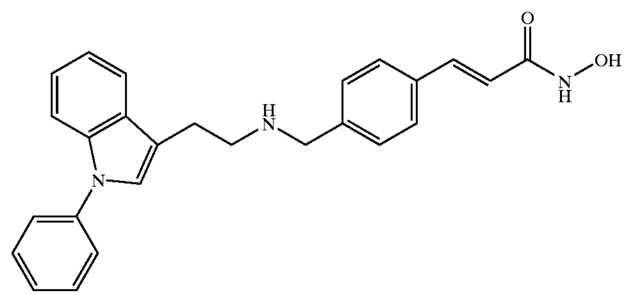 | |
| 185 | 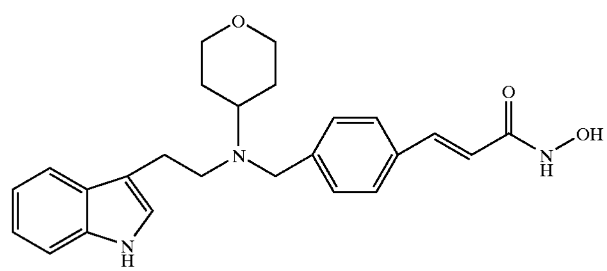 | 420 |
| 186 | 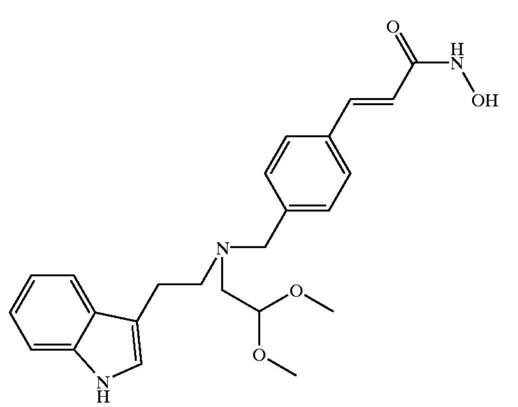 | 424 |

-continued
| Example | STRUCTURE | m/z (MH+) |
|---|---|---|
| 187 | 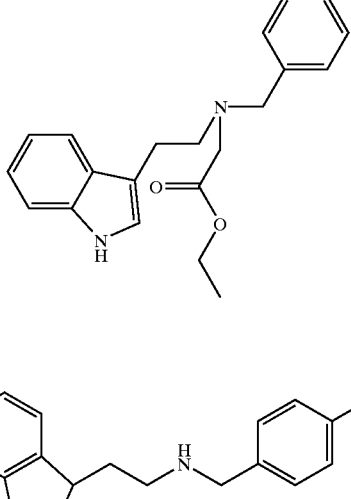 | 422 |
| 188 | 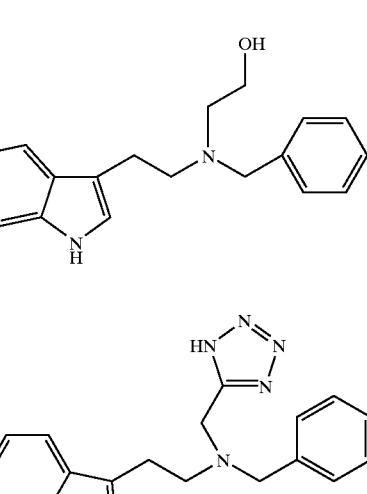 | |
| 189 | 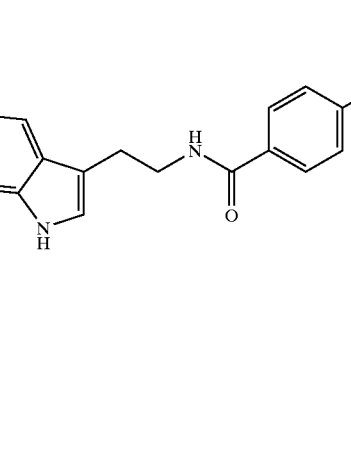 | 398 |
| 190 | 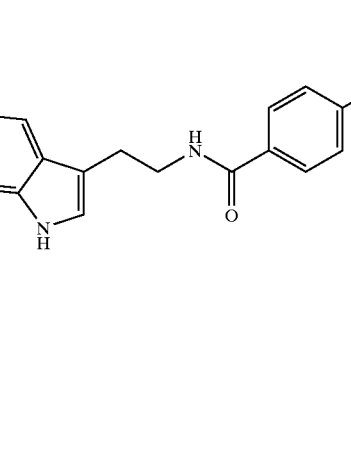 | 418 |
| 191 | 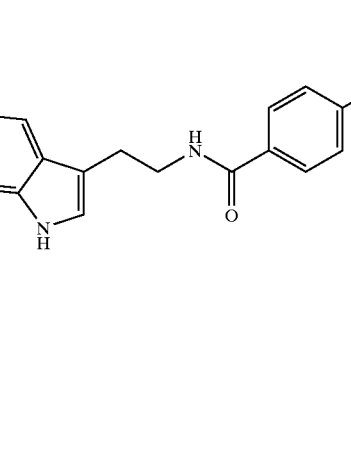 | 350 |

-continued
| Example | STRUCTURE | m/z (MH+) |
|---|---|---|
| 192 | 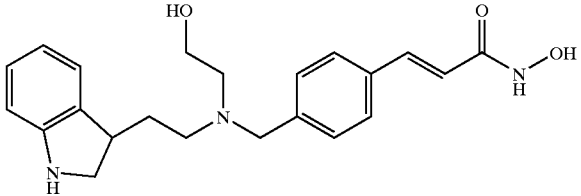 | |
| 193 | 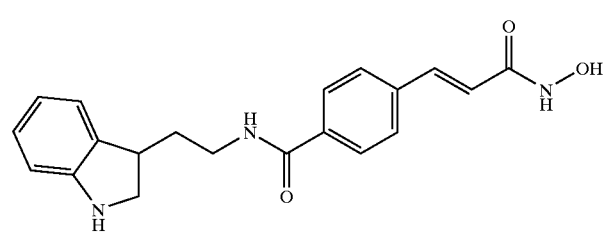 | 352 |
| 194 | 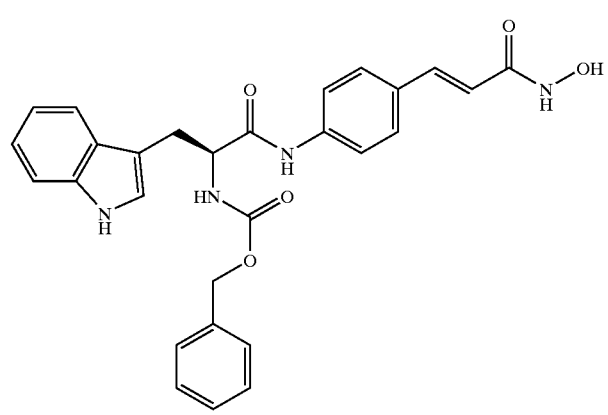 | 499 |
| 195 | 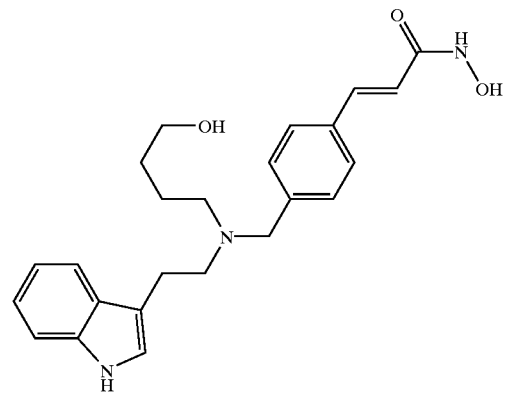 | 408 |

-continued
| Example | STRUCTURE | m/z (MH+) |
|---|---|---|
| 196 | 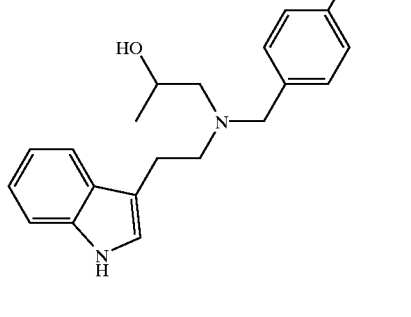 | 394 |
| 197 | 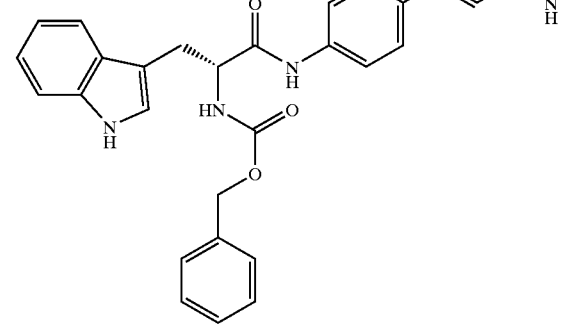 | 499 |
| 198 | 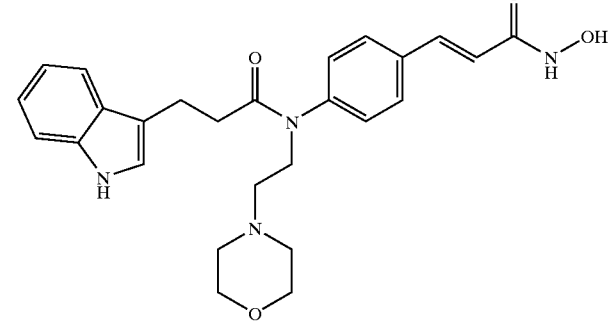 | |
| 199 | 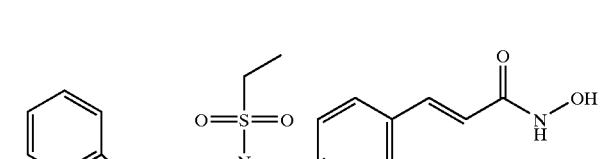 | |

-continued

| Example | STRUCTURE | m/z (MH+) |
|---|---|---|
| 200 | 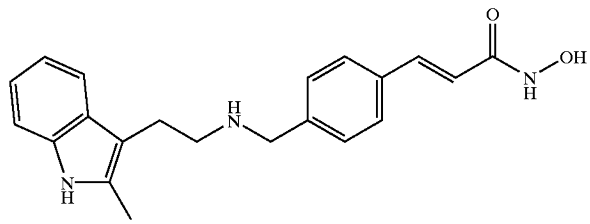 | 350 |
| 201 | 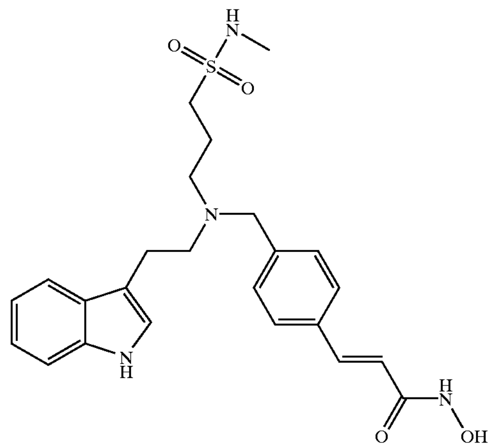 | |
| 202 | 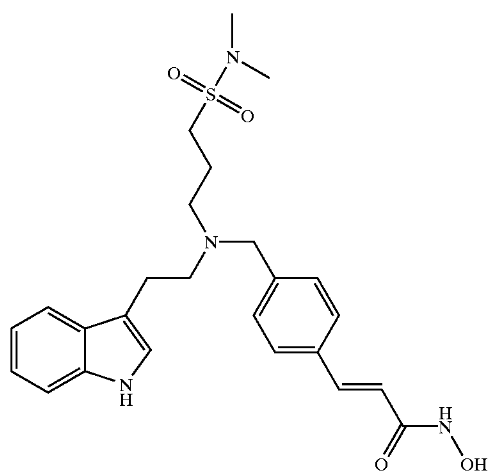 | |
| 203 | 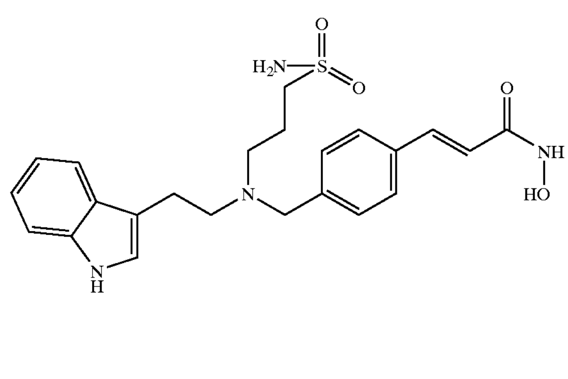 | |

-continued
| Example | STRUCTURE | m/z (MH+) |
|---|---|---|
| 204 | 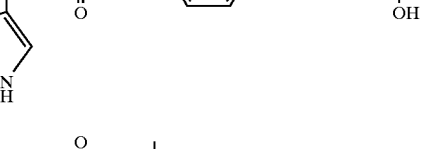 | 365 |
| 205 | 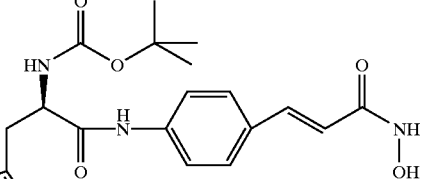 | 465 |
| 206 | 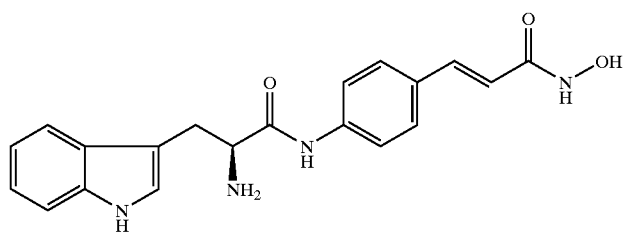 | 365 |
| 207 | 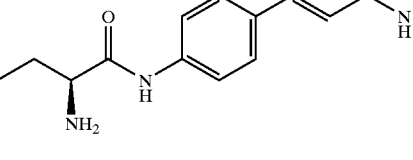 | 410 |
| 208 | 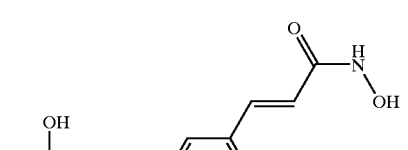 | 410 |

| Example | STRUCTURE | m/z (MH+) |
|---|---|---|
| 209 | 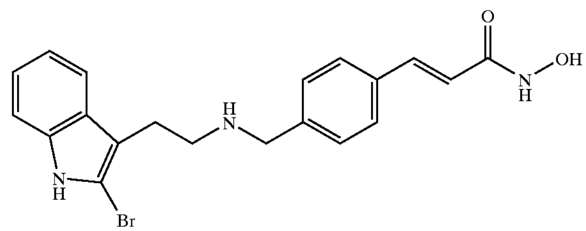 | |
| 210 | 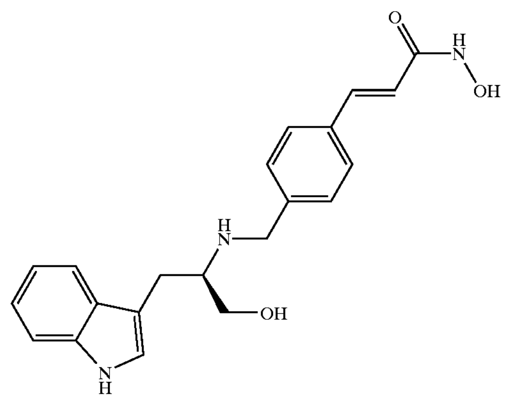 | 366 |
| 211 | 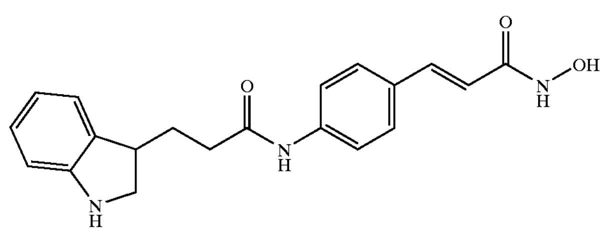 | 352 |
| 212 | 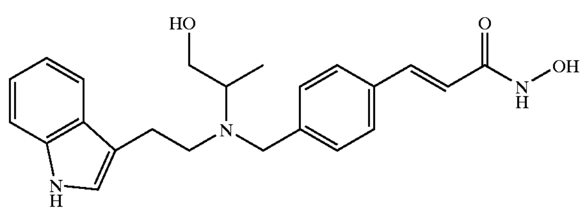 | |
| 213 | 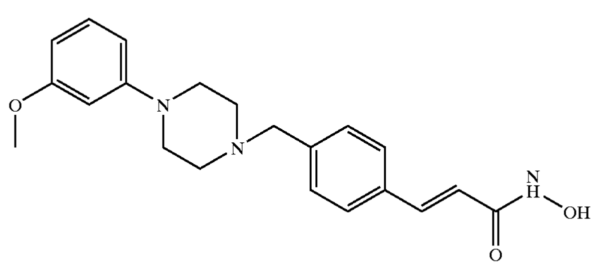 | 368 |

-continued

| Example | STRUCTURE | m/z (MH+) |
|---|---|---|
| 214 | 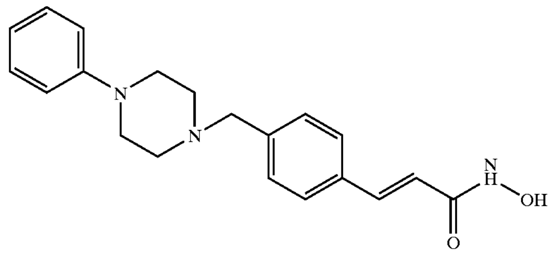 | 338 |
| 215 | 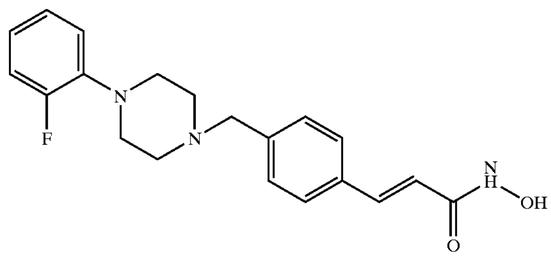 | 356 |
| 216 | 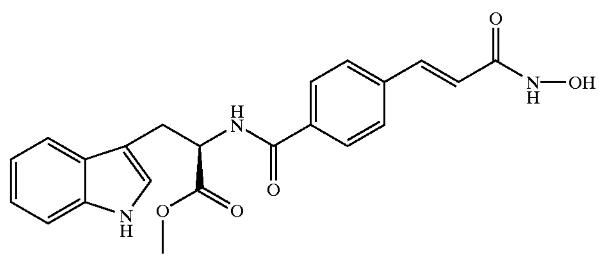 | 408 |
| 217 | 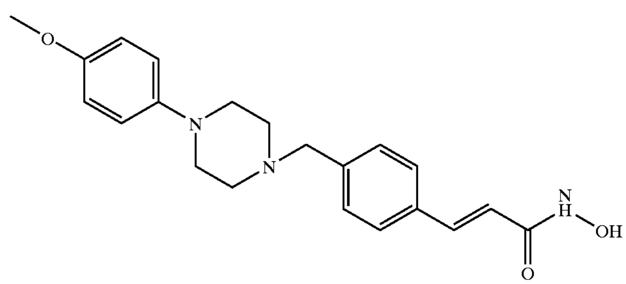 | 368 |
| 218 | 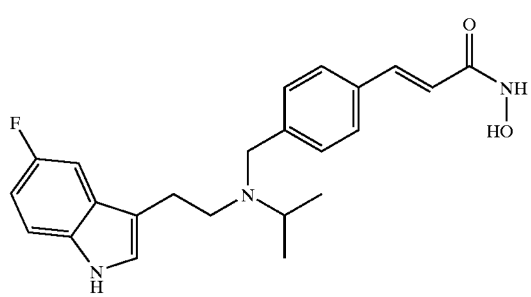 | 396 |

-continued
| Example | STRUCTURE | m/z (MH+) |
|---|---|---|
| 219 | 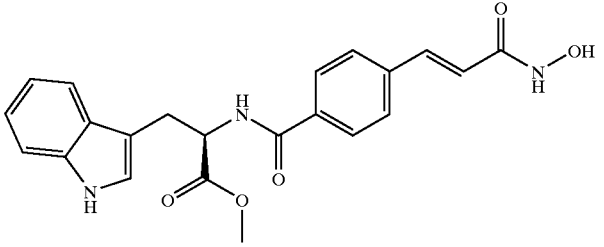 | |
| 220 | 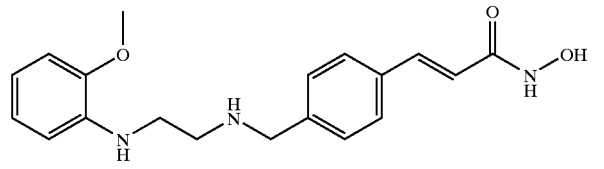 | 342 |
| 221 | 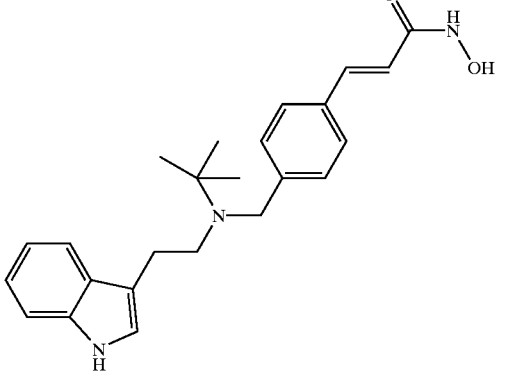 | 392 |
| 222 | 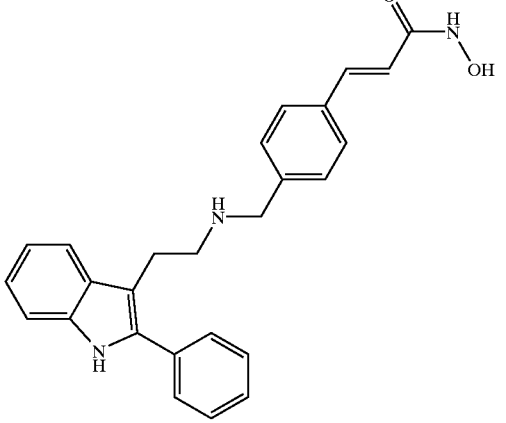 | 412 |
| 223 | 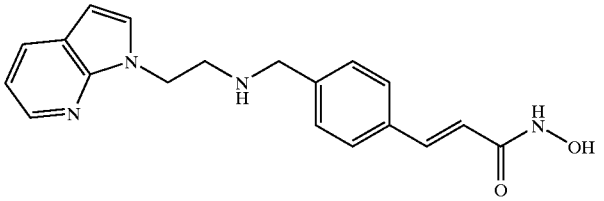 | 337 |

-continued

| Example | STRUCTURE | m/z (MH+) |
|---|---|---|
| 224 | 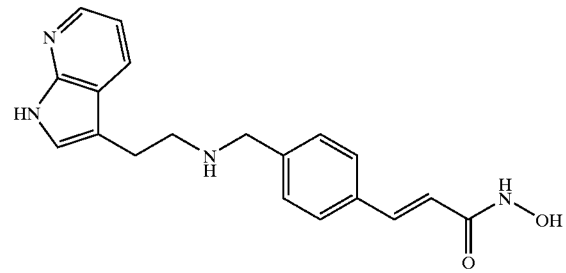 | 337 |
| 225 | 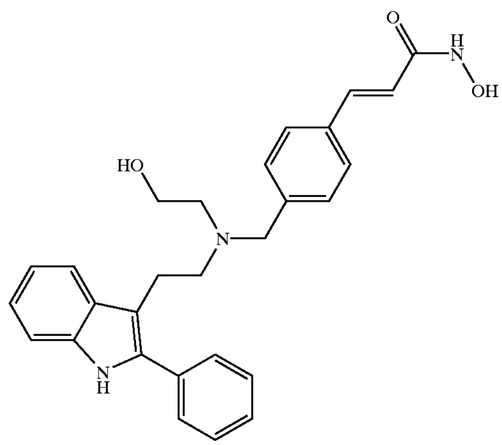 | 456 |
| 226 | 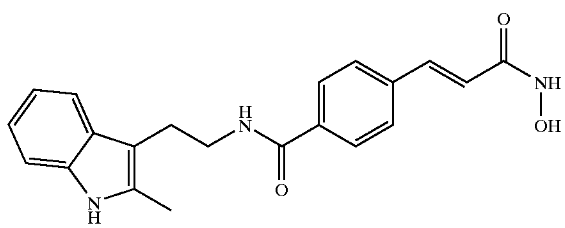 | 364 |
| 227 | 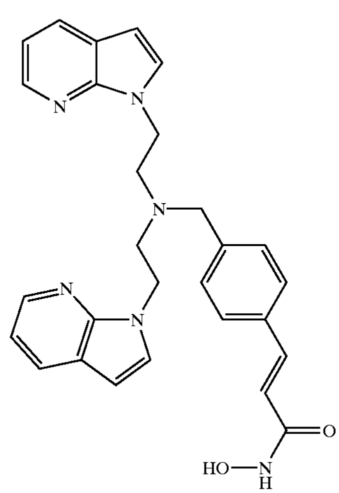 | 481 |

| Example | STRUCTURE | m/z (MH+) |
|---|---|---|
| 228 | 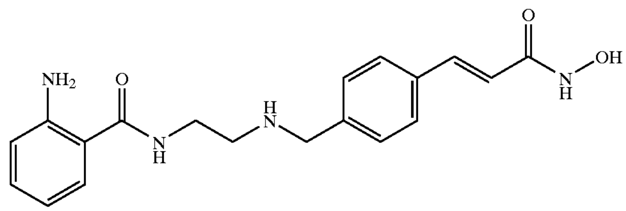 | 355 |
| 229 | 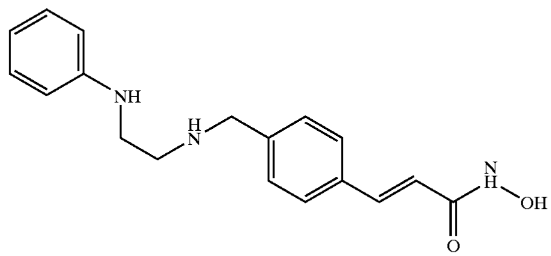 | 312 |
| 230 | 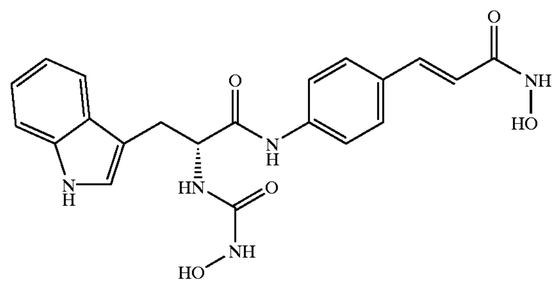 | 424 |
| 231 | 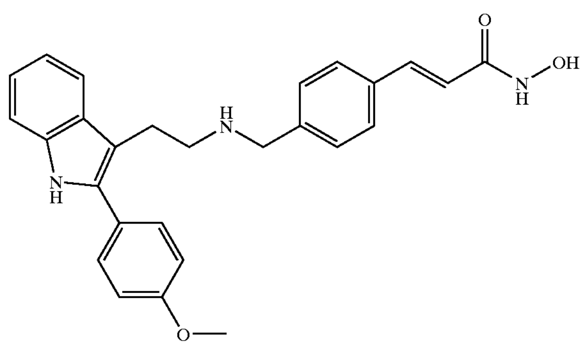 | |
| 232 | 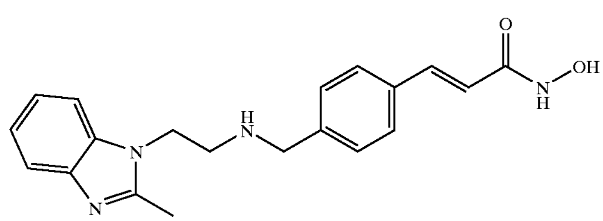 | 351 |
| 233 | 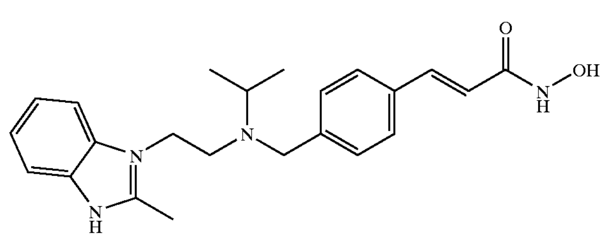 | 392 |

-continued

| Example | STRUCTURE | m/z (MH+) |
|---|---|---|
| 234 | 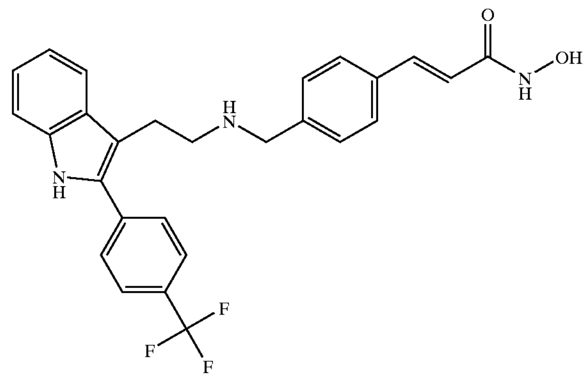 | |
| 235 | 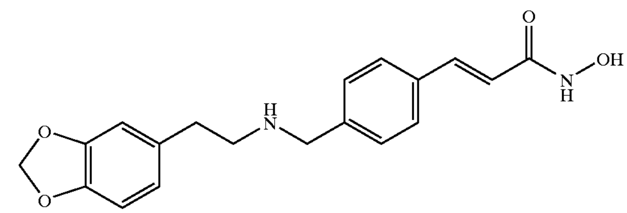 | |
| 236 | 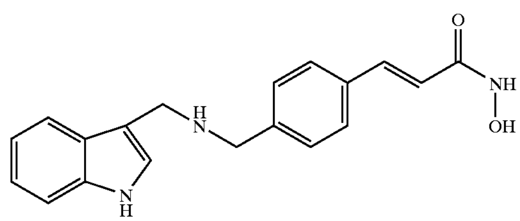 | 322 |
| 237 | 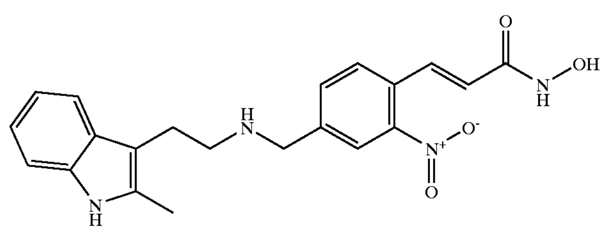 | |
| 238 | 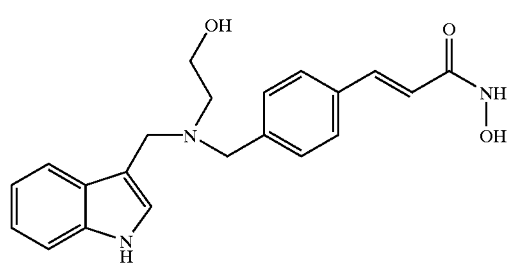 | 366 |

-continued

| Example | STRUCTURE | m/z (MH+) |
|---|---|---|
| 239 | 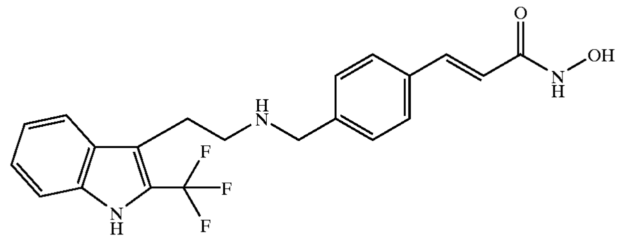 | |
| 240 | 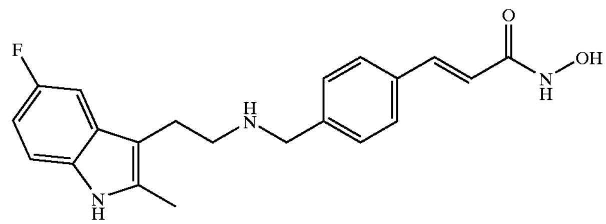 | 368 |
| 241 | 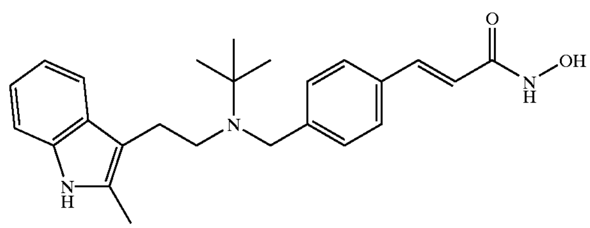 | |
| 242 | 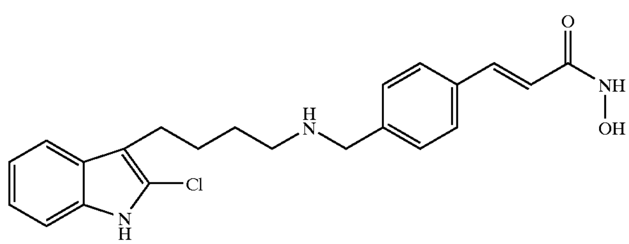 | 406 |
| 243 | 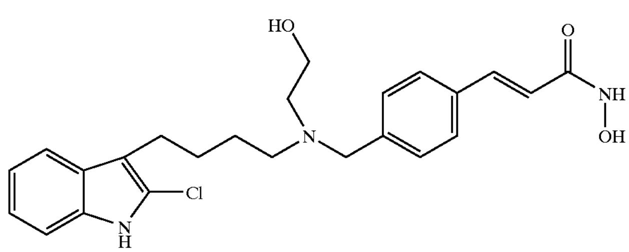 | 398 |
| 244 | 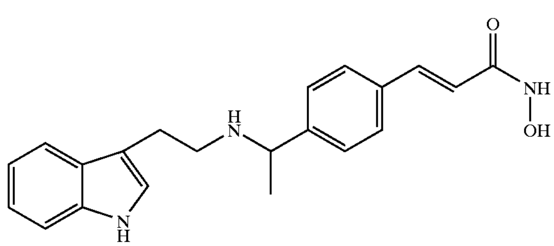 | 442 |

-continued

| Example | STRUCTURE | m/z (MH⁺) |
|---|---|---|
| 245 | (structure) | 350 |
| 246 | (structure) | 364 |
| 247 | (structure) | 402 |
| 248 | (structure) | 418 |

-continued

| Example | STRUCTURE | m/z (MH+) |
|---|---|---|
| 249 | 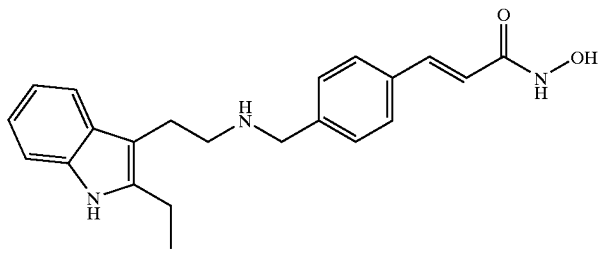 | 364 |
| 250 | 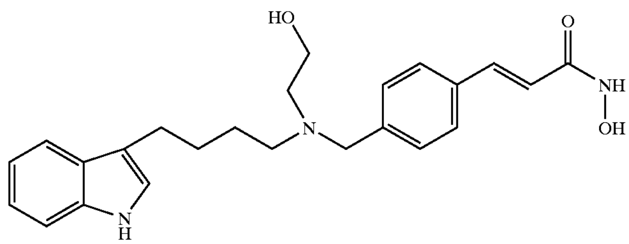 | |
| 251 | 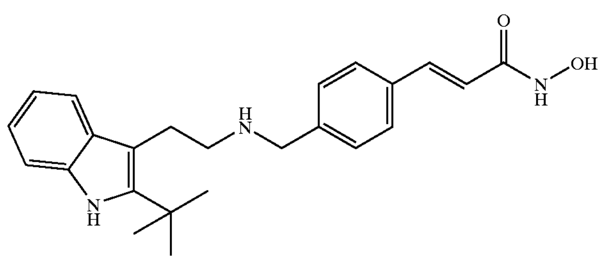 | 408 |
| 252 | 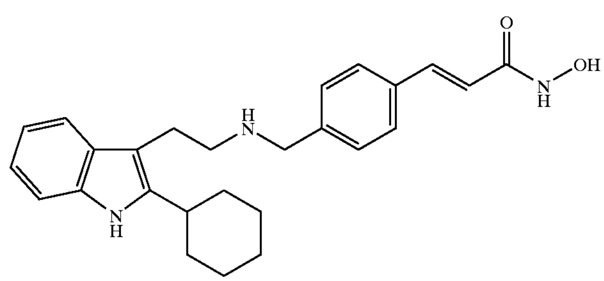 | |
| 253 | 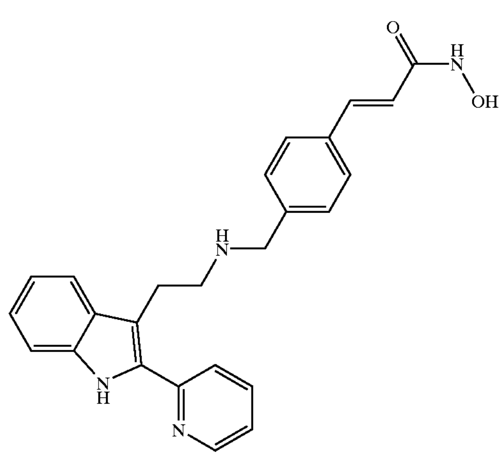 | |

-continued

| Example | STRUCTURE | m/z (MH⁺) |
|---|---|---|
| 254 | 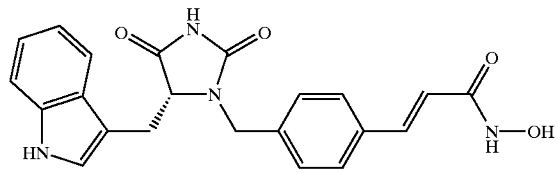 | 413 |
| 255 | 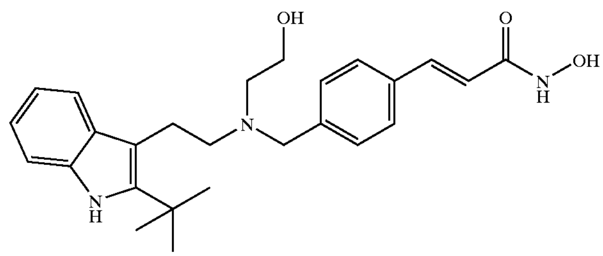 | 405 |
| 256 | 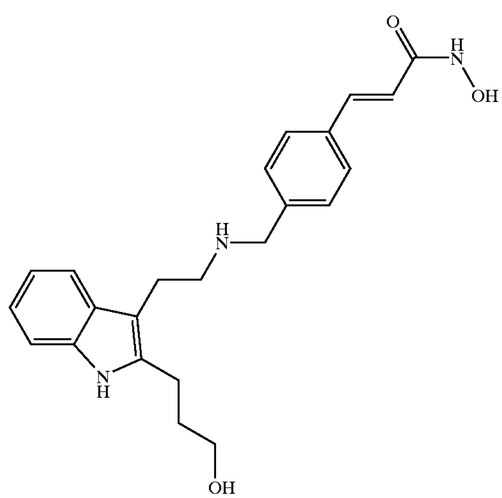 | |
| 257 | 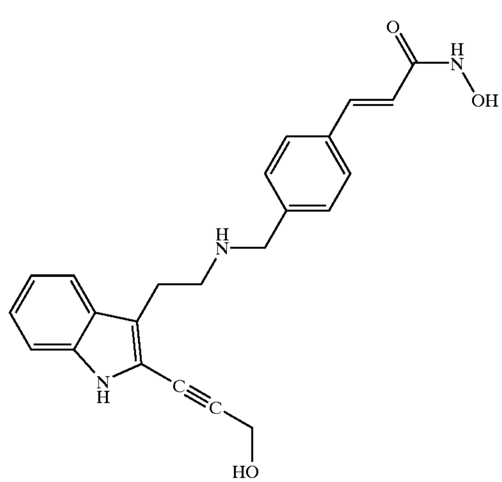 | 394 |

| Example | STRUCTURE | m/z (MH+) |
|---|---|---|
| 258 | 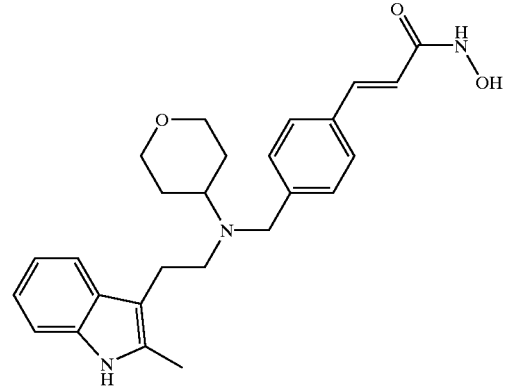 | 390 |
| 259 | 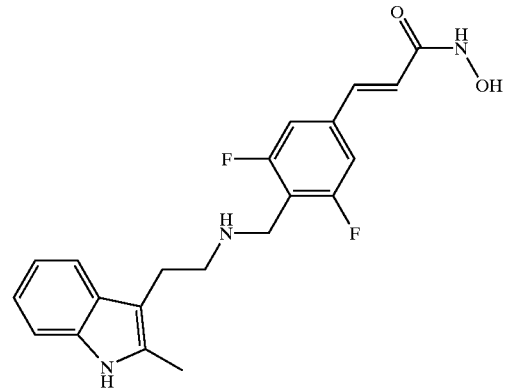 | 434 |
| 260 | 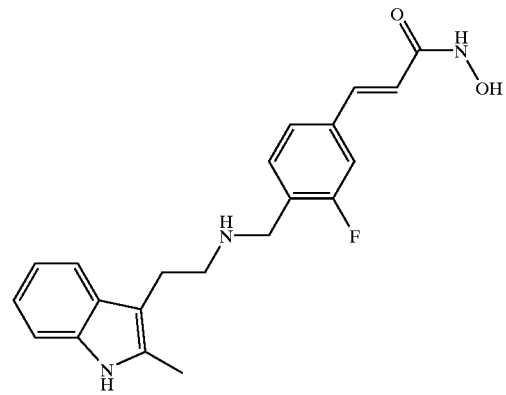 | 386 |

| Example | STRUCTURE | m/z (MH+) |
|---|---|---|
| 261 | 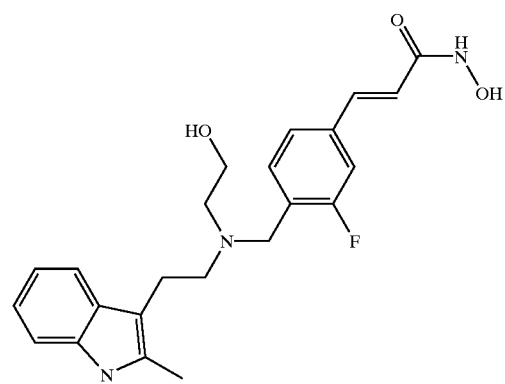 | 368 |
| 262 | 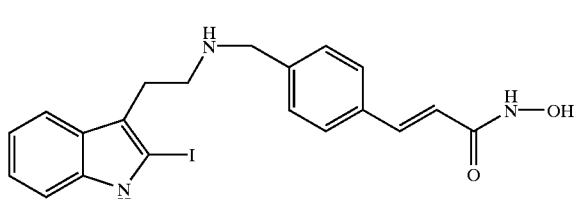 | 412 |
| 263 | 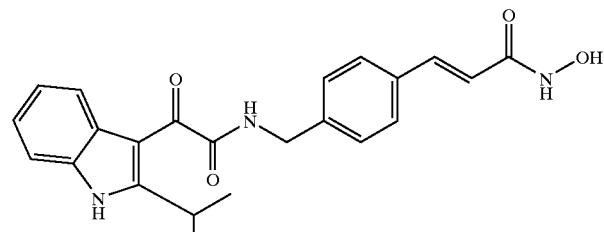 | 406 |
| 264 | 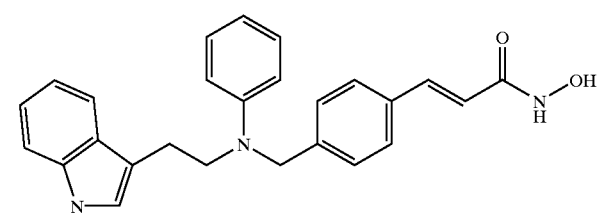 | 378 |
| 265 | 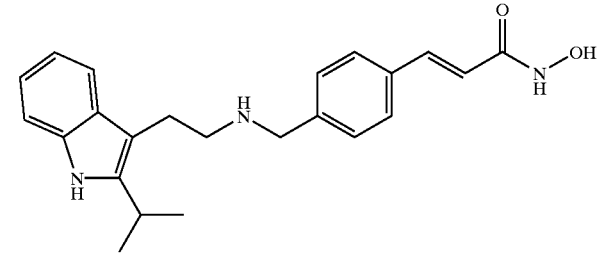 | 378 |

The compounds of Examples 1–265 show an HDA enzyme IC$_{50}$ in the range from about 0.005 to about 0.5 μM.

EXAMPLE B1

Cell lines H1299 (human lung carcinoma cell) and HCT116 (colon tumor cell) are obtained from the American Type Culture Collection, Rockville, Md. The cell lines are free of Mycoplasma contamination (Rapid Detection System by Gen-Probe, Inc., San Diego, Calif.) and viral contamination (MAP testing by MA BioServices, Inc., Rockville, Md.). The cell lines are propagated and expanded in RPMI 1640 medium containing 10% heat-inactivated FBS (Life Technologies, Grand Island, N.Y.). Cell expansions for implantation are performed in cell factories (NUNC, purchased from Fisher Scientific, Springfield, N.J.). Cells are harvested at 50–90% confluency, washed once with HBSS (Hank's Balanced Salt Solution) containing 10% FBS, and suspended in 100% HBSS.

Cell proliferation is measured with a commercial MTS kit (Promega, Madision, Wis.) assay using an adaptation of published procedures, for example, that disclosed in *Feasibility of drug screening with panels of human tumor cell lines using a microculture tetrazolium assay*, Alley M C, et al., Cancer Res. 1988; 48:589–601. Cells are plated in 96-well tissue culture dishes, with top and bottom rows left empty. H1299 and HCT116 cells are suspended in complete media at a density of $5.3 \times 10^3$ and $3.6 \times 10^3$ cell/mL, respectively, and 190 µl are added per well. Each cell line is added to one half of the plate. Complete medium (200 µL) is added to the top and bottom rows. Twenty-four hours later, 10 µl of MTS solution is added to one of the plates to determine the activity at the time of compound addition ($T_0$). The plate is incubated at 37° C. for 4 hours and the $OD_{490}$ is measured on a Molecular Devices Thermomax at 490 nm using the Softmax program. The $T_0$ plate serves as a reference for initial activity at the beginning of the experiment.

Five serial dilutions (1:4) of each compound are made in a 96-deep well plate with the highest concentrations on the edge of plate. Two cell lines are tested with two compounds per plate.0 Ten microliters of each of the five dilutions are added in triplicate and complete medium alone is added to columns six and seven. The plates are incubated at 37° C. for 72 hours. The MTS solution is added (as for the $T_0$ plate) and read four hours later.

In order to analyze the data, the average background value (media alone) is subtracted from each experimental well; the triplicate values are averaged for each compound dilution. The following formulas are used to calculate percent growth.

If $X > T_0$, % Growth=$((X-T_0)/(GC-T_0)) \times 100$

If $X < T_0$, % Growth=$(X-T_0)/T_0) \times 100$ in which $T_0$=(average value of cell viability at time 0)–background GC=average value of untreated cells (in triplicate)–background X=average value of compound treated cells (in triplicate)–background The "% Growth" is plotted against compound concentration and used to calculate $IC_{50}$s employing the linear regression techniques between data points to predict the concentration of compounds at 50% inhibition.

Lactate salts of N-hydroxy-3-[4-[[[2-(1H-indol-3-yl)-ethyl]-amino]methyl]phenyl]-2E-2-propenamide (CMD1), N-hydroxy-3-[4-[[(2-hydroxyethyl)[2-(1H-indol-3-yl) ethyl]-amino]methyl]phenyl]-2E-2-propenamide (CMD2), N-hydroxy-3-[4-[[[2-(5-methoxy-1H-indol-3-yl)-ethyl]-amino]methyl]phenyl]-2E-2-propenamide (CMD3), N-hydroxy-3-[4-[[[2-(5-fluoro-1H-indol-3yl)-ethyl]-amino]methyl]phenyl]-2E-2-propenamide (CMD4), N-hydroxy-3-[4-[[[2-(benzofur-3-yl)-ethyl]-amino]methyl]phenyl]-2E-2-propenamide (CMD5) having a purity of higher than 95% are dissolved in pure dimethylsulfoxide (DMSO) to create a stock solution. The stock solution is diluted with 5% dextrose injection, USP, just prior to dosing. In addition, N-(2-aminophenyl)-4[N-pyridin-3-yl) methoxycarbonylaminomethyl]benzamide is synthesized in accordance with Example 48 of EP 0 847 992 and used as a control compound (CMDC). Inhibition of cell growth in monolayer for 72 hours of compound treatment is measured in triplicate experiments and used to derive the $IC_{50}$ by MTS assay. The results are shown in Table B1.

TABLE B1

| Active Compound | Monolayer Growth $IC_{50}$ (µM) | |
| --- | --- | --- |
| | H1299 | HCT116 |
| CMD1 | 0.40 | 0.03 |
| CMD2 | 0.15 | 0.01 |
| CMD3 | 0.58 | 0.03 |
| CMD4 | 0.28 | 0.03 |
| CMD5 | 0.18 | 0.03 |
| CMDC | 6.8 | 0.67 |

The results show that the hydroxamate compounds of the present invention are highly active in inhibition of tumor cell growth. In addition to the above results, it has been observed that the compounds selectively inhibited tumor cells while showing minimal inhibition activities in non-tumorous cells.

The cells treated with the hydroxamate compounds are also tested for the induction of p21 promoter, which is a key mediator of G1 arrest and differentiation. The hydroxamate compounds activate the p21 promoter to a readily detectable level at a concentration within two-fold of their respective $IC_{50}$ for monolayer cell growth inhibition in H1299. Without being bound by amy particular theory, the correlation appears to demonstrate that HDA inhibition leads to transcriptional activation of genes that inhibit tumor cell proliferation.

EXAMPLE B2

HDA is partially purified from H1299, human non-small cell lung carcinoma cells (obtained from American Type Culture Collection, 12301 Parklawn Drive, Rockville, Md. 20852, USA). Cells are grown to 70–80% confluence in RPMI media in the presence of 10% FCS, harvested and lysed by sonication. The lysate is centrifuged at 23,420 g for 10–15 min, the supernatant is applied to a Hiload 26/10 High performance Q-sepharose column (Amersham Pharmacia Biotech), and equilibrated with a buffer containing 20 mM Tris pH8.0, 1 mM EDTA, 10 mM $NH_4Cl_2$, 1 mM µ-Mercaptoethanol, 5% glycerol, 2 µg/mL aprotinin, 1 µg/mL leupeptin, and 400 mM PMSF. Proteins are eluted in 4 mL aliquots with a linear gradient from 0–500 mM NaCl in the above buffer at a flow rate of 2.5 mL/min. Each preparation of partially purified HDA enzyme is titrated to determine the optimal amount needed to obtain a signal to noise ratio of at least 5 to 1. Generally, 20–30 µl of partially purified HDA (5–10 mg protein/mL) is mixed with 2 µL of compound solution in DMSO in a deep well titer plate (Beckman). The compounds are serially diluted in DMSO to generate stocks at 20-fold of the assay concentrations. Final concentrations of compounds in the assay are 10 µM, 2 µM, 400 nM, 80 nM, and 16 nM with the final percentage of DMSO in each enzyme reaction equaling 0.1%. Each concentration of compound is assayed in duplicate. The substrate used in the reaction is a peptide of amino acid sequence, SGRGKGGKGLGKGGAKRHRKVLRD, corresponding to the twenty-four N-terminal amino acids of human histone H4, biotinylated at the N-terminus and pentaacetylated, at each lysine residue with $^3$H-acetate. To initiate the reaction, the substrate is diluted in 10 µL of Buffer A (100 mM Tris pH 8.0, 2 mM EDTA), added to the enzyme mixture and collected at the bottom of the deep well plate by centrifugation for 5 minutes at 1500 rpm. Following centrifugation, the mixture is incubated at 37° C. for 1.5 hr.

The reaction is stopped by the addition of 20 μL of the Stop Buffer (0.5N HCl, 0.08M Acetic Acid). At this point, the assay proceeds to the robotic extraction phase or is frozen for several days at −80° C.

The extraction of enzymatically cleaved $^3$H-acetate groups from the reaction mixture is achieved with the solvent TBME (t-butyl methyl ether) using the Tomtec Quadra 96 workstation. A program is written to add 200 μL of TBME to a 96 "deep well" plate. The workstation is programmed to aspirate 50 μL of air followed by 200 μL of TBME and finally another 25 μL of air, which is dispensed into the each well of the plate. The contents of the deep well were mixed thoroughly by pipetting 160 μL up and down 10 times. Before addition of TBME to the reaction mixture, it is necessary to "pre-wet" the pipette tips with TBME to prevent the solvent from dripping during the transfer to the deep well plate. The organic and aqueous phases in the deep well are separated by centrifugation at 1500 rpm for 5 min. Opti-Phase Supermix liquid scintillation cocktail (200 μL) (Wallac) is added to each well of the 96-well Trilux plate (Wallac). The deep well and Trilux plates are placed back on the workstation programmed to aspirate 25 μL of air into the pipette tips followed by 100 μL of the upper TBME phase and transfer it into the Trilux plate. The solutions are mixed by pipetting and expelling 50 μL, five times, within the same well. The Trilux plate is covered with clear film and read on a 1450 MicroBeta Trilux liquid scintillation and luminescence counter (Wallac) with a color/chemical quench and dpm correction.

In order to determine the $IC_{50}$ values, the data are analyzed on a spreadsheet. The analysis requires a correction for the background luminescence that is accomplished by subtracting the dpm values of wells without $^3$H substrate from the experimental wells. The corrected dpm values along with the concentrations of the compounds are used to calculate $IC_{50}$ using the user-defined spline function. This function utilizes linear regression techniques between data points to calculate the concentration of compounds that produced 50% inhibition. The results are shown in Table B2.

TABLE B2

| Compound | HDA Enzyme Activity $IC_{50}$ (μM) |
|---|---|
| CMD1 | 0.032 |
| CMD2 | 0.063 |
| CMD3 | 0.014 |
| CMD4 | 0.014 |
| CMD5 | 0.016 |
| CMDC | >10 |

EXAMPLE B3

The A549 non-small cell lung human tumor cell line is purchased from the American Type Culture Collection, Rockville, Md. The cell line is free of Mycoplasma contamination (Rapid Detection System by Gen-Probe, Inc., San Diego, Calif.) and viral contamination (MAP testing by MA BioServices, Inc., Rockville, Md.). The cell line is propagated and expanded in RPMI 1640 medium containing 10% heat-inactivated FBS (Life Technologies, Grand Island, N.Y.). Cell expansions for implantation are performed in cell factories (NUNC, purchased from Fisher Scientific, Springfield, N.J.). Cells are harvested at 50–90% confluency, washed once with HBSS containing 10% FBS, and suspended in 100% HBSS.

Outbred athymic (nu/nu) female mice ("Hsd:Athymic Nude-nu" from Harlan Sprague Dawley, Indianapolis, Ind.) are anesthetized with Metofane (Mallinckrodt Veterinary, Inc., Mundelein, Ill.), and 100 μL of the cell suspension containing $1 \times 10^7$ cells is injected subcutaneously into the right axillary (lateral) region of each animal. Tumors are allowed to grow for about 20 days until a volume of ~100 mm$^3$ is achieved. At this point, mice bearing tumors with acceptable morphology and size are sorted into groups of eight for the study. The sorting process produces groups balanced with respect to mean and range of tumor size. Antitumor activity is expressed as % T/C, comparing differences in tumor volumes for treatment group (T) to vehicle control group (C). Regressions are calculated using the formula: $(1-T/T_0) \times 100\%$, where T is the tumor volume for the treatment group at the end of the experiment, and $T_0$ is the tumor volume at the beginning of the experiment.

CMD1 is administered intravenously, once daily 5x/week for three weeks, at doses of 10, 25, 50, or 100 mg/kg. The final DMSO concentration is 10%. Each test group has eight mice. Tumors are measured, and individual animal body weights recorded. Table B3 shows the results on the 41$^{st}$ day.

TABLE B3

| COMPOUND | DOSE (mg/kg) | Δ MEAN TUMOR VOLUME*[1] (mm³ ± SEM*[3]) | % T/C | Δ % BODY WEIGHT*[2] (% ± SEM*[3]) |
|---|---|---|---|---|
| 10% DMSO/D5W*[4] | — | 376 ± 55 | — | +11.9 ± 0.2 |
| CMD1 | 10 | 121 ± 27 | 32 | +1.3 ± 0.3 |
| CMD1 | 25 | 77 ± 32 | 20 | −0.9 ± 0.3 |
| CMD1 | 50 | 57 ± 10 | 15 | −0.4 ± 0.3 |
| CMD1 | 100 | 28 ± 25 | 7 | +0.4 ± 0.3 |

Note:
*[1]Difference in mean tumor volume for a group of animals at the end of the experiment minus mean tumor volume at the beginning.
*[2]Difference in body weight for a group of animals at the end of the experiment minus mean tumor volume at the beginning.
*[3]Standard error of the mean
*[4]5% dextrose injection, USP.

EXAMPLE B4

Example B3 repeated except CMD2 is used. Table B4 shows the results.

TABLE B4

| COMPOUND | DOSE (mg/kg) | Δ MEAN TUMOR VOLUME (mm³ ± SEM) | % T/C | Δ % BODY WEIGHT (% ± SEM) |
|---|---|---|---|---|
| 10% DMSO/D5W | — | 135 ± 43 | — | +6.7 ± 1.1 |
| CMD2 | 25 | 37 ± 16 | 27 | −4.2 ± 2.5 |
| CMD2 | 50 | 29 ± 15 | 21 | −2.9 ± 1.5 |

EXAMPLE B5

Example B3 is repeated except the HCT116 colon tumor cell line is used in place of the A549 cell line. The HCT116 cell line is also obtained from American Type Culture Collection, Rockville, Md., and the cell line is free of Mycoplasma contamination and viral contamination. The results are recorded on the 34$^{th}$ day and are shown in Table B5.

147

TABLE B5

| COMPOUND | DOSE (mg/kg) | Δ MEAN TUMOR VOLUME (mm³ ± SEM) | % T/C | Δ % BODY WEIGHT (% ± SEM) |
|---|---|---|---|---|
| 10% DMSO/D5W | — | 759 ± 108 | — | −0.4 ± 0.4 |
| CMD1 | 50*[10] | 186 ± 40 | 25 | −7.4 ± 0.8 |
| CMD1 | 100 | 140 ± 38 | 18 | −3.2 ± 0.4 |

Note:
*[10]Seven mice are tested in this group.

EXAMPLE B6

Example B4 is repeated except the HCT116 colon tumor cell line is used in place of the A549 cell line. The HCT116 is also obtained from American Type Culture Collection, Rockville, Md., and the cell line is free of Mycoplasma contamination and viral contamination. The results are recorded on the 34$^{th}$ day and are shown in Table B6.

TABLE B6

| COMPOUND | DOSE (mg/kg) | Δ MEAN TUMOR VOLUME (mm³ ± SEM) | % T/C | Δ % BODY WEIGHT (% ± SEM) |
|---|---|---|---|---|
| 10% DMSO/D5W | — | 759 ± 108 | — | −0.4 ± 0.4 |
| CMD2 | 10 | 422 ± 75 | 56 | −10.2 ± 0.5 |
| CMD2 | 25 | 305 ± 47 | 40 | −7.0 ± 0.2 |
| CMD2 | 50 | 97 ± 30 | 13 | −7.3 ± 0.3 |
| CMD2 | 100 | 132 ± 30 | 17 | −9.4 ± 0.4 |

EXAMPLE B7

Annexin V binding was used as a marker for the early stages of apoptosis. A549, HCT116 and Normal Dermal Human Fibroblasts (NDHF) cells are treated separately with four compounds (CMD1, CMD2, CMD3 and CMD4) for 24 or 48 hours, stained with annexin V and compared to cells treated similarly with vehicle (DMSO). Cells are examined by fluorescence microscopy. Those undergoing apoptosis exhibit green fluorescent membrane staining. Viability is assessed by the counterstain, propidium iodide. Cells detected by red fluorescence are not viable. A small percentage of A549 and the majority of HCT116 cells exhibit cell surface staining with annexin V after 24 hour exposure to each of the four compounds. After 48 hour treatment, the majority of the A549 and HCT116 stain with annexin V and/or propidium iodide indicating that the compounds induce apoptotic cell death. In contrast, NDHF cells do not show noticeable annexin V staining after 24 hour exposure and limited annexin V staining with CMD3 after 48 hour. These data show that NDHF cells predominantly underwent non-lethal growth arrest upon compound treatment, consistent with the cell cycle profile.

The staining results demonstrate that the hydroxamate compounds of the present invention cause tumor cells to die by apoptosis, while causing normal fibroblast to predominantly undergo cell cycle arrest, clearly demonstrating the selective efficacy of the present compounds.

148

What is claimed is:
1. A compound of the formula (I)

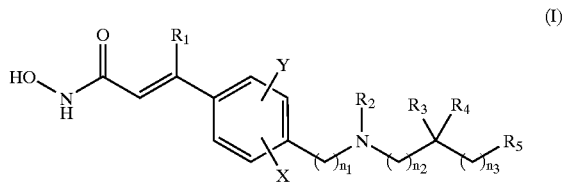

wherein $R_1$ is H, halo, or a straight chain $C_1$–$C_6$ alkyl;

$R_2$ is selected from H, $C_1$–$C_{10}$ alkyl, $C_4$–$C_9$ cycloalkyl, $C_4$–$C_9$ heterocycloalkyl, $C_4$–$C_9$ heterocycloalkylalkyl, cycloalkylalkyl, aryl, heteroaryl, arylalkyl, heteroarylalkyl, —$(CH_2)_nC(O)R_6$, —$(CH_2)_nOC(O)R_6$, amino acyl, HON—C(O)—CH=C($R_1$)-aryl-alkyl- and —$(CH_2)_nR_7$;

$R_3$ and $R_4$ are the same or different and independently H, $C_1$–$C_6$ alkyl, acyl or acylamino, or $R_3$ and $R_4$ together with the carbon to which they are bound represent C=O, C=S, or C=$NR_8$;

$R_5$ is selected from polyheteroaryl which is substituted or unsubstituted indol-3-yl;

n, $n_1$, $n_2$ and $n_3$ are the same or different and independently selected from 0–6, when n, is 1–6, each carbon atom can be optionally and independently substituted with $R_3$ and/or $R_4$;

X and Y are the same or different and independently selected from H, halo, $C_1$–$C_4$ alkyl, $NO_2$, C(O)$R_1$, $OR_9$, $SR_9$, CN, and $NR_{10}R_{11}$;

$R_6$ is selected from H, $C_1$–$C_6$ alkyl, $C_4$–$C_9$ cycloalkyl, $C_4$–$C_9$ heterocycloalkyl, cycloalkylalkyl, aryl, heteroaryl, arylalkyl, heteroarylalkyl, $OR_{12}$, and $NR_{13}R_{14}$;

$R_7$ is selected from $OR_{15}$, $SR_{15}$, S(O)$R_{16}$, $SO_2R_{17}$, $NR_{13}R_{14}$, and $NR_{12}SO_2R_6$;

$R_8$ is selected from H, $OR_{15}$, $NR_{13}R_{14}$, $C_1$–$C_6$ alkyl, $C_4$–$C_9$ cycloalkyl, $C_4$–$C_9$ heterocycloalkyl, aryl, heteroaryl, arylalkyl, and heteroarylalkyl;

$R_9$ is selected from $C_1$–$C_4$ alkyl and C(O)-alkyl;

$R_{10}$ and $R_{11}$ are the same or different and independently selected from H, $C_1$–$C_4$ alkyl, and —C(O)-alkyl;

$R_{12}$ is selected from H, $C_1$–$C_6$ alkyl, $C_4$–$C_9$ cycloalkyl, $C_4$–$C_9$ heterocycloalkyl, $C_4$–$C_9$ heterocycloalkylalkyl, aryl, mixed aryl and non-aryl polycycle, heteroaryl, arylalkyl, and heteroarylalkyl;

$R_{13}$ and $R_{14}$ are the same or different and independently selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl, amino acyl, or $R_{13}$ and $R_{14}$ together with the nitrogen to which they are bound are $C_4$–$C_9$ heterocycloalkyl, heteroaryl, polyheteroaryl, non-aromatic polyheterocycle or mixed aryl and non-aryl polyheterocycle;

$R_{15}$ is selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl and $(CH_2)_mZR_{12}$;

$R_{16}$ is selected from $C_1$–$C_6$ alkyl, $C_4$–$C_9$ cycloalkyl, $C_4$–$C_9$ heterocycloalkyl, aryl, heteroaryl, polyheteroaryl, arylalkyl, heteroarylalkyl and $(CH_2)_mZR_{12}$;

$R_{17}$ is selected from $C_1$–$C_6$ alkyl, $C_4$–$C_9$ cycloalkyl, $C_4$–$C_9$ heterocycloalkyl, aryl, aromatic polycycle, heteroaryl, arylalkyl, heteroarylalkyl, polyheteroaryl and $NR_{13}R_{14}$;

m is an integer selected from 0 to 6; and

Z is selected from O, $NR_{13}$, S and S(O);

or a pharmaceutically acceptable salt thereof.

2. A compound of claim 1 wherein each of $R_1$, X, Y, $R_3$, and $R_4$ is H.

3. A compound of claim 2 one of $n_2$ and $n_3$ is zero and the other is 1.

4. A compound of claim 3 wherein $R_2$ is H or $—CH_2—CH_2—OH$.

5. A compound of claim 1 of the formula (Ia)

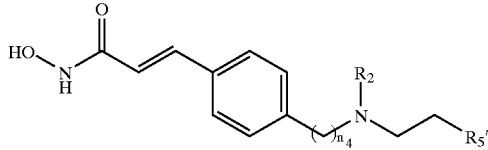

(Ia)

wherein $n_4$ is 0–3, $R_2$ is selected from H, $C_1–C_6$ alkyl, $C_4–C_9$ cycloalkyl, $C_4–C_9$ heterocycloalkyl, alkylcycloalkyl, aryl, heteroaryl, arylalkyl, heteroarylalkyl, $—(CH_2)_nC(O)R_6$, amino acyl and $—(CH_2)_nR_7$;

$R_5'$ is polyheteroaryl which is substituted or unsubstituted indol-3-yl, or a pharmaceutically acceptable salt thereof.

6. A compound of claim 1 of formula Ib:

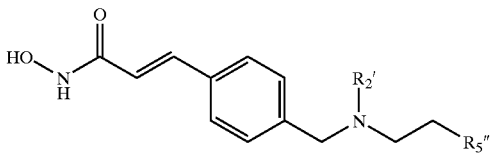

(Ib)

wherein $R_2'$ is selected from H, $C_1–C_6$ alkyl, $C_4–C_6$ cycloalkyl, alkylcycloalkyl, and $(CH_2)_{2-4}OR_{21}$ where $R_{21}$ is H, methyl, ethyl, propyl, or isopropyl, and $R_5''$ is unsubstituted or substituted 1H-indol-3-yl, or a pharmaceutically acceptable salt thereof.

7. A compound of claim 1 of formula (Id)

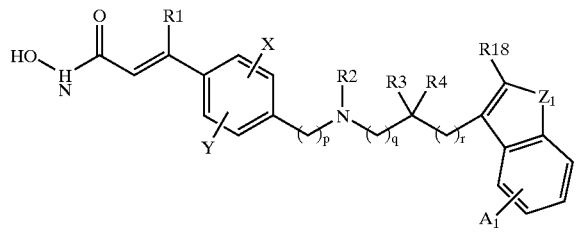

(Id)

wherein $Z_1$ is $N—R_{20}$;

R18 is H, halo, $C_1–C_6$alkyl, $C_3–C_7$cycloalkyl, aryl, or heteroaryl;

$R_{20}$ is H, $C_1–C_6$alkyl, $C_1–C_6$alkyl-$C_3–C_9$cycloalkyl, aryl, heteroaryl, arylalkyl, heteroarylalkyl, acyl or sulfonyl;

$A_1$ is 1, 2 or 3 substituents which are independently H, $C_1–C_6$alkyl, $—OR_{19}$, halo, alkylamino, aminoalkyl, halo, or heteroarylalkyl, $R_2$ is selected from H, $C_1–C_6$ alkyl, $C_4–C_9$ cycloalkyl, $C_4–C_9$ heterocycloalkyl, alkylcycloalkyl, aryl, heteroaryl, arylalkyl, heteroarylalkyl, $—(CH_2)_nC(O)R_6$, amino acyl and $—(CH_2)_nR_7$;

$R_{19}$ is selected from H, $C_1–C_6$alkyl, $C_4–C_9$cycloalkyl, $C_4–C_9$heterocycloalkyl, aryl, heteroaryl, arylalkyl, and heteroarylalkyl;

p is 0–3, and q is 1–5 and r is 0 or q is 0 and r is 1–5 or a pharmaceutically acceptable salt thereof.

8. A compound of claim 7 wherein $R_2$ is H or $—CH_2—CH_2—OH$ and the sum of q and r is 1.

9. A compound of claim 1 of the formula (Id)

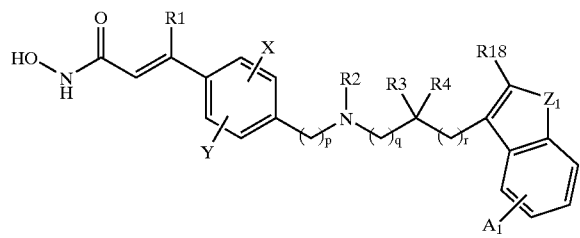

(Id)

wherein $Z_1$ is $N—R_{20}$,

R18 is H, halo, $C_1–C_6$alkyl, $C_3–C_7$cycloalkyl, unsubstituted phenyl, substituted phenyl, or heteroaryl, $R_{20}$ is H, $C_1–C_6$alkyl, $C_1–C_6$alkyl-$C_3–C_9$cycloalkyl, aryl, heteroaryl, arylalkyl, heteroarylalkyl, acyl or sulfonyl;

$A_1$ is 1, 2 or 3 substituents which are independently H, $C_1–C_6$alkyl, $—OR_{19}$, or halo, $R_{19}$ is selected from H, $C_1–C_6$alkyl, $C_4–C_9$cycloalkyl, $C_4–C_9$heterocycloalkyl, aryl, heteroaryl, arylalkyl, heteroarylalkyl and $—(CH_2CH=CH(CH_3)(CH_2))_{1-3}H$;

p is 0–3, and q is 1–5 and r is 0 or q is 0 and r is 1–5, or a pharmaceutically acceptable salt thereof.

10. A compound of claim 9 wherein $R_2$ is H or $—CH_2—CH_2—OH$ and the sum of q and r is 1.

11. A compound of claim 9 wherein R18 is H, fluoro, chloro, bromo, a $C_1–C_4$alkyl group, a $C_3–C_7$cycloalkyl group, phenyl or a heteroaryl ring.

12. A compound of claim 9 wherein $R_2$ is H, or $—(CH_2)_sCH_2OH$ and wherein s is 1–3.

13. A compound of claim 12 wherein $R_1$ is H and X and Y are each H, and wherein q is 1–3 and r is 0 or wherein q is 0 and r is 1–3.

14. A compound of claim 9 wherein R18 is H, methyl, ethyl, t-butyl, trifluoromethyl, cyclohexyl, phenyl, 4-methoxyphenyl, 4-trifluoromethylphenyl, 2-furanyl, 2-thiophenyl, or 2-, 3- or 4-pyridyl.

15. A compound of claim 14 wherein $R_2$ is H, or $—(CH_2)_sCH_2OH$ and wherein s is 1–3.

16. A compound of claim 15 wherein p is 1–3.

17. A compound of claim 16 wherein $R_1$ is H and X and Y are each H, and wherein q is 1–3 and r is 0 or wherien q is 0 and r is 1–3.

18. A compound of claim 17 wherein $R_2$ H or —$CH_2$—$CH_2$—OH and the sum of q and r is 1.

19. A compound of claim 9 wherein $R_{20}$ is H or $C_1$–$C_6$alkyl.

20. A compound of claim 9 selected from the group consisting of N-hydroxy-3-[4-[[(2-hydroxyethyl)[2-(1H-indol-3-yl)ethyl]-amino]methyl]phenyl]-2E-2-propenamide, or a pharmaceutically acceptable salt thereof.

21. A pharmaceutical composition comprising a pharmaceutically effective amount of a compound of formula (I)

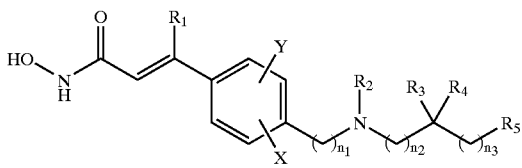

(I)

wherein $R_1$ is H, halo, or a straight chain $C_1$–$C_6$ alkyl;

$R_2$ is selected from H, $C_1$–$C_{10}$ alkyl, $C_4$–$C_9$ cycloalkyl, $C_4$–$C_9$ heterocycloalkyl, $C_4$–$C_9$ heterocycloalkylalkyl, cycloalkylalkyl, aryl, heteroaryl, arylalkyl, heteroarylalkyl, —$(CH_2)_nC(O)R_6$, —$(CH_2)_nOC(O)R_6$, amino acyl, HON—C(O)—CH=C($R_1$)-aryl-alkyl- and —$(CH_2)_nR_7$;

$R_3$ and $R_4$ are the same or different and independently H, $C_1$–$C_6$ alkyl, acyl or acylamino, or $R_3$ and $R_4$ together with the carbon to which they are bound represent C=O, C=S, or C=$NR_8$g;

$R_5$ is polyheteroaryl which is substituted or unsubstituted indol-3-yl;

n, $n_1$, $n_2$ and $n_3$ are the same or different and independently selected from 0–6, when n, is 1–6, each carbon atom can be optionally and independently substituted with $R_3$ and/or $R_4$;

X and Y are the same or different and independently selected from H, halo, $C_1$–$C_4$ alkyl, $NO_2$, $C(O)R_1$, $OR_9$, $SR_9$, CN, and $NR_{10}R_{11}$;

$R_6$ is selected from H, $C_1$–$C_6$ alkyl, $C_4$–$C_9$ cycloalkyl, $C_4$–$C_9$ heterocycloalkyl, cycloalkylalkyl, aryl, heteroaryl, arylalkyl, heteroarylalkyl, $OR_{12}$, and $NR_{13}R_{14}$;

$R_7$ is selected from $OR_{15}$, $SR_{15}$, $S(O)R_{16}$, $SO_2R_{17}$, $NR_{13}R_{14}$, and $NR_{12}SO_2R_6$;

$R_8$ is selected from H, $OR_{15}$, $NR_{13}R_{14}$, $C_1$–$C_6$ alkyl, $C_4$–$C_9$ cycloalkyl, $C_4$–$C_9$ heterocycloalkyl, aryl, heteroaryl, arylalkyl, and heteroarylalkyl;

$R_9$ is selected from $C_1$–$C_4$ alkyl and C(O)-alkyl;

$R_{10}$ and $R_{11}$ are the same or different and independently selected from H, $C_1$–$C_4$ alkyl, and —C(O)-alkyl;

$R_{12}$ is selected from H, $C_1$–$C_6$ alkyl, $C_4$–$C_9$ cycloalkyl, $C_4$–$C_9$ heterocycloalkyl, $C_4$–$C_9$ heterocycloalkylalkyl, aryl, mixed aryl and non-aryl polycycle, heteroaryl, arylalkyl, and heteroarylalkyl;

$R_{13}$ and $R_{14}$ are the same or different and independently selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl, amino acyl, or $R_{13}$ and $R_{14}$ together with the nitrogen to which they are bound are $C_4$–$C_9$ heterocycloalkyl, heteroaryl, polyheteroaryl, non-aromatic polyheterocycle or mixed aryl and non-aryl polyheterocycle;

$R_{15}$ is selected from H, $C_1$–$C_6$ alkyl, $C_4$–$C_9$ cycloalkyl, $C_4$–$C_9$ heterocycloalkyl, aryl, heteroaryl, arylalkyl, heteroarylalkyl and $(CH_2)_mZR_{12}$;

$R_{16}$ is selected from $C_1$–$C_6$ alkyl, $C_4$–$C_9$ cycloalkyl, $C_4$–$C_9$ heterocycloalkyl, aryl, heteroaryl, polyheteroaryl, arylalkyl, heteroarylalkyl and $(CH_2)_mZR_{12}$;

$R_{17}$ is selected from $C_1$–$C_6$ alkyl, $C_4$–$C_9$ cycloalkyl, $C_4$–$C_9$ heterocycloalkyl, aryl, aromatic polycycle, heteroaryl, arylalkyl, heteroarylalkyl, polyheteroaryl and $NR_{13}R_{14}$;

m is an integer selected from 0 to 6; and

Z is selected from O, $NR_{13}$, S and S(O);

or a pharmaceutically acceptable salt thereof, and a pharmaceutically acceptable carrier.

22. A pharmaceutical composition of claim 21 wherein the compound of formula (I) is selected from the group consisting of N-hydroxy-3-[4-[[(2-hydroxyethyl)[2-(1H-indol-3-yl)ethyl]-amino]methyl]phenyl]-2E-2-propenamide, or a pharmaceutically acceptable salt thereof.

23. A compound of claim 1 wherein $R_3$ and $R_4$ are each H.

24. A compound of claim 8, wherein $R_1$, $R_3$ and $R_4$ are each H, X and Y are each H, $R_{20}$ is H or $C_1$–$C_4$alkyl and p is 1.

25. A pharmaceutical composition of claim 21, which comprises a pharmaceutically effective amount of a compound of formula (Ic)

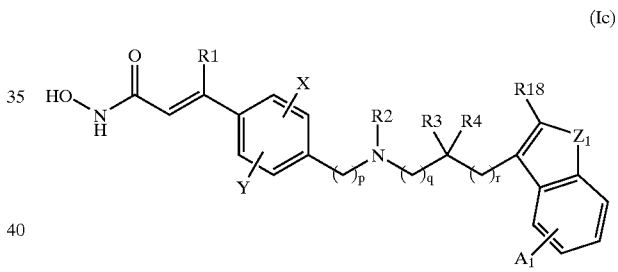

(Ic)

wherein $Z_1$ is N—$R_{20}$;

$R_{18}$ is H, halo, $C_1$–$C_6$alkyl, $C_3$-$C_7$cycloalkyl, aryl, or heteroaryl;

$R_{20}$ is H, $C_1$–$C_6$alkyl, $C_1$–$C_6$alkyl-$C_3$–$C_9$cycloalkyl, aryl, heteroaryl, arylalkyl, heteroarylalkyl, acyl or sulfonyl;

$A_1$ is 1, 2 or 3 substituents which are independently H, $C_1$-$C_6$alkyl, —$OR_{19}$, halo, alkylamino, aminoalkyl, halo, or heteroarylalkyl, $R_2$ is selected from H, $C_1$–$C_6$ alkyl, $C_4$–$C_9$ cycloalkyl, $C_4$–$C_9$ heterocycloalkyl, alkylcycloalkyl, aryl, heteroaryl, arylalkyl, heteroarylalkyl, —$(CH_2)_nC(O)R_6$, amino acyl and —$(CH_2)_nR_7$;

$R_{19}$ is selected from H, $C_1$–$C_6$alkyl, $C_4$–$C_9$cycloalkyl, $C_4$–$C_9$heterocycloalkyl, aryl, heteroaryl, arylalkyl, and heteroarylalkyl;

p is 0–3, and q is 1–5 and r is 0 or q is 0 and r is 1–5 or a pharmaceutically acceptable salt thereof.

26. A pharmaceutical composition of claim 25, which comprises a pharmaceutically effective amount a compound of formula (Ic)
wherein
$R_{18}$ is H, halo, $C_1$–$C_6$alkyl, $C_3$–$C_7$cycloalkyl, unsubstituted phenyl, substituted phenyl, or heteroaryl,
$R_{20}$ is H, $C_1$–$C_6$alkyl-$C_1$–$C_6$alkyl-$C_3$–$C_9$ cycloalkyl, aryl, heteroaryl, arylalkyl, heteroarylalkyl, acyl or sulfonyl;
$A_1$ is 1, 2 or 3 substituents which are independently H, $C_1$–$C_6$alkyl, —$OR_{19}$, or halo, or a pharmaceutically acceptable salt thereof.

27. A pharmaceutical composition of claim 25, wherein $R_1$, $R_3$ and $R_4$ are each H, $R_2$ is H or —$CH_2CH_2OH$, X and Y are each H, $R_{20}$ is H or $C_1$–$C_4$alkyl, p is 1 and q is 1.

* * * * *

UNITED STATES PATENT AND TRADEMARK OFFICE
CERTIFICATE OF CORRECTION

PATENT NO. : 6,552,065 B2
DATED : April 22, 2003
INVENTOR(S) : Stacy William Remiszewski et al.

It is certified that error appears in the above-identified patent and that said Letters Patent is hereby corrected as shown below:

Column 150,
Line 1, should read -- $A_1$ is 1, 2 or 3 substituents which are independently H, --

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,552,065 B2
APPLICATION NO. : 09/944275
DATED : April 22, 2003
INVENTOR(S) : Stacy W. Remiszewski et al.

Page 1 of 1

It is certified that error appears in the above-identified patent and that said Letters Patent is hereby corrected as shown below:

In the Claims

Column 148
Line 28 should read -- dently selected from 0-6, when $n_1$ is 1-6, each carbon Column 151
Line 34 should read -- dently selected from 0-6, when $n_1$ is 1-6, each carbon Signed and Sealed this
Twenty-third Day of February, 2016

Michelle K. Lee
*Director of the United States Patent and Trademark Office*